United States Patent
Höskuldsson et al.

(10) Patent No.: US 11,896,386 B2
(45) Date of Patent: Feb. 13, 2024

(54) COHERENCE-BASED METHOD, APPARATUS, AND SYSTEM FOR IDENTIFYING CORRESPONDING SIGNALS OF A PHYSIOLOGICAL STUDY

(71) Applicant: NOX MEDICAL EHF, Reykjavik (IS)

(72) Inventors: Sveinbjörn Höskuldsson, Reykjavik (IS); Jón Skírnir Ágústsson, Reykjavik (IS)

(73) Assignee: NOX MEDICAL EHF, Reykjavik (IS)

( * ) Notice: Subject to any disclaimer, the term of this patent is extended or adjusted under 35 U.S.C. 154(b) by 904 days.

(21) Appl. No.: 15/997,282

(22) Filed: Jun. 4, 2018

(65) Prior Publication Data
US 2018/0344241 A1    Dec. 6, 2018

Related U.S. Application Data

(60) Provisional application No. 62/514,235, filed on Jun. 2, 2017.

(51) Int. Cl.
*A61B 5/00* (2006.01)
*A61B 5/0205* (2006.01)
(Continued)

(52) U.S. Cl.
CPC .......... *A61B 5/4818* (2013.01); *A61B 5/0205* (2013.01); *A61B 5/02405* (2013.01);
(Continued)

(58) Field of Classification Search
CPC ... A61B 5/4815; A61B 5/4818; A61B 5/4806; A61B 5/7246; A61B 5/0225;
(Continued)

(56) References Cited

U.S. PATENT DOCUMENTS

| | | |
|---|---|---|
| 937,130 A | 10/1909 | Williams |
| 1,115,459 A | 10/1914 | Abizaid |

(Continued)

FOREIGN PATENT DOCUMENTS

| | | |
|---|---|---|
| DE | 19941500 A1 | 3/2001 |
| EP | 2324760 A2 | 5/2011 |

(Continued)

OTHER PUBLICATIONS

Duarte, "Detect Peaks in Data Based on Their Amplitude and Other Features.," retrieved from https://github.com/demotu/BMC/blob/master/functions/detect_peaks.py on Jun. 1, 2018, Oct. 3, 2014, 3 Pages.

(Continued)

*Primary Examiner* — Michael W Kahelin
(74) *Attorney, Agent, or Firm* — Workman Nydegger

(57) ABSTRACT

A method, apparatus, and system for determining a correspondence of physiological data obtained in a physiological study of a subject. The method includes extracting a first signal from the physiological study. A second signal from the physiological study is also extracted. The first signal and the second signal are obtained by one or more biometric sensors. Data of the first signal and data of the second signal are stored on a memory storage. A coherency value is determined between components of the extracted first signal and components of the extracted second signal. And the correspondence of the physiological study data is determined based on the determined coherency value.

21 Claims, 45 Drawing Sheets

(51) Int. Cl.
 *A61B 5/024* (2006.01)
 *A61B 5/113* (2006.01)
 *A61B 5/318* (2021.01)
 *A61B 5/349* (2021.01)
 *A61B 5/0245* (2006.01)
 *A61B 5/08* (2006.01)
 *A61B 5/1455* (2006.01)

(52) U.S. Cl.
 CPC .......... *A61B 5/02416* (2013.01); *A61B 5/113* (2013.01); *A61B 5/1135* (2013.01); *A61B 5/318* (2021.01); *A61B 5/4806* (2013.01); *A61B 5/7221* (2013.01); *A61B 5/7246* (2013.01); *A61B 5/7278* (2013.01); *A61B 5/0245* (2013.01); *A61B 5/0809* (2013.01); *A61B 5/1455* (2013.01); *A61B 5/349* (2021.01); *A61B 5/4815* (2013.01); *A61B 5/7267* (2013.01)

(58) Field of Classification Search
 CPC ....... A61B 5/024; A61B 5/0402; A61B 5/113; A61B 5/0205; A61B 5/7221; A61M 2205/609
 See application file for complete search history.

(56) References Cited

U.S. PATENT DOCUMENTS

| | | | |
|---|---|---|---|
| 1,193,050 | A | 8/1916 | Orewiler |
| 2,305,277 | A | 12/1942 | Sloane et al. |
| 2,649,573 | A | 8/1953 | Goldberg et al. |
| 2,667,159 | A | 1/1954 | Goldberg et al. |
| 3,092,759 | A | 6/1963 | Sommer |
| 3,347,223 | A | 10/1967 | Pacela |
| 3,500,823 | A | 3/1970 | Richardson et al. |
| 3,560,845 | A | 2/1971 | Goldberg et al. |
| 3,685,105 | A | 8/1972 | Carlile et al. |
| 4,308,872 | A | 1/1982 | Watson et al. |
| 4,373,534 | A | 2/1983 | Watson |
| 4,430,777 | A | 2/1984 | Takeda |
| 4,671,591 | A | 6/1987 | Archer |
| 4,777,962 | A | 10/1988 | Watson et al. |
| 4,807,640 | A | 2/1989 | Watson et al. |
| 4,815,473 | A | 3/1989 | Watson et al. |
| 4,817,625 | A | 4/1989 | Miles |
| 4,832,608 | A | 5/1989 | Kroll |
| 4,834,109 | A | 5/1989 | Watson |
| 4,842,557 | A | 6/1989 | Muz |
| 5,301,678 | A | 4/1994 | Watson et al. |
| 5,326,272 | A | 7/1994 | Harhen et al. |
| 5,331,968 | A | 7/1994 | Williams et al. |
| 5,348,008 | A | 9/1994 | Bornn et al. |
| 5,353,793 | A | 10/1994 | Bornn |
| 5,543,012 | A | 8/1996 | Watson et al. |
| 6,148,486 | A | 11/2000 | Jehara et al. |
| 6,327,486 | B1 | 12/2001 | Nissila et al. |
| 6,341,504 | B1 | 1/2002 | Istook |
| 6,413,225 | B1 | 6/2002 | Sackner et al. |
| 6,461,307 | B1 | 10/2002 | Kristbjarnarson et al. |
| 6,807,438 | B1 | 10/2004 | Brun Del Re et al. |
| 6,993,378 | B2 | 1/2006 | Wiederhold et al. |
| 7,171,265 | B2 | 1/2007 | Hoium et al. |
| 7,267,652 | B2 | 9/2007 | Coyle et al. |
| 7,593,767 | B1 | 9/2009 | Modarres |
| 7,604,603 | B2 | 10/2009 | Sackner et al. |
| 7,670,295 | B2 | 3/2010 | Sackner et al. |
| 7,727,161 | B2 | 6/2010 | Coyle et al. |
| 7,762,953 | B2 | 7/2010 | Derchak et al. |
| 7,819,710 | B2 | 10/2010 | Mcintire et al. |
| 7,878,979 | B2 | 2/2011 | Derchak |
| 7,914,350 | B1 | 3/2011 | Bozich et al. |
| 8,025,539 | B2 | 9/2011 | Hermannsson |
| 8,033,996 | B2 | 10/2011 | Behar |
| 8,034,001 | B2 | 10/2011 | Gal |
| 8,052,612 | B2 | 11/2011 | Tang et al. |
| 8,137,270 | B2 | 3/2012 | Keenan et al. |
| 8,165,654 | B2 | 4/2012 | Tang et al. |
| 8,177,724 | B2 | 5/2012 | Derchak et al. |
| 8,193,821 | B2 | 6/2012 | Mueller et al. |
| 8,251,736 | B2 | 8/2012 | Mcintire et al. |
| 8,475,387 | B2 | 7/2013 | Derchak et al. |
| 8,579,794 | B2 | 11/2013 | Henke |
| 8,628,480 | B2 | 1/2014 | Derchak |
| 8,679,012 | B1 * | 3/2014 | Kayyali .............. A61B 5/6826 600/301 |
| 8,762,733 | B2 | 6/2014 | Derchak et al. |
| 8,777,868 | B2 | 7/2014 | Gal |
| 8,790,255 | B2 | 7/2014 | Behar |
| 8,790,272 | B2 | 7/2014 | Sackner et al. |
| 9,059,532 | B2 | 6/2015 | Hermannsson |
| 9,192,316 | B2 | 11/2015 | Hoskuldsson et al. |
| 10,011,054 | B1 | 7/2018 | Lee et al. |
| 2002/0032386 | A1 | 3/2002 | Sackner et al. |
| 2002/0032388 | A1 | 3/2002 | Kristbjarnarson et al. |
| 2002/0120207 | A1 | 8/2002 | Hoffman |
| 2003/0135127 | A1 | 7/2003 | Sackner et al. |
| 2005/0054941 | A1 | 3/2005 | Ting et al. |
| 2005/0119586 | A1 | 6/2005 | Coyle et al. |
| 2006/0122528 | A1 | 6/2006 | Gal |
| 2006/0258948 | A1 | 11/2006 | Linville |
| 2006/0282001 | A1 | 12/2006 | Noel et al. |
| 2007/0167089 | A1 | 7/2007 | Gobron et al. |
| 2009/0259135 | A1 | 10/2009 | Stasz |
| 2010/0060300 | A1 | 3/2010 | Muller et al. |
| 2010/0075527 | A1 | 3/2010 | Mcintire et al. |
| 2010/0075549 | A1 | 3/2010 | Mcintire et al. |
| 2010/0297868 | A1 | 11/2010 | Hermannsson |
| 2011/0151728 | A1 | 6/2011 | Astola |
| 2011/0248729 | A2 | 10/2011 | Mueler et al. |
| 2012/0101357 | A1 | 4/2012 | Hoskuldsson et al. |
| 2013/0303921 | A1 * | 11/2013 | Chu .................... A61B 5/0059 600/476 |
| 2014/0323847 | A1 | 10/2014 | Mccool |
| 2015/0126879 | A1 | 5/2015 | Hoskuldsson et al. |
| 2015/0280348 | A1 | 10/2015 | Hermannsson |
| 2016/0073921 | A1 | 3/2016 | Hoskuldsson et al. |
| 2016/0135715 | A1 | 5/2016 | Seppä et al. |
| 2017/0110823 | A1 | 4/2017 | Hermannsson et al. |
| 2017/0143206 | A1 * | 5/2017 | Kotz .................... A61B 5/0205 |
| 2018/0049678 | A1 | 2/2018 | Hoskuldsson et al. |

FOREIGN PATENT DOCUMENTS

| | | | |
|---|---|---|---|
| EP | 2324761 A2 | 5/2011 | |
| EP | 2417905 A1 | 2/2012 | |
| EP | 2484276 A2 | 8/2012 | |
| EP | 2484277 A2 | 8/2012 | |
| EP | 2484278 A3 | 8/2012 | |
| EP | 2508123 A1 | 10/2012 | |
| EP | 2508124 A2 | 10/2012 | |
| EP | 2584962 A2 | 5/2013 | |
| EP | 2589335 A2 | 5/2013 | |
| WO | 0202013 A1 | 1/2002 | |
| WO | 02080761 A2 | 10/2002 | |
| WO | 2006024024 A2 | 3/2006 | |
| WO | 20006066566 A2 | 6/2006 | |
| WO | 2008102140 A1 | 8/2008 | |
| WO | D071077-002 | 10/2008 | |
| WO | 20080133394 A1 | 11/2008 | |
| WO | 2011029136 A1 | 3/2011 | |
| WO | WO-2016110804 A1 * | 7/2016 | ........... A61B 5/0002 |
| WO | WO-2018001758 A1 * | 1/2018 | ........... A61B 5/7267 |
| WO | 2018033889 A1 | 2/2018 | |

OTHER PUBLICATIONS

Jones et al., "SciPy: Open Source Scientific Tools for Python," requested from http://www.scipy.org on Jun. 4, 2018, 2001, 3 Pages.
Orphanidou et al., "Signal-Quality Indices for the Electrocardiogram and Photoplethysmogram: Derivation and Applications to Wireless Monitoring," IEEE Journal of Biomedical and Health Informatics, vol. 19, No. 3, May 2015, pp. 832-838.

(56) References Cited

OTHER PUBLICATIONS

Roebuck et al., "A Review of Signals Used in Sleep Analysis," Physiological Measurement, vol. 35, 2014, pp. R1-R57.
International Search Report from PCT Application No. PCT/IS2011/050010, dated Feb. 29, 2012.
International Search Report from PCT Application No. PCT/IB2014/002760, dated Mar. 27, 2015.
International Preliminary Report on Patentability from PCT Application No. PCT/IB2014/002760, dated May 10, 2016.
"Disposable and Accessories Catalog for Respiratory Diagnostics", CareFusion, Natus Medical Inc., 2009, 138 Pages.
International Search Report from PCT Application No. PCT/IS2010/000007, dated Oct. 1, 2010.
Cohen, K.P. et al., "Breath Detection Using a Fuzzy Neural Network and Sensor Fusion", 1995 International Conference on Acoustics, Speech, and Signal Processing, May 9-12, 1995, vol. 5, pp. 3491-3494.
Stromberg, N.O.T., "Error analysis of a natural breathing calibration method for respiratory inductive blethysmography", Medical & Biological Engineering & Computing 2001, vol. 39, No. 3, May 1, 2001, pp. 310-314.
Cohen, Kevin P et al., "Comparison of Impedance and Inductance Ventilation Sensors on Adults During Breathing, Motion, and Simulated Airway Obstruction", IEEE Transactions on Biomedical Engineering, vol. 44, No. 7, Jul. 1, 1997, pp. 555-565.
Sackner et al., "Calibration of Respiratory Inductive Plethysmograph During Natural Breathing", The American Physiological Society, vol. 66, 1989, pp. 410-420.
Konno et al., "Static Volume-Pressure Characteristics of the Rib Cage and Abdomen", Journal of Applied Physiology, vol. 24, No. 4, Apr. 1968, pp. 544-548.
International Search Report from PCT Application No. PCT/IB2017/053128, dated Aug. 9, 2017.
Escobar et al., "Nu-Way Snaps and Snap Leads: an Important Connection in the History of Behavior Analysis," Behav Analyst, 2014,vol. 37, pp. 95-107.
Agustsson et al., "White Paper RIP Signal Assessment," Apr. 21, 2017, 21 Pages.
Dehkordi et al., "Monitoring Torso Acceleration for Estimating the Respiratory Flow and Efforts for Sleep Apnea Detection," 34th Annual International Conference of the IEEE EMBS, Aug. 28, 2012, pp. 6345-6348.
International Search Report and Written Opinion from PCT Application No. PCT/IB2017/055022, dated Nov. 17, 2017.
De Groote et al., "Mathematical Assessment of Qualitative Diagnostic Calibration for Respiratory Inductive Plethysmorgraphy," Journal of Applied Physiology, vol. 90, 2001, pp. 1025-1030.
Augousti et al., "Comparative Analysis of the Isovolume Calibration Method for Non-Invasive Respiratory Monitoring Techniques Based on Area Transduction Versus Circumference Transduction Using the Connected Cylinders Model," Physiological Measurement, vol. 32, 2011, pp. 1265-1274.
International Search Report and Written Opinion from PCT Application No. PCT/IB2018/056892, dated Dec. 13, 2018.
Agha et al., "Facial Phenotype in Obstructive Sleep Apnea-Hypopnea Syndrome: A Systematic Review and Meta-Analysis," Journal of Sleep Research, vol. 26, 2017, pp. 122-131.
Agrawal et al., "Sound Frequency Analysis and the Site of Snoring in Natural and Induced Sleep," Clinical Otolaryngology, vol. 27, 2002, pp. 162-166.
Akoumianaki et al., "The Application of Esophageal Pressure Measurement in Patients with Respiratory Failure," American Journal of Respiratory and Critical Care Medicine, vol. 189, No. 5, Mar. 1, 2014, pp. 520-531.
Arnardottir et al., "Snoring—Validation of Different Objective Measurements," European Respiratory Society Annual Congress 2013, 1 Page.
Arnardottir et al., "How to Measure Snoring? A Comparison of the Microphone, Cannula and Piezoelectric Sensor," Journal of Sleep Research, vol. 25, 2016, pp. 158-168.
Arnardottir et al., "Obstructive Sleep Apnoea in the General Population: Highly Prevalent but Minimal Symptoms," European Respiratory Journal, vol. 47, 2016, pp. 194-202.
Ayappa et al., "Non-Invasive Detection of Respiratory Effort-Related Arousals (RERAs) by a Nasal Cannula/Pressure Transducer System," Sleep, vol. 23, No. 6, 2000, pp. 763-771.
Berry et al., "Use of Chest Wall Electromyography to Detect Respiratory Effort During Polysomnography," Journal of Clinical Sleep Medicine, vol. 12, No. 9, 2016, pp. 1239-1244.
Berry et al., "AASM Scoring Manual Updates for 2017 (Version 2.4)," Journal of Clinical Sleep Medicine, vol. 13, No. 6, 2017, pp. 665-666.
Bloch et al., "Breathing Pattern During Sleep Disruptive Snoring," European Respiratory Journal, vol. 10, 1997, pp. 576-586.
Capistrano et al., "Facial Morphology and Obstructive Sleep Apnea," Dental Press Journal of Orthodontics, vol. 20, No. 6, Nov. 2015, pp. 60-67.
Eckert et al., "Pathophysiology of Adult Obstructive Sleep Apnea," Proceedings of the American Thoracic Society, vol. 5, 2008, pp. 144-153.
Faber et al., "Available Techniques for Objective Assessment of Upper Airway Narrowing in Snoring and Sleep Apnea," Sleep and Breathing, vol. 7, No. 2, 2003, pp. 77-86.
Ghafarian et al., "A Review on Human Respiratory Modeling," Tanaffos, vol. 15, No. 2, 2016, pp. 61-69.
Guilleminault et al., "Variability of Respiratory Effort in Relation to Sleep Stages in Normal Controls and Upper Airway Resistance Syndrome Patients," Sleep Medicine, vol. 2, 2001, pp. 397-406.
Harris et al., "GPCR Signalling in Hypertension: Role of GRKs," Clinical Science, vol. 115, 2008, pp. 79-89.
Heinzer et al., "Prevalence of Sleep-Disordered Breathing in the General Population: the HypnoLaus Study," Lancet Respiratory Medicine, vol. 3, No. 4, Apr. 2015, pp. 310-318.
Huo et al., "Endoscopic Upper Airway Evaluation in Obstructive Sleep Apnea: Mueller's Maneuver Versus Simulation of Snoring," Sleep Breath, vol. 19, 2015, pp. 661-667.
Konno et al., "Measurement of the Separate Volume," Journal of Applied Physiology, vol. 22, No. 3, 1967, pp. 407-422.
Kushida et al., "Technical Protocol for the use of Esophageal Manometry in the Diagnosis of Sleep-Related Breathing Disorders," Sleep Medicine, vol. 3, 2002, pp. 163-173.
Lee et al., "Energy Types of Snoring Sounds in Patients with Obstructive Sleep Apnea Syndrome: A Preliminary Observation," PLOS ONE, vol. 7, No. 12, Dec. 2012, 11 Pages.
Luo et al., "Diaphragm Electromyography Using an Oesophageal Catheter: Current Concepts," Clinical Science, vol. 115, 2008, pp. 233-244.
Masa et al., "Apnoeic and Obstructive Nonapnoeic Sleep Respiratory Events," European Respiratory Journal, vol. 34, 2009, pp. 156-161.
Otis et al., "Mechanical Factors in Distribution of Pulmonary Ventilation," Journal of Applied Physiology, vol. 8, No. 4, Jan. 1956, pp. 427-443.
Peppard et al., "Increased Prevalence of Sleep-Disordered Breathing in Adults," American Journal of Epidemiology, vol. 177, No. 9, Apr. 14, 2013, pp. 1006-1014.
Spinowitz et al., "Patterns of Upper Airway Obstruction on Drug-Induced Sleep Endoscopy in Patients with Sleep-Disordered Breathing with AHI < 5," American Academy of Otolaryngology—Head and Neck Surgery, 2017, 6 Pages.
Terrill et al., "Quantifying the Ventilatory Control Contribution to Sleep Apnoea Using Polysomnography," European Respiratory Journal, vol. 45, 2015, pp. 408-418.
Vandenbussche et al., "Assessment of Respiratory Effort During Sleep: Esophageal Pressure Versus Noninvasive Monitoring Techniques," Sleep Medicine Reviews, vol. 24, 2015, pp. 28-36.
Wellman et al., "A Method for Measuring and Modeling the Physiological Traits Causing Obstructive Sleep Apnea," Journal of Applied Physiology, vol. 110, 2011, pp. 1627-1637.
Wilson, "Compartmental Models of the Chest Wall and the Origin of Hoover's Sign," Respiratory Physiology & Neurobiology, vol. 210, 2015, pp. 23-29.

(56) References Cited

OTHER PUBLICATIONS

International Search Report from PCT Application No. PCT/IB2018/053993, dated Aug. 24, 2018.
Lester et al., ""Are You With Me?"—Using Accelerometers to Determine if Two Devices are Carried by the Same Person," Pervasive, 2004, pp. 33-50.
Nino et al., "Robust Spectral Analysis of Thoraco-Abdominal Motion and Oxymetry in Obstructive Sleep Apnea," 35th Annual International Conference of the IEEE EMBS, Jul. 3, 2013, pp. 2906-2910.

* cited by examiner

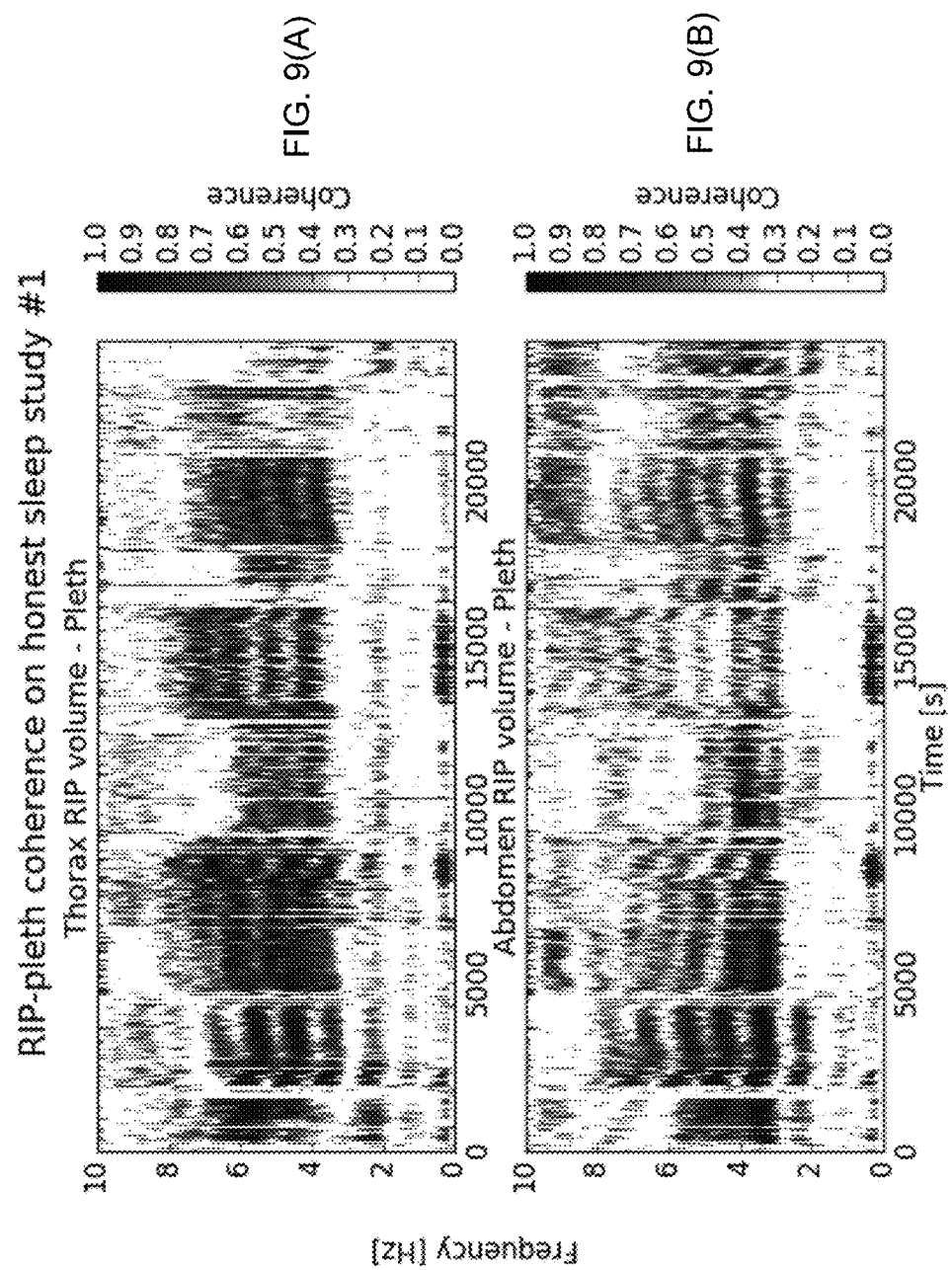

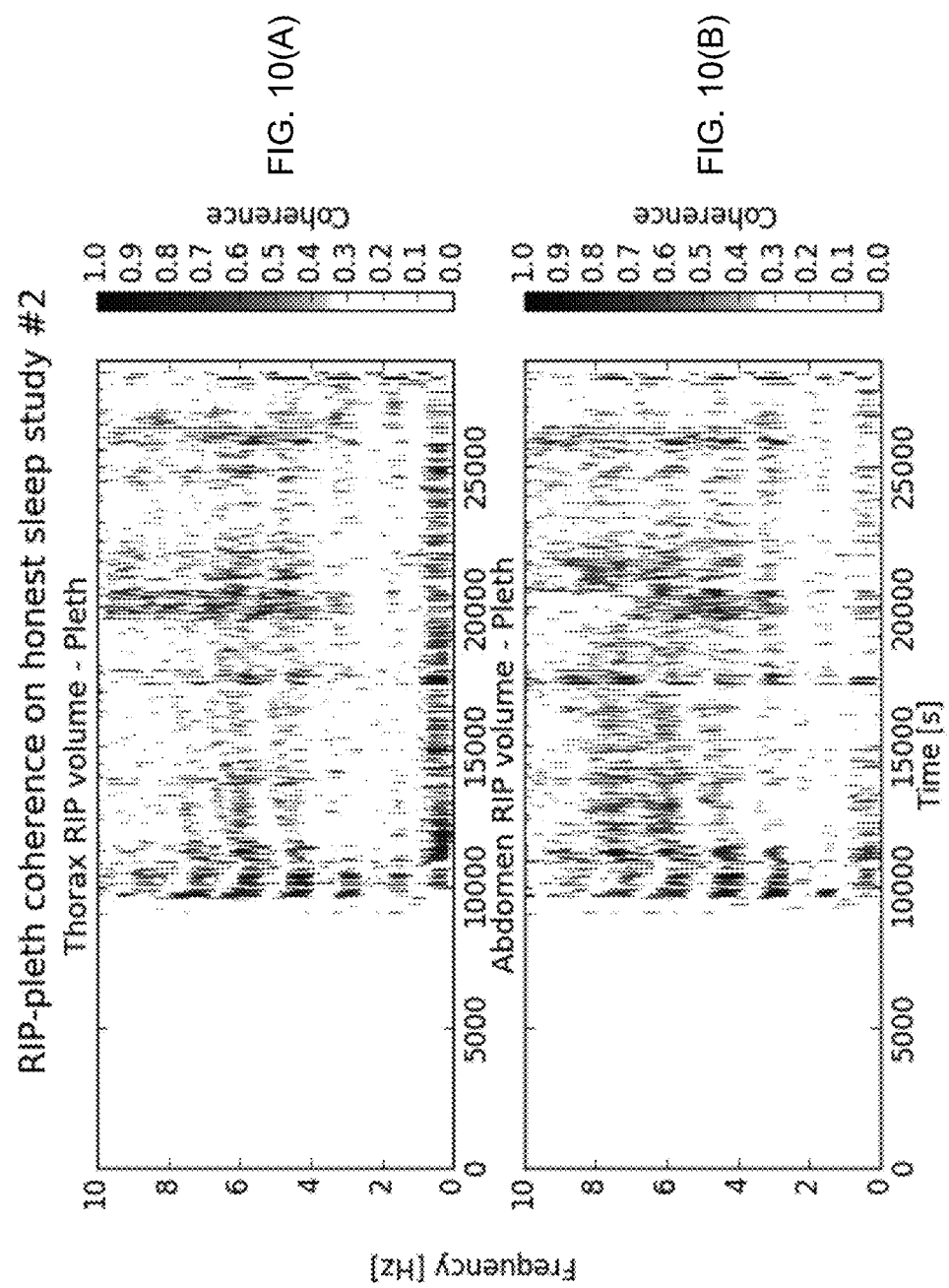

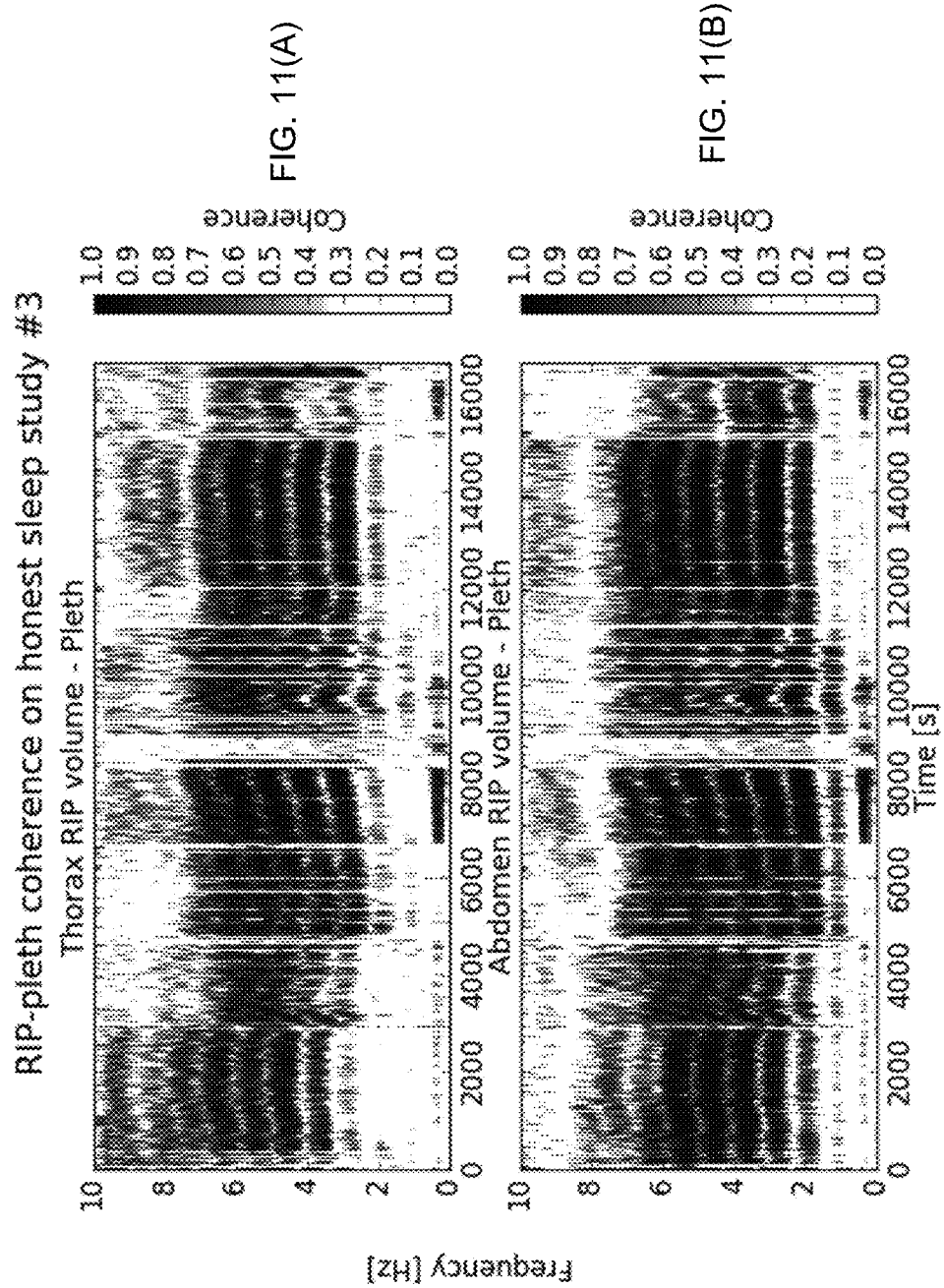

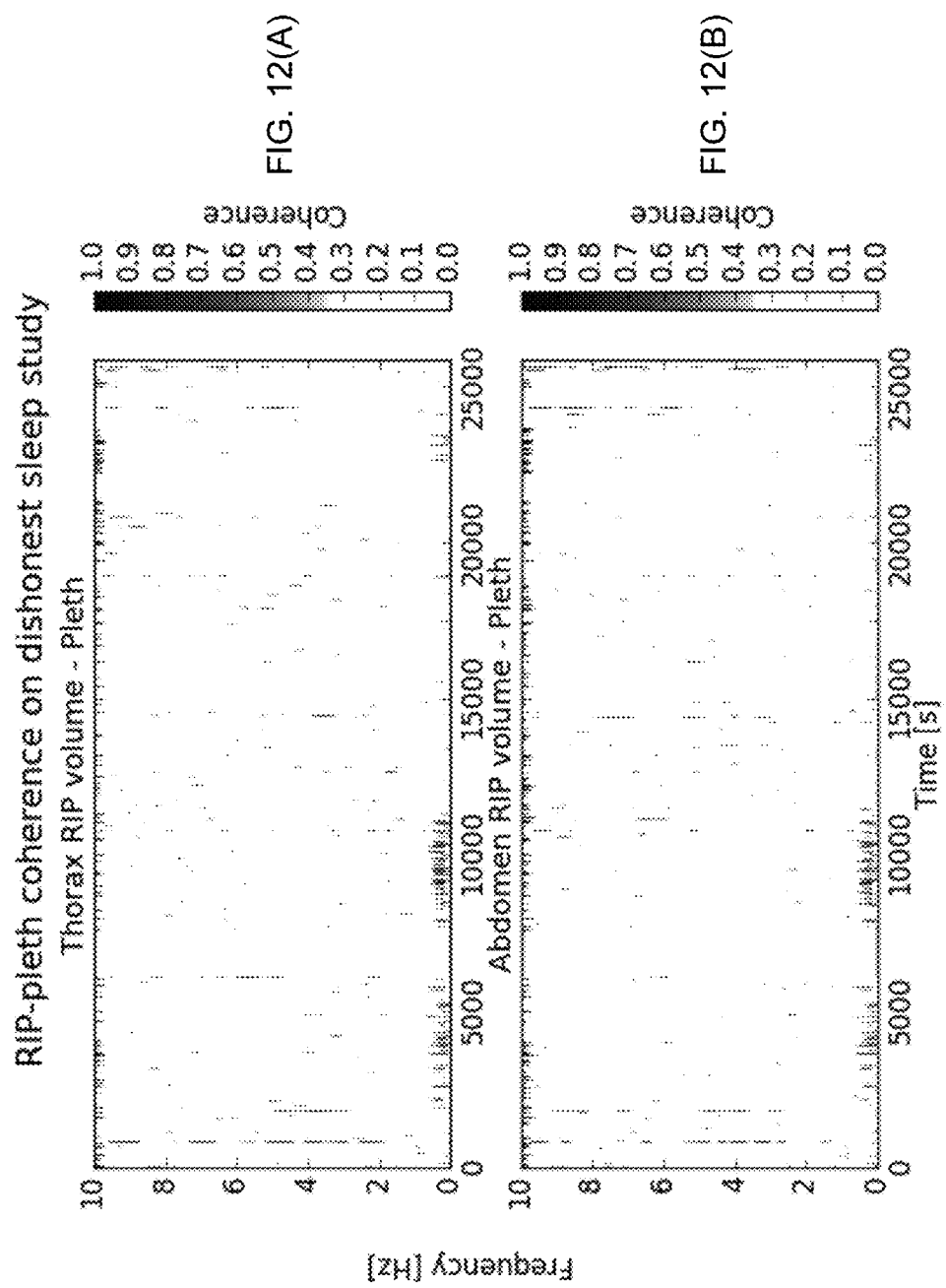

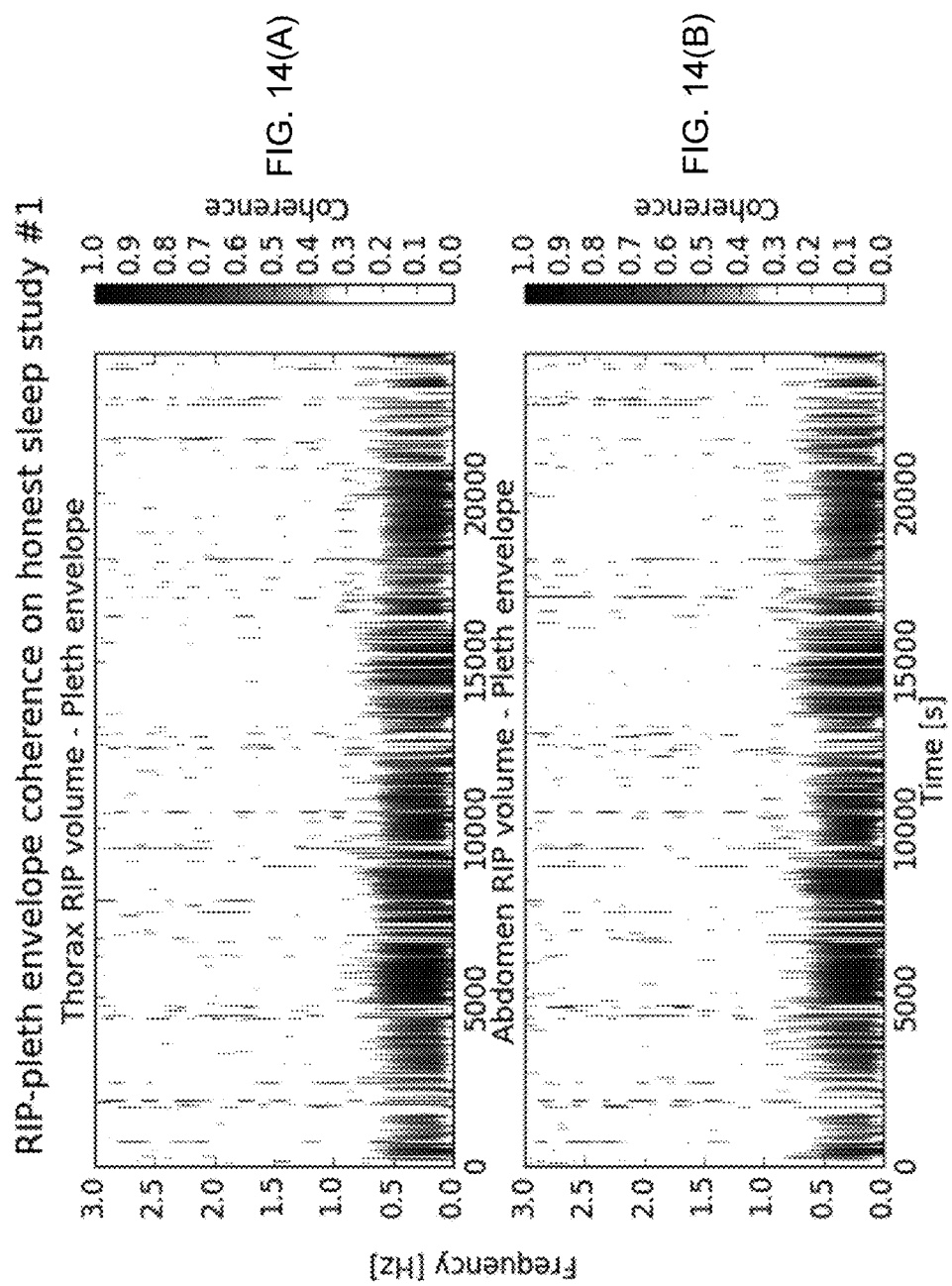

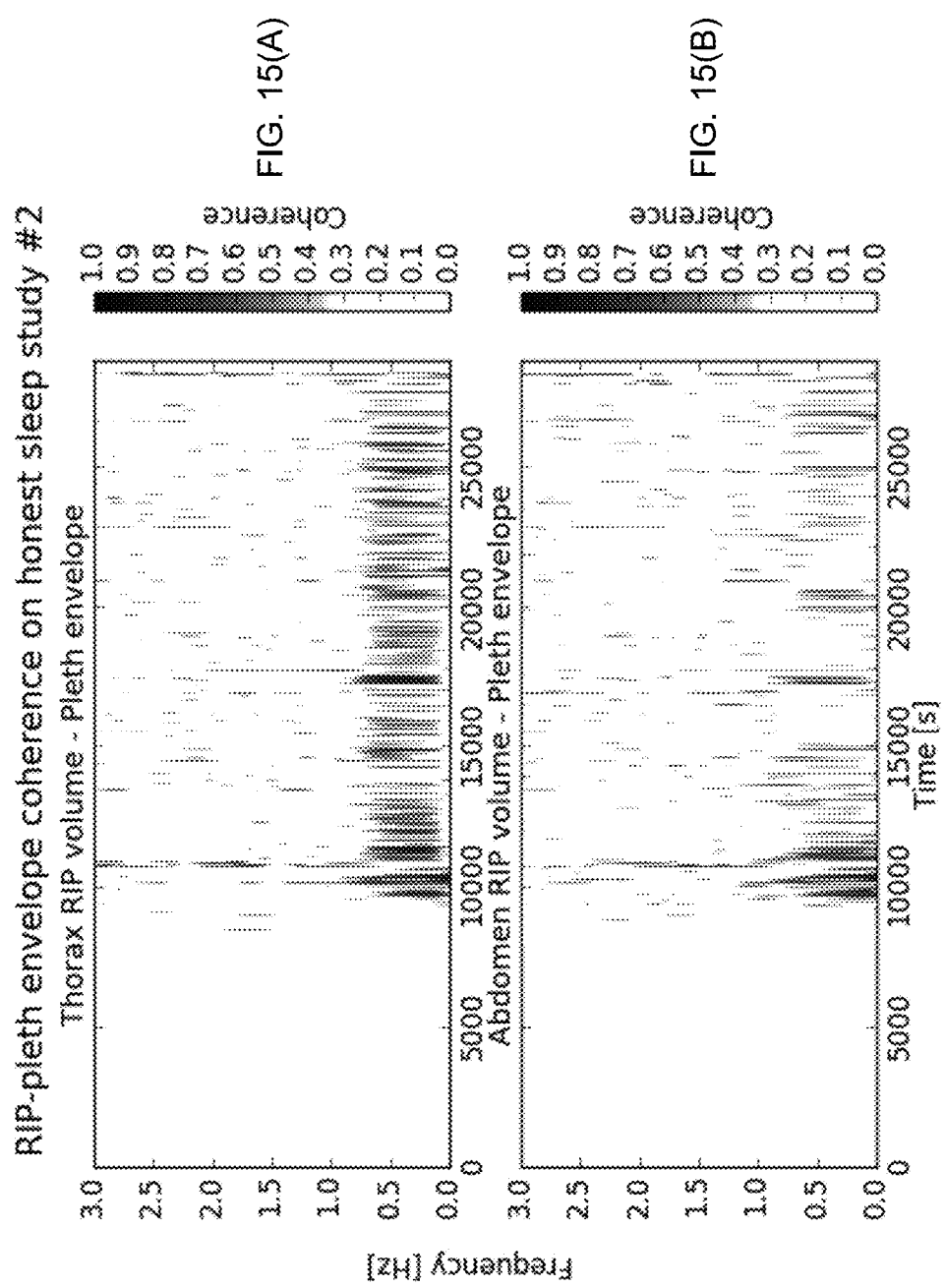

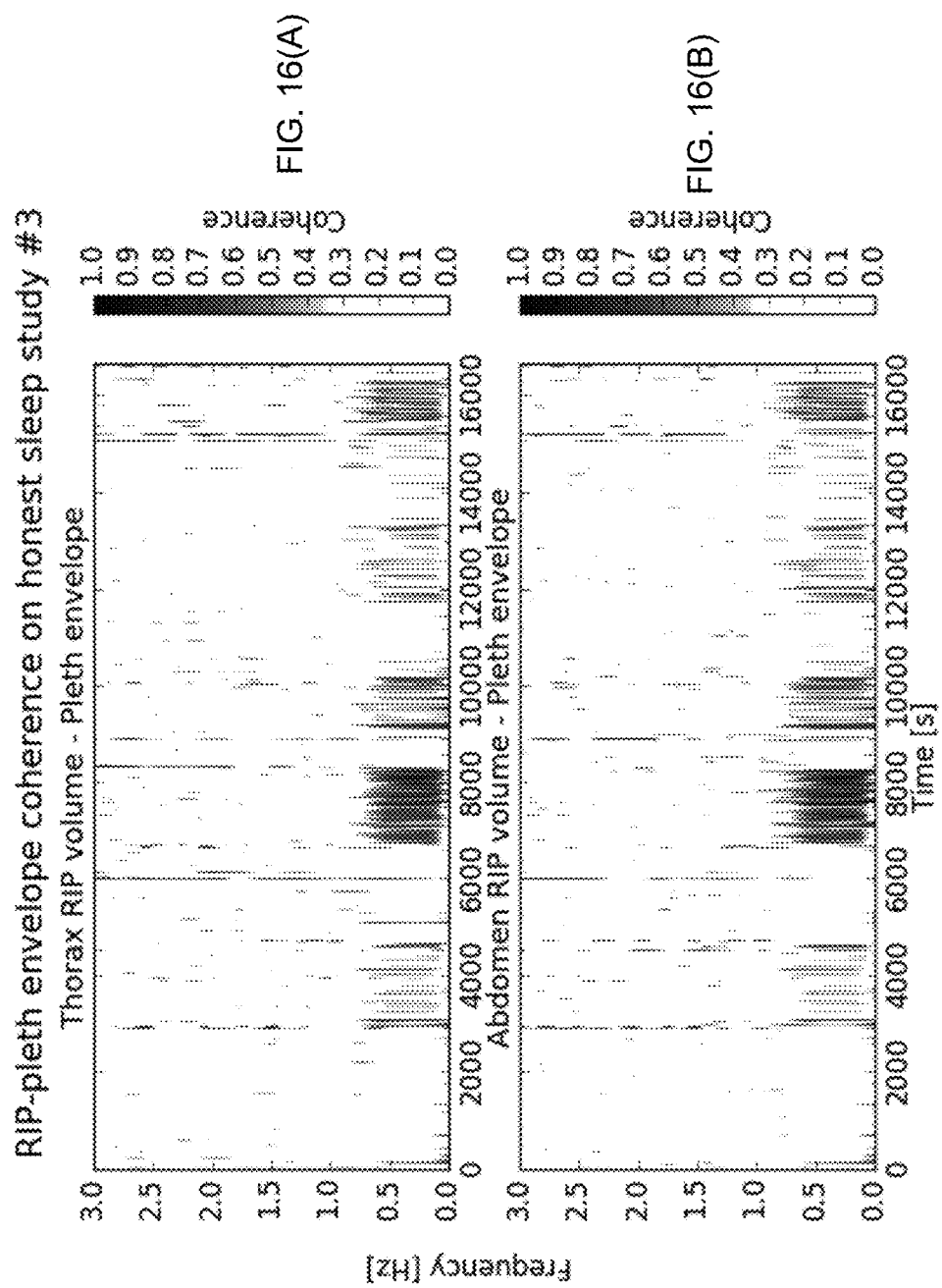

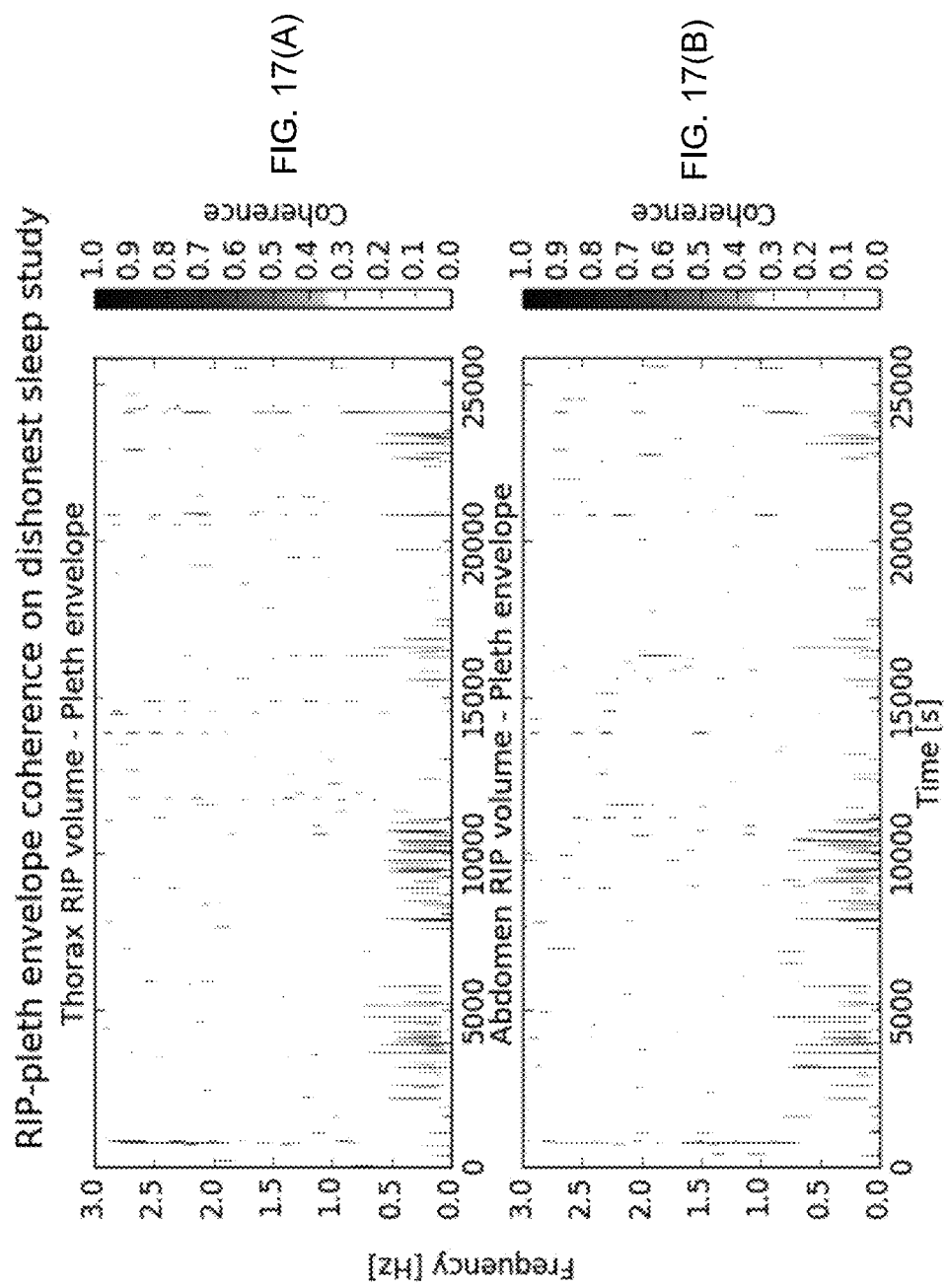

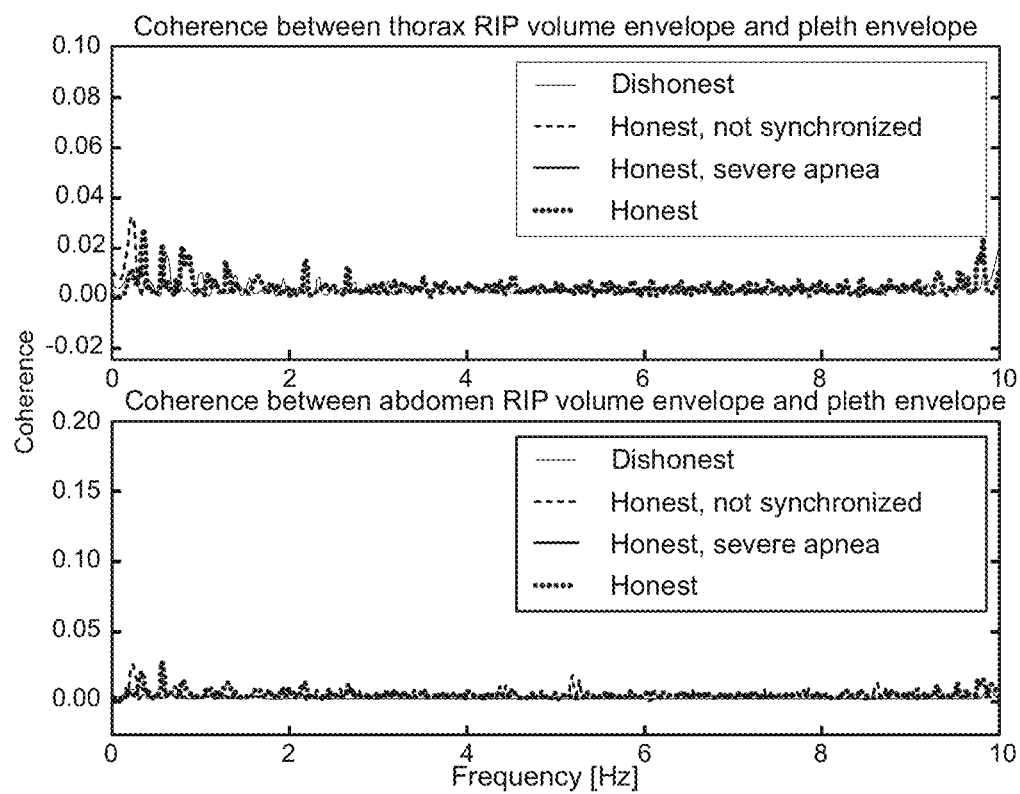

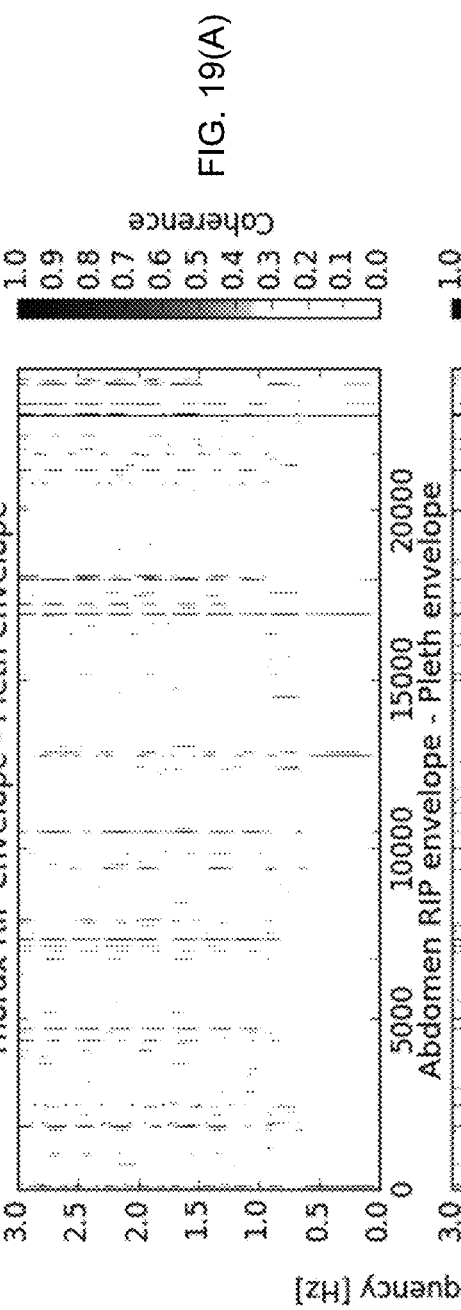
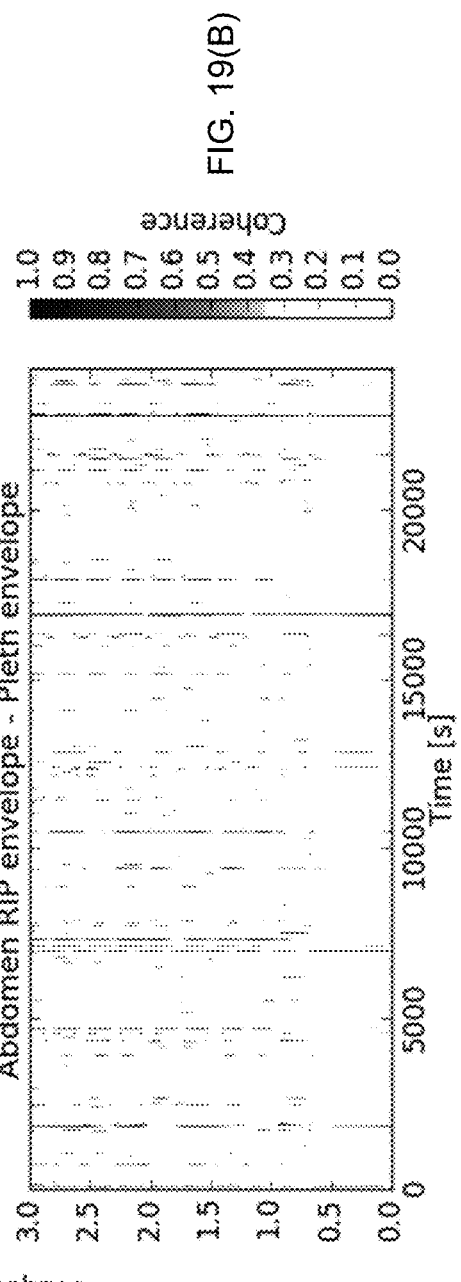
FIG. 19(A)
FIG. 19(B)

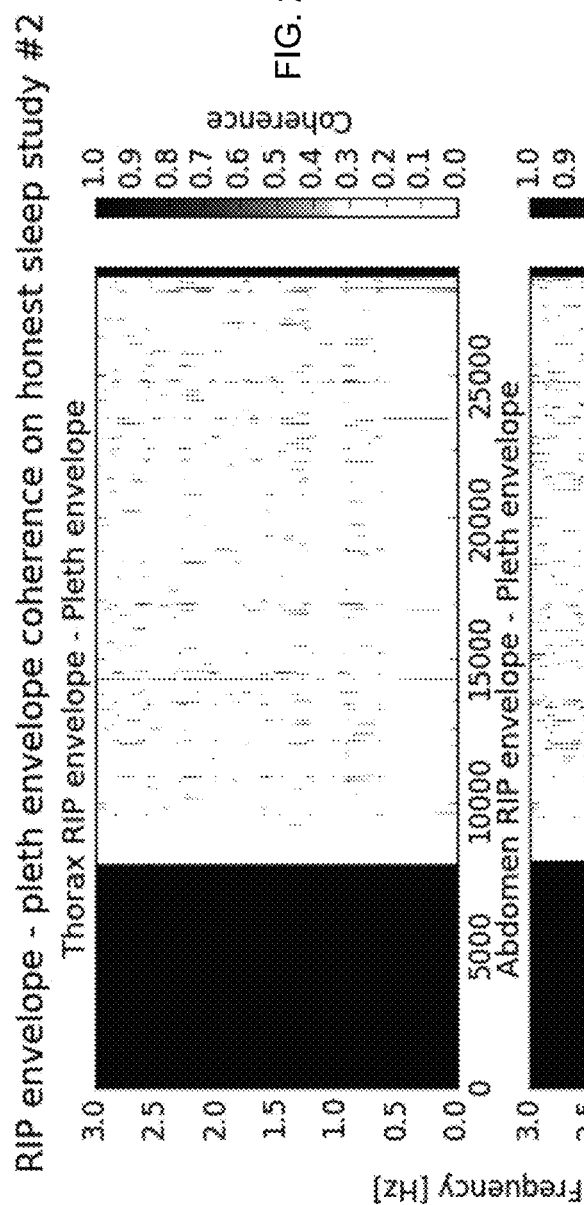
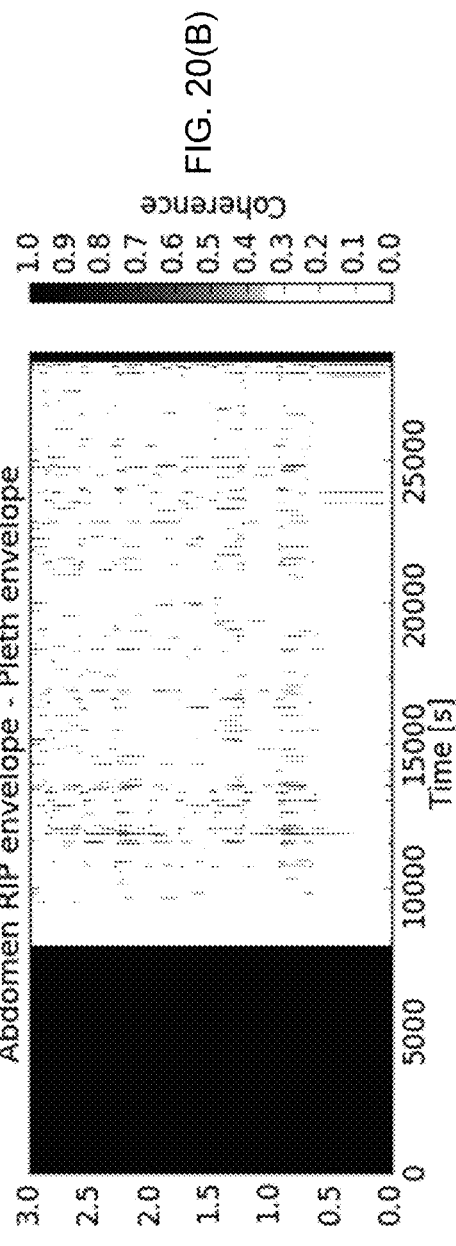

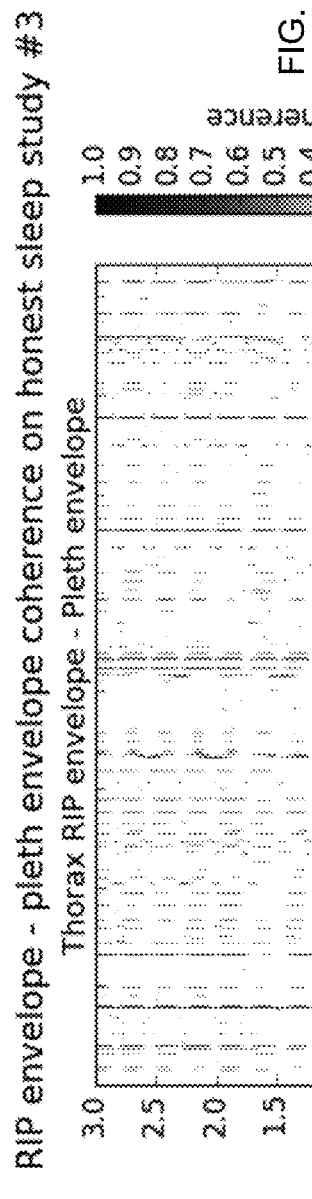
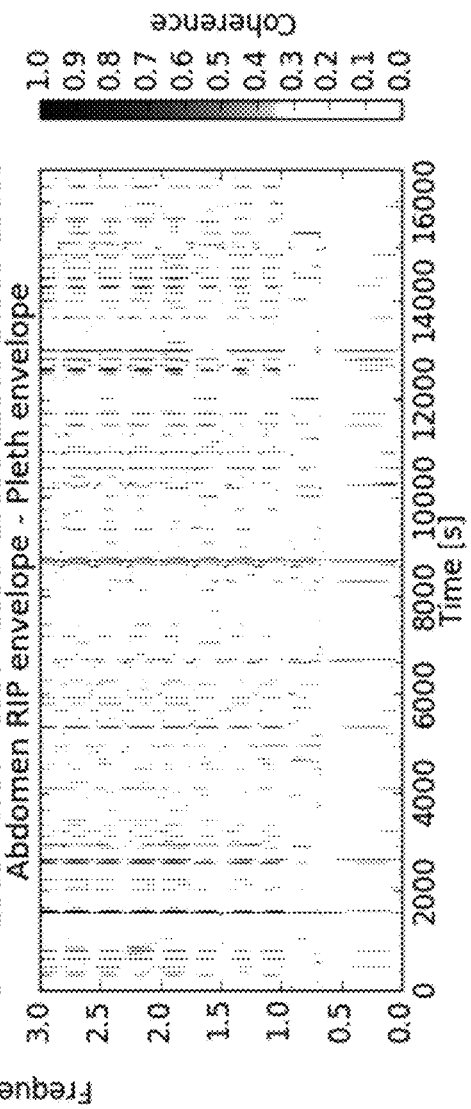
FIG. 21(A)
FIG. 21(B)

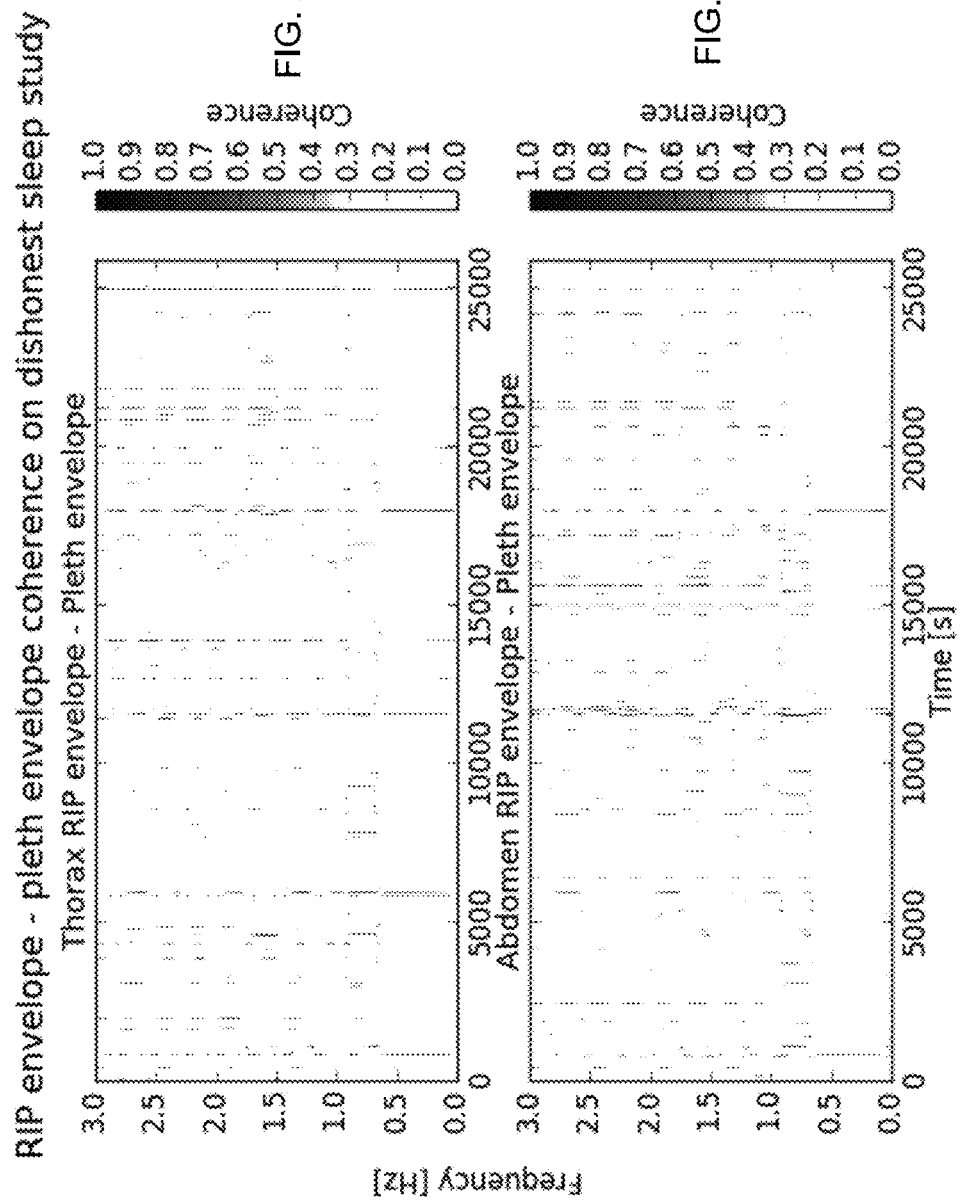

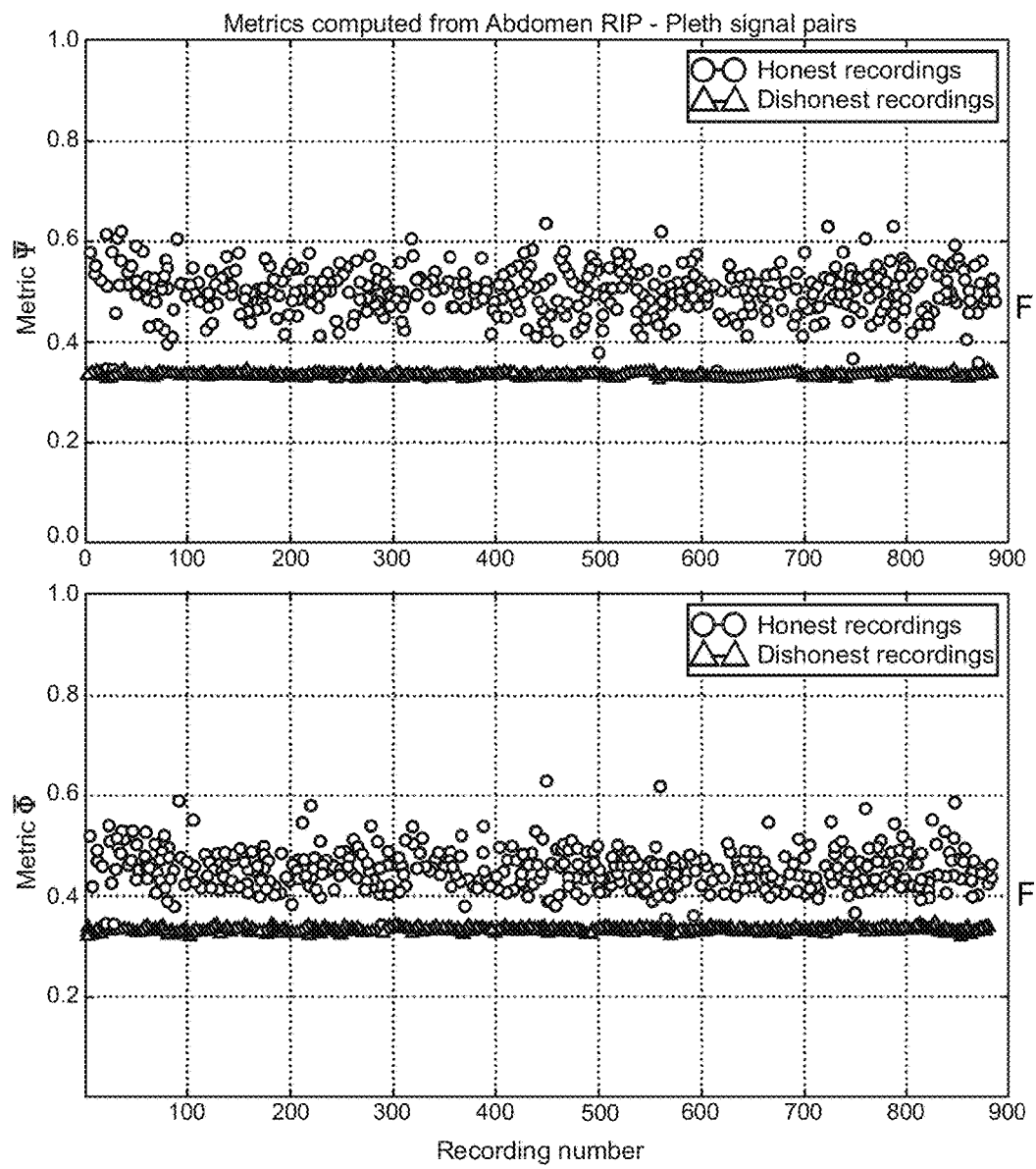

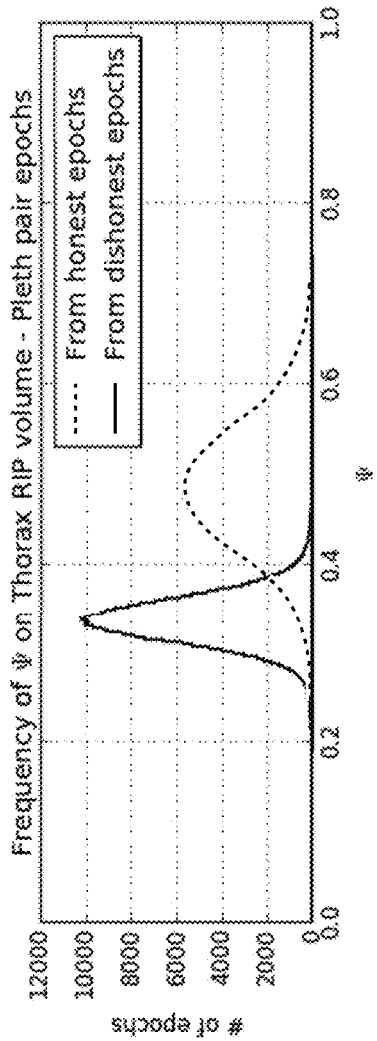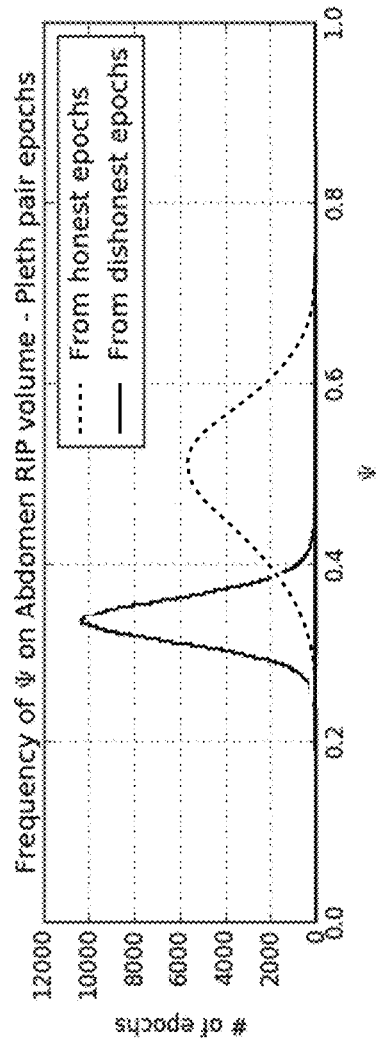
FIG. 41(A)
FIG. 41(B)

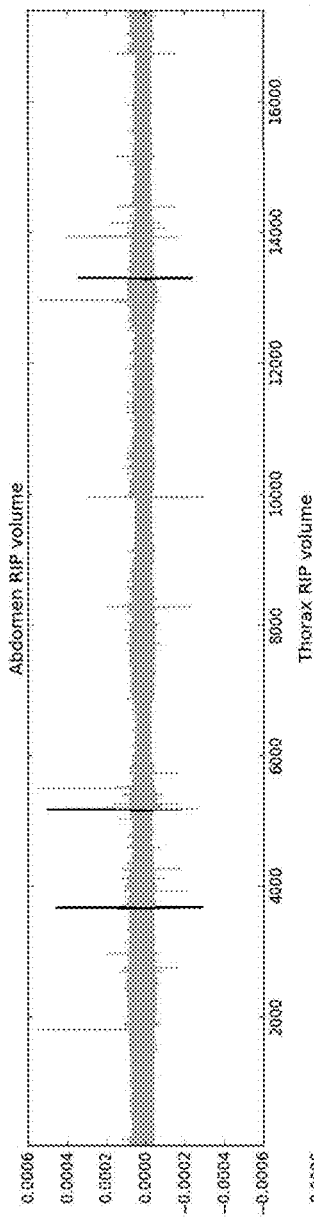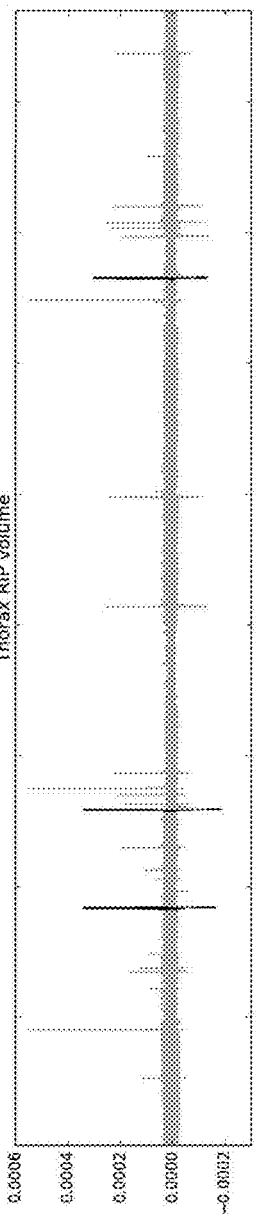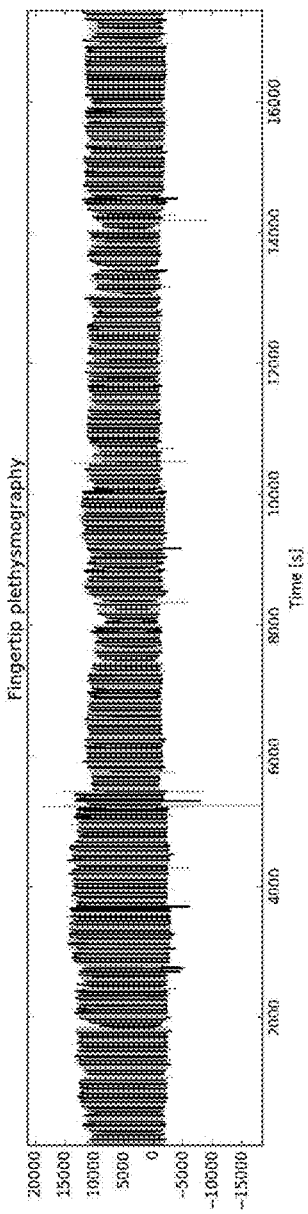

COHERENCE-BASED METHOD, APPARATUS, AND SYSTEM FOR IDENTIFYING CORRESPONDING SIGNALS OF A PHYSIOLOGICAL STUDY

This application claims the benefit of priority of U.S. Provisional Application No. 62/514,235, filed Jun. 2, 2017, the entire contents of which are herein incorporated by reference.

FIELD OF THE DISCLOSURE

The present disclosure relates to a method, apparatus, and system for determining whether two or more signals correspond, or in other words, originate from the same source, single person, or study subject, undergoing the measurement of the signals. The disclosure can be used as chain of custody or means of verification of the veracity of signals obtained in a physiological study. It can be used to determine whether a signal originating from an unknown source, single person, or study subject of a physiological study corresponds to a signal recorded in a known source, person, or study subject of the physiological study and thus can be used to assign such signals, originating from an unknown source, to the known source; or it can be used to determine whether a sensor of a signal of a physiological study assigned to a person or study subject was indeed placed on the person or study subject, was correctly placed, and indeed recorded the signal to be recorded.

RELATED ART

The objective of this disclosure is to determine whether two or more signals originate from, or in other words correspond to, a single source, person, or study subject.

Many physiological studies rely on measuring one or more signals using a single or multiple sensors. To improve the quality of the physiological study, it would be helpful to determine with high accuracy whether each signal of the physiological study is indeed obtained from the same person or subject. The signals of the physiological study contain information related to the subject. The signals can be termed physiological or have a physiological or environmental effect on the subject of the study, or can contain information relating to the environment, stimuli, or treatment(s) to which the subject is exposed. For example, the signal may include a measure of respiration, a heartbeat, brain activity, a measure of activity of the subject, ambient temperature or lighting of the environment of the subject, dosing of a medication, etc. Combining information from different signals can give a more complete picture of the physiological process under investigation whether it is a medical examination, a study of physiology, a measure of activity, health monitoring, or any other study where the physiology of a person or a study subject is of interest. To name a few examples, in medicine the combination of signals are commonly used to improve diagnosis, in research the measure of several signals can lead to new understanding of the underlying physiology, in sports an athlete's performance can be quantified by monitoring more than one signal, and in daily life the combination of commonly worn sensors such as a mobile phone, a smart watch, or an activity tracker can give a more complete picture of the persons or subjects activity and routine.

The sensors used to monitor the signals may be a part of one system or be a compilation of several systems, where sensors from a single or different manufacturers are used together to obtain the measurement. The sensors used can be medical or consumer products or a combination of the two. The sensor can communicate over a wire or wirelessly, or their signals can be collected by a third system where the signals level of correspondence is determined.

Additionally, in the increasing technology of the modern world, it is becoming more common that persons carry two or more unconnected body-worn sensors. These sensors are often built into devices that are carried every day, such as mobile phones and smart watches or can be specialized monitoring sensors, such as health monitors or medical sensors. Those sensors can send data over wireless links or recording their measurements for later review. Together the signals recorded by the multiple sensors can provide information of more value than the signals from individual sensors. It can, however, be essential to confirm that the signals are indeed all originated from the same person before reaching a conclusion based on multiple sensors. This is especially important in the medical field where a wrong diagnosis may lead to health and financial risks or reduced quality of life.

There are multiple scenarios in which it is of importance to determine whether two signals originate from the same source, person, or study subject.

One scenario is that two persons or subjects undergo a study in close proximity. One sensor in the study is a wireless sensor, for example, a pulse oximeter. For some reason the persons or subjects may accidently be given the wrong sensors or may accidently switch their sensors. In this scenario, the method in the disclosure can be used to identify which set of signals belong to which patient or subject. And instead of having lost two measurements from the study, the mistake can be corrected, and the signals can be correctly attributed to the correct person or subject. This may well become more important as the number of wireless sensors in hospitals and clinics increases.

A second scenario is that a person or a subject is assigned a set of sensors. Although it is assumed that all sensors work properly and have been placed properly, it is possible that a sensor malfunctions or is not placed properly. In this scenario, the method in the disclosure can be used to identify the malfunctioning or misplaced sensor.

Another scenario is that a person or study subject intentionally "cheats" in a physiological study. That is, as described below, some subjects may be incentivized to purposely provide signals obtained from two different subjects, or in other words "cheat." Such a physiological study could include a simple medical exam, a sleep study, a physical fitness exam, or monitoring within a hospital or clinic environment. It would helpful to be able to verify, or in other words, determine the veracity or correspondence, in such studies.

For example, some sleep studies are mandatory and are required to regulate the physical and mental capabilities of operators working in hazardous environments or with risky machinery or tools. This can be, for example, a truck driver that needs to prove that he is capable of driving the truck without risking the lives of others by falling asleep, etc. The practice is that various governmental agencies, such as departments of transportation (DOTs), insurance companies, or employers require the driver to prove that he does not have an untreated sleep disorder for him to operate the truck. The same goes for employees in nuclear power stations, air-traffic controllers, train operators, etc. Those employees therefore are incentivized to not to be diagnosed with a sleep disorder, such as obstructive sleep apnea syndrome (OSA), as they could lose their ability to work and be forced to undergo treatment that only has 50% compliance.

On the other hand, hospital facilities, such as a hospital of the U.S. Department of Veterans Affairs (VA), encounter a problem where patients may be incentivized to be diagnosed with a medical condition, for example, a sleep disorder. Often, if a person serves in the military and if the person has a disability that was developed during their time of service, when that person quits, the VA will pay that person a certain amount per month for the rest of their life. Such medical conditions, for example, a sleep disorder like OSA, are considered a disability and a person will receive a significant payment if the military releases them from service with that condition. It is therefore an incentive for those leaving the service to be diagnosed with a medical condition, such as a sleep disorder, such as OSA, before they are released so they will receive extra benefits for the rest of their lives.

For those cases, it important to prove that the study actually was performed on the person that was supposed to be analyzed. For example, it is important to prove, for example, that a home sleep test device was not moved deceptively from an unhealthy person that is supposed to be the subject of the study to a healthy person before the study starts, for example from the trucker to the trucker's wife/child or equivalent. Or in the case of a person trying to falsely claim a disability, such as the VA example above, from the person that is supposed to be the subject of the study (who is healthy) to a known OSA patient.

In the case of diagnosing a sleep disorder, such as sleep apnea, the sleep disorder may be diagnosed using both a measure of respiratory flow and blood oxygen saturation. In the past, it has been identified that fixing an oximeter to the wrist of the person using a hospital band or serial numbered wristband and making sure in the morning after that the wristband stayed on the whole night can ensure that the oximeter was used on the person to be examined. It remains, however, to prove that the other signals were recorded from the same person as the oximeter data. Currently, hospitals are suggested to record an additional electrocardiogram (ECG) channel. As each heart beat delivers both an ECG QRS-signal followed by a plethysmograph signal ("pleth" for short) in the oximeter, a technician can check that the two are in sync at a few occasions to verify that both are originated from the same source. This requires extra labor and monitoring costs, and requires extra channels to be recorded, adding burden to both the person undergoing the study and the technician examining the study outcome. Furthermore, manually looking whether the ECG and pleth signals are in sync at various times is prone to errors.

In a sleep study, as the respiratory flow and blood oxygen saturation is used to diagnose OSA, measuring the ECG does not ensure that the recorded flow signal originates from the same person as the ECG and pleth signals.

Two prior art references attempt to address the above issues: U.S. Pat. Nos. 8,679,012 and 6,993,378.

U.S. Pat. No. 8,679,012 describes a method of same-source-identifications. U.S. Pat. No. 8,679,012 is based on the idea to fix a biometric sensor to the body that actually confirms the person's identity, such as by having a fingerprint scanner or retina scanner as one of the signals of the recording. This patent also mentions the use of typical correlation such as between heart rate signal derived from ECG and heart rate from the Pulse Oximeter to confirm the same source. It does, however, not mention the use of coherence of non-correlating signals or secondary signals to do the trick.

U.S. Pat. No. 6,993,378 describes identifying a person based on bio-metric parameters, such as to check whether two voice recordings are originated from the same person. This is actually a very different application, as it is not related to medical diagnosis but security. And it is not related, necessarily, for identification of a same-source in real time. Rather, whether the signals are obtained from the same source is assessed by comparing signals recorded in different times.

SUMMARY

The present disclosure concerns a method, system, and apparatus for determining a correspondence of data obtained in a physiological study of a subject. The method includes extracting a first signal from the physiological study. A second signal from the physiological study is also extracted. The first signal and the second signal have been obtained by one or more biometric sensors. Data of the first signal and data of the second signal are stored on a memory storage device. A coherency value is determined between components of the extracted first signal and components of the extracted second signal. And the correspondence of the physiological study data is determined based on the determined coherency value.

A method for maintaining a chain of custody of data of a physiological study of a subject is also provided. This method includes providing to the subject a physiological study system, the physiological study system including one or more sensors configured to obtain physiological study data. The physiological study data includes a first signal from the physiological study and a second signal from the physiological study. Data of the first signal and data of the second signal are stored on a memory storage device. A confirmation is obtained that the one or more sensors have been placed on the subject. The method further includes receiving the physiological study data; and determining a correspondence of the data of the physiological study. The correspondence of the data of the physiological study is determined by extracting a first signal from the physiological study. A second signal from the physiological study is also extracted. The first signal and the second signal are obtained by one or more biometric sensors. Data of the first signal and data of the second signal are stored on a memory storage device. A coherency value is determined between components of the extracted first signal and components of the extracted second signal. And the correspondence of the physiological study data is determined based on the determined coherency value.

Additionally, a system to determine correspondence of data of a physiological study is provided. The system comprises one or more processors and one or more memory storages. The one or more memory storages have stored thereon the data of the physiological study. The one or more processors are configured to perform the following: extract a first signal from the physiological study; extract a second signal from the physiological study, the first signal and the second signal being obtained by one or more biometric sensors, and data of the first signal and data of the second signal being stored on the one or more memory storage device; determine a coherency value between components of the extracted first signal and components of the extracted second signal; and determine the correspondence of the physiological study data based on the determined coherency value.

And one or more computer-readable mediums are provided herein having stored thereon executable instructions that when executed by the one or more processors configure a computer system to perform at least the following: extract a first signal from the physiological study; extract a second signal from the physiological study, the first signal and the second signal being obtained by one or more biometric sensors, and data of the first signal and data of the second signal being stored on the one or more memory storage device; determine a coherency value between components of the extracted first signal and components of the extracted second signal; and determine the correspondence of the physiological study data based on the determined coherency value.

BRIEF DESCRIPTION OF THE DRAWINGS

FIGS. 9(A) and 9(B) show a coherence spectrogram of thorax and abdomen RIP volume and pleth signals, respectively, measured in an honest sleep study.

FIGS. 10(A) and 10(B) show a coherence spectrogram of thorax and abdomen RIP volume and pleth signals, respectively, measured in an honest sleep study where the patient suffers from severe apnea.

FIGS. 11(A) and 11(B) show a coherence spectrogram of thorax and abdomen RIP volume and pleth signals, respectively, measured in an honest sleep study where the RIP and pleth signals are not correctly synchronized.

FIGS. 12(A) and 12(B) show a coherence spectrogram of thorax and abdomen RIP volume and pleth signals, respectively, measured in a dishonest sleep study.

FIGS. 14(A) and 14(B) show a coherence spectrogram of thorax and abdomen RIP volume and pleth envelope signals, respectively, measured in an honest sleep study.

FIGS. 15(A) and 15(B) show a coherence spectrogram of thorax and abdomen RIP volume and pleth envelope signals, respectively, measured in an honest sleep study where the patient suffers from severe apnea.

FIGS. 16(A) and 16(B) show a coherence spectrogram of thorax and abdomen RIP volume and pleth envelope signals, respectively, measured in an honest sleep study where the RIP and pleth signals are not correctly synchronized.

FIGS. 17(A) and 17(B) show a coherence spectrogram of thorax and abdomen RIP volume and pleth envelope signals, respectively, measured in a dishonest sleep study.

FIGS. 18(A) and 18(B) show a coherence of thorax and abdomen RIP envelope and pleth envelope signals for four sleep studies.

FIGS. 19(A) and 19(B) show a coherence spectrogram of thorax and abdomen RIP volume envelope and pleth envelope signals, respectively, measured in an honest sleep study.

FIGS. 20(A) and 20(B) show a coherence spectrogram of thorax and abdomen RIP volume envelope and pleth envelope signals, respectively, measured in an honest sleep study where the patient suffers from severe apnea.

FIGS. 21(A) and 21(B) show a coherence spectrogram of thorax and abdomen RIP volume envelope and pleth envelope signals, respectively, measured in an honest sleep study where the RIP and pleth signals are not correctly synchronized.

FIGS. 22(A) and 22(B) show a coherence spectrogram of thorax and abdomen RIP volume envelope and pleth envelope signals, respectively, measured in a dishonest sleep study.

FIGS. 34(A) and 34(B) show metrics $\Psi$ and $\Phi$, respectively, for Abdomen RIP—pleth signal pairs from all the PSG and PG recordings.

FIGS. 41(A) and 41(B) show an epoch-wise histogram metric $\Psi$ for thorax and abdomen, respectively, and pleth signal pairs.

FIGS. 44(A), 44(B), and 44(C) show an outlier recording. Note the marked epochs are the epochs deemed of unacceptable quality.

DETAILED DESCRIPTION OF VARIOUS EMBODIMENTS

1—Introduction

A primary problem being resolved by this disclosure is providing a quantitative measure of whether two or more signals obtained from a physiological study are indicative of a common event (snoring, body movement, respiration, heartbeat, movement, sound, etc.) from the same and intended single subject of the study.

A way to compare the likelihood of two signals originating from the same source is to calculate the "correlation" between the two signals. Correlation is a measure of the similarity of the shape of two signals. If they "look alike," the correlation value will be high. If the signals do, however, have different shapes, a correlation is less useful in determining whether they originated from the same source. A method is therefore needed that can determine in a quantitative way whether two or more signals originated from the same source that is independent of the actual signal shape of the two or more signals. As an illustrative example, an ECG signal and a pleth signal originating from the same person have a very low correlation due to their very different shapes. The amplitude of one of the signals contains no information on the amplitude of the other.

The present disclosure addresses and solves the above-noted problems in a new way. Particularly, we start looking into the coherence of the signals involved. The coherence of two signals originating from a single source may be high even though their correlation may be low. In the illustrative example above the coherence between the ECG and pleth signals originating from the same person is very high.

The signals may be recorded by any body-worn device, such as a mobile device, smart watch, activity tracker, health, or medical sensors. One particular example includes signals obtained by a sleep-monitor device that records multiple signals coming from independent sensors. Such a sleep-monitor device could be, for example, a Nox T3 recorder from Nox Medical ehf.

Figure 46A:
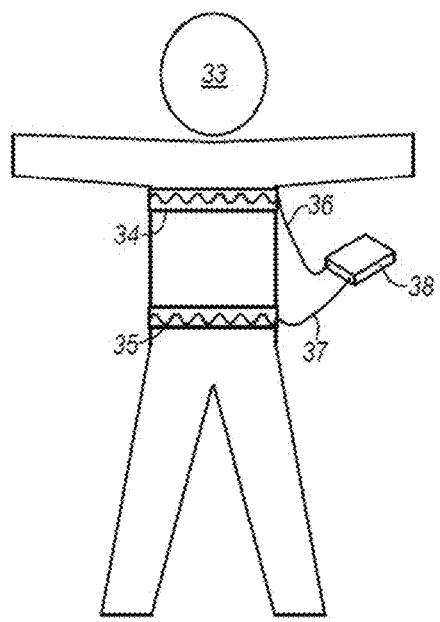
FIGS. 46(A) and 46(B) illustrate an example of respiratory inductance plethysmograph (RIP) belts, 46(A) shows an example of the wave-shaped conductors in the RIP belts, 46(B) shows the cross-sectional area of each belt, which is proportional to the measured inductance.
Figure 46B:
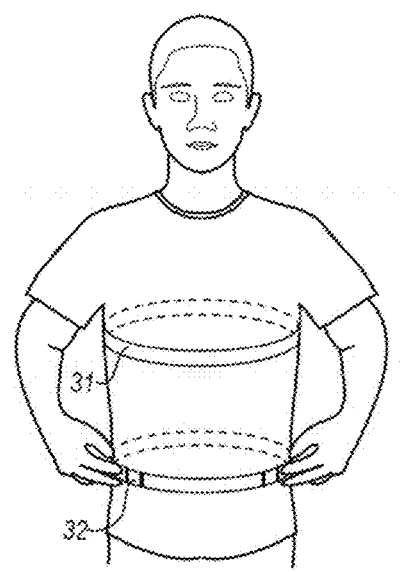

FIGS. 46(A) and 46(B) show a schematic of a sleep-monitor device based on Respiratory Inductive Plethysmography (RIP) to measure respiratory related areal changes. As shown in FIGS. 46(A) and 46(B), in a RIP-based device, stretchable belts 31, 32 that each contain a respective conductor 34, 35. When put on a subject 33, the conductors 34, 35 form a conductive loop that creates an inductance that is directly proportional to the absolute cross sectional area of the body part that is encircled by the loop. When such a belt is placed around the abdomen or thorax, the cross sectional area is modulated with the respiratory movements and therefore also the inductance of the belt. Conductors 34, 35 may be connected to signal-processing and storing device 38 by leads 36, 37. Signal-processing and storing device 38 may include a memory storage. By measuring the belt inductance, a value is obtained that is modulated directly proportional with the respiratory movements. RIP technology includes therefore an inductance measurement of conductive belts that encircle the thorax and abdomen of a subject.

The device may obtain signals that may originate from several sources and are mixed at various amplitudes in the recorded signal. For example, a measure of the thoracic respiratory movement may contain a mixture of signals of varying strengths. The primary signals may be caused by the respiratory movement, and secondary signals may be caused by the heart beating, and other possible sources of thoracic movement. The same applies to other signals of the physiological study. For example, a measure of the abdomen movement will contain a primary respiratory signal at high amplitude and secondary signals originating from the heart beating and other sources. Respiratory flow measured at the nose is also composed of the primary respiratory signal and the secondary signal originating from the heart. And the oximeter pleth signal is primarily a cardio signal but also contains a secondary signal of respiration through the modulation of the heart volume by the respiration. In such examples, as the primary component of the signals is not the same as the secondary signal(s) and their form may be very different from each other, they will not have a high correlation value and correlation will be an insufficient measure to determine whether the signals originate from the same person.

Coherence is, however, a method that overcomes the drawbacks of correlation for this purpose. Even if the signals compared do not share the same shape, they are generated, at least partially, by the same events (e.g., breathing, movement, cardio). They do therefore contain portions that are synchronized in time and have a fixed phase relationship. Coherence between two signals measures the synchronized portions of the signals even if the shapes of those portions do not correlate. The reason why coherence works this way is explained below.

First, coherence is calculated in the frequency domain, where the signal has been broken up into independent frequency components. Therefore, even if there is a primary signal involved, the secondary signal's frequency components are largely separated from the primary signal in the frequency domain.

Second, coherence is a measure of the phase relationship between waves of a single frequency. Signals triggered from the same origin will have the same fundamental frequency. And given the system they travel through is stationary in time, relative to the time it takes the signals to reach a detector, their phase relationship will be preserved resulting in high coherence regardless of the amplitude of the waves under investigation. For example, regarding a person's heart, the electrical signal, ECG, may trigger the heart beat and the resulting pulse in the finger may share the same fundamental frequency as the recorded ECG signal. Whether two signals originate from the same source and they contain the same fundamental frequency or harmonics, these components will be coherent given the system they travel through is stationary in time.

Coherence does actually measure the coupling strength with common harmonics in different signals and can therefore be used to determine whether the signals are partially coming from a common origin, practically independent of their signal shapes or whether they are correlated or not.

The method and system described herein may be based on any body-worn devices or sensors, non-medical or medical. For example, one particular example would be the Nox Medical's T3 device or another similar sleep study device. The method described herein may be used to detect whether measured signals of the physiological study originate from one subject may be based on the data provided by a Nox T3 device or another device recording signals of a physiological study such as respiration, pulse, electrocardiogram, or other almost periodic signals.

Furthermore, the method can be used for chain-of-custody purposes by confirming that a first sensor is attached to a person using any method, while confirming that other sensors are fastened to that same person by using the coherence between the first sensors signals and the other sensors. For example, the first sensor could be an oximeter fastened to the wrist of the patient using a hospital band or serial numbered wristband to confirm that it is worn by the patient during a sleep study and by making sure in the morning after the study that the wristband is intact it has been confirmed that the first sensor stayed on the patient for the whole night. As sleep apnea is diagnosed using both the oximeter data and simultaneously recorded flow, it may be shown with the method and system described herein, that the other signals were recorded from the same patient as the oximeter data.

The method and system disclosed herein is based on using coherence to test whether signals recorded from two or more distributed sensors originate from the same source. Further, a method is described of identifying the source by either fixing one of the sensors to the patient (as described above) or by using one of the bio-parameters recorded by the conventional sensors to identify the patient (for example, respiratory inductance plethysmography (RIP) belts can be used to evaluate the circumference of the patient wearing the belts and thereby if the circumference is known in advance for the patient, the data can only be falsified by finding a replacement-person with exactly the same circumference) or by proving by photograph or video that one or more of the sensors were attached to the correct person at a given time during the recording. And the method is used to confirm that the sensors were not moved from a first subject to a second subject before or after the confirmation photo or video was made.

As described above, often in physiological studies of a subject, two or more signals are obtained from, originate with, are produced by, or are related to a subject of the study. The subject may be, for example, a human subject, a patient, or an animal. As used herein, such a signal may be termed a signal of the physiological study. The term "signal" of the physiological study is used to describe a detection of an event, movement, activity, or occurrence relating to, originating from, or produced by the subject of the physiological study or of the environment of the subject.

A physiological event may include respiration, heartbeat, body movement, brain activity, skin conductance, muscle tone, eye movement, or sound, snoring, response to exterior stimulus or stimuli, such as lighting, sounds, or physical touching, coupled with said exterior stimulus or stimuli, or coupling between physiological events. Additionally, the above categories of physiological events may be further separated into more finely defined events. For example, a heartbeat may be broken down and considered to be a plurality of separate events, including the electrical activation of the heart, the pumping of the heart, and eventually the arrival of a pulse to the extremities. For example, if heart signals were examined as received and separated from RIP signals and a pulse signal were examined in oximeter, a common trigger could be the electrical activation of the heart which would lead to downstream events such as the heart pumping and the generation of a pulse.

Signals of the physiological study may include, for example, but are not limited to: an electrocardiogram (ECG), a plethysmograph signal, respiratory inductance plethysmography (RIP), electroencephalography (EEG), electrooculography (EOG), electronystagmography (ENG), or electromyography (EMG). Further, signals of the physiological study may include a detection of snoring, swallowing, coughing, body movement, respiration, heartbeat, movement, brain activity, digestion, temperature changes, perspiration, a response or responses of the subject to a stimulus or environment, or other bodily activities. Further, a signal of a physiological study could be related to an environmental activity or condition during the physiological study, or an event, condition, or treatment to which the subject is exposed to or affected by during the study. The signal of the physiological study may be obtained with one or more biosensors or sensors, such as light sensors, cameras, accelerometers, microphones, or temperature detectors, or some other detector configured to gather the signal in the physiological study.

To improve the quality of the physiological study, it would be helpful to determine with high accuracy whether each signal of the physiological study is indeed obtained from the same subject. Thus, an object of the method and systems disclosed herein is to determine whether two signals of the physiological study originate from or in other words correspond to the same source, person, patient, or subject.

There are multiple scenarios in which this would be useful, that is, where the two sensors are placed on two patients.

One scenario is that a patient intentionally cheats in a physiological study. Such a physiological study could include a simple medical exam, a sleep study, or a physical fitness exam, or monitoring, at home, within a hospital or clinic environment, or in some other environment.

Further, in some physiological studies, as described below, some subjects may be incentivized to purposely provide signals obtained from two different subjects, or in other words "cheat." Using the method described herein, it become possible to verify, or determine the correspondence, in such studies.

Another scenario is that two patients undergo a study in close proximity. One sensor in the study may be a wireless sensor, for example, a pulse oximeter. For some reason the patients may accidently be given the wrong sensors or the subjects accidently switch their sensors. In this scenario, the method in the disclosure can be used to identify which set of signals belong to which patient. And instead of having lost two measurements in the study, the mistake can be corrected, and the signals can be attributed to the correct subject. This may well become more important as the number of wireless sensors in hospitals and clinics increases.

Outlined below are various scenarios or applications in which it would be helpful to determine a veracity, correspondence, or quality of two signals obtained in a physiological study would be helpful.

1.1 Ensuring Quality of Signals Coming from Sensors Placed on a Person

During a measurement of signals of a physiological study, more than one sensor may be placed on a patient. The coherence between signals from two different sensors can be used to determine that sensors attached to the patient measure a signal of a physiological study from the patient. The method can be used to measure how reliable the measured signals are. In a first example, during a sleep measurement the coherence between signals from an ECG and a pulse oximeter can be used to determine whether both the ECG and pulse oximeter are correctly measuring the heart beating.

In a second example, during a Holter ECG monitoring, coherence between two different leads in the Holter measurement can be used to determine whether both leads, which are connected to the patient, are correctly measuring heart activity.

In a third example, during a sleep study, the coherence between an audio signal and a respiratory signal measured by RIP belts or another respiratory sensor can be used to determine whether both sensors are measuring signals originated from respiration. Such as if a person is undergoing a sleep study where snoring is measured by an audio sensor and respiratory movements by RIP belts, it is important to determine whether the sounds are originated from the person respiration or from another source.

In a fourth example, during recordings of daytime activities, such as by a mobile phone and a smartwatch, the coherence between the activity signals can be used to determine whether both are originate from the same person.

1.2 Detecting Whether Signals Recorded with Sensors not Directly Placed on a Person Originate from the Person During a sleep study the method described herein can be used to determine the origin of signals measured by sensors not directly attached to a patient.

In a first example, in a sleep study, the patient undergoing the study may share a bedroom with a second person. The coherence between an audio signal and a respiratory signal measured by RIP belts or another respiratory sensor can be used to determine whether sounds of snoring captured by an audio recording originate from the patient undergoing the sleep study or the second person sleeping in the same room as the patient.

In a second example, during a sleep study, a patient may sleep in an environment where external noise is detected by the audio measurement the coherence between the audio signal and the respiratory signal measured by RIP belts or another respiratory sensor originate from the patient respiration or the external noise source 1.3 Detecting Whether Sensors Assigned to a Person Measure Biological Signals from that Person During a measurement of signals of a physiological study, wireless sensors may be used on a patient. In a first example, the coherence between signals measured by two wireless sensors can be used to determine whether both sensors have been correctly placed on the patient undergoing the study.

In a second example, if it is determined that all of the sensors used in the physiological study do record signal of the study. However, a sensor assumed to be placed on a first person is for some reason placed on a second person. According to the method and system described herein, the coherence between sensors on the first person can be used to determine which sensors are truly measuring signals from the first person. And the coherence between the sensors on the second person can be used to determine which sensors are measuring signals from the second person.

In a third example, in the case two persons undergo a physiological measurement and mix a sensor as mentioned in the second example, the coherence between the signals from the sensors assigned to the first person and the second person can be used to determine which sensors were placed on the first person and which sensors were placed on the second person. Instead of the study being invalid, the sensors can be reassigned to each person and the study can be salvaged.

1.4 Detecting Whether a Sensor was Connected to a Person

During a measurement of signals of a physiological study, more than one sensor may be expected to be placed on a patient. But it may not be known whether the sensors were placed on the patient or not, or are placed correctly. The coherence between signals can be used to identify sensors that were not properly placed and thus are not measuring signals.

1.5 Detecting Artifacts in a Signal

During a measurement of signals of a physiological study, a sensor designed to measure one physiological process or event may detect more than one process or event. This can influence the analysis of the measured signals. In a first example, during a sleep study, an ECG or pulse signal may be measured as well as an EMG signal obtained, for example, from the leg to detect periodic limb movement. The coherence between the two signals can be used to determine whether there is a cardiac artifact in the EMG signal, which could be interpreted as limb movements during signal analysis.

In a second example, during a sleep study an ECG or pulse signal may be measured as well as respiratory movements using RIP belts. Coherence between the two signals can be used to determine whether there is a cardiac artifact in the respiratory movement signal.

In a third example, during a study of EEG, an EEG signal is measured and an ECG or a pulse signal is measured. The coherence between the signals can be used to determine whether there is a cardiac artifact in the EEG signal.

In a fourth example, during an EEG study, brain activity may be measured using EEG and eye movements are tracked for example using EOG. The coherence between the EEG signal and EOG signal can be used to determine whether there is eye movement artifact in the EEG signal.

1.6 Sleep Studies

Sleep studies are used to obtain data relating to body activity of a subject during sleep. Sleep studies are particularly useful in diagnosing sleep disorders, such as sleep apnea syndrome. Various techniques may be used to obtain signals of relevant data in a sleep study, including, but not limited to, Respiratory Inductance Plethysmography (RIP), Electroencephalography (EEG), Electrocardiography (ECG), Electrooculography (EOG), Electronystagmography (ENG), and Electromyography (EMG). Relating to such techniques for obtaining, calibrating, and analysis these signals, U.S. Pat. Nos. 8,025,539, 9,059,532, and 9,192,316, U.S. Pub. No. 2015/0126879, U.S. patent application Ser. No. 14/535,093 filed Nov. 6, 2014, U.S. patent application Ser. No. 15/680,910 filed Aug. 18, 2017, U.S. Provisional Patent Application No. 62/555,992 filed Sep. 8, 2017, and U.S. Provisional Patent Application No. 62/575,139 filed Oct. 20, 2017, each of which are incorporated herein by reference in their entirety.

As described in the background section, some patients or subjects may seek to cheat in their sleep studies measured with take-home sleep study equipment. The reasons can be numerous but some of them are the following:

a truck driver with sleep apnea could lose his driver's license if he does not seek the possibly expensive treatment; or an army veteran who developed sleep apnea while in service could get on disability.

Usually, when a patient is at risk for cheating in a sleep study, an oximeter is attached to the patient in a way that he cannot take it off. In this case, the oximeter may be wireless. To combat this, those who cheat in sleep studies usually employ the following methods:

those wanting to avoid diagnosis of sleep apnea sleep with the oximeter while a person that does not have sleep apnea (often the spouse) sleeps with the rest of the sleep study equipment; or those wanting to be misdiagnosed may sleep with the oximeter while a person that is known to have sleep apnea sleeps with the rest of the sleep study equipment.

One object of this disclosure is to describe how a statistic called coherence may be used for determining whether a patient cheated in his sleep study in the following ways: (1) the patient had the oximeter attached; or (2) another person wore the remaining sleep study equipment (including RIP belts and often an ECG sensor). The plethysmography signal can originate from any pulse meter. For example, the plethysmography signal can originate from the fingertip, however, other appendages, such as the toes, foot, or hand, or other locations such as earlobe or forehead can also be used.

Thus, the method of this disclosure may use coherence as a measure of the probability that two signals of a physiological study originate from the same person or subject. The signals of the physiological study could be, for example, RIP signals and oximeter pleth signal. The signals could also be an ECG signal collected with a wireless sensor on the patient and a pulse plethysmography signal or a respiratory signal.

The coherence statistic may be used for comparing the plethysmography (pleth) signal from the oximeter to one of the signals measured, for example, respiration or ECG, from the rest of the sleep study equipment.

1.7 Remote Sleep Studies

In another embodiment, a chain of custody of the sleep data is obtained remotely, for example, through the mail. In this embodiment, a sleep study device, for example, a Nox T3 device or another sleep study obtaining system is sent by mail from, for example, a sleep study administrator or agency to a subject.

According to an embodiment, the patient receives the sleep study device or system, which may include one or more different sensors. The sleep study device or system may also include a device, including a camera, that can communicate over a wireless interface with the one or more sensors. One of the sensors may be capable of monitoring whether it is removed from the patient after being attached to him (locked to the patient). For example, the sleep study device, such as the Nox T3 device, would be able to detect or determine whether the device has been removed from the patient once it has been attached. The sleep study device, such as the Nox T3 device, is attached to the patient with, for example, RIP belts, and the device would record continuously if the belts were disconnected. This same sensor may have a display or other means of a visual signal generator.

The subject would then follow the directions of the system and put on the sensors. The sleep study device, with, for example, the camera instructs the "locked" sensor to show a code on the display as a "confirmation code."

The subject is then instructed to be seen on the camera and a photo or a video is taken showing both the face of the subject and the code on the display. In another embodiment, the subject is also instructed to show his ID card for a photo.

From this time forward the locked sensor confirms that it has not been removed from the subject and the coherence confirms that the other sensors are on the same subject.

In another embodiment, a simpler "manual" version may not require a wireless connection with the camera but could be done over a video call.

After the device is on the subject and "locked," the subject is called by video for a chain of custody (COC) confirmation. When the subject appears in the video he is requested to press a button or otherwise activate the sensor with the display, if it is not already active. The display shows a confirmation code on the display that can be seen on the video and may be stored with the recording. The operator may log the code to confirm the identification and the time of the identification. The "locked" sensor then confirms that it was not removed, and if more than one sensor is used, coherence with other sensor signals is used to determine that the other sensors are all on the same person. When the recording is reviewed the code stored is compared with the code logged by the operator.

In these embodiments, the display could be a row of light emitting diodes showing a randomized pattern as a confirmation code, a regular display or any other means of displaying a visual code.

2—Methods and Experiments Supporting the Method

A proof of concept was performed for testing the effectiveness of the method when used on real data received from a sleep study. Although the proof of concept is described in detail, including an implementation of the method and a discussion of useful metrics, the description does not exclude other possible implementations of the method or other metrics. Other implementations may include using different pairs of signals, using different durations of the measured signals in the method, scaling of the measured coherence with the power of one or both of the two signals under investigation, or scaling of the measured coherence with the two signals cross power density. Other metrics may include a measure of coherence length or coherence duration, that is the maximum length of segments from the two signals under investigation which results in a coherence value above a certain threshold, the coherence at certain frequency bands can be of interest, or the ratio of coherence between two different frequency bands. Furthermore, specific values used in the proof of concept are specific to this implementation and may change greatly, by many orders of magnitude, depending on the implementation and signal sources.

The sleep study data used was both provided by the University Hospital of Iceland, hereby referred to as the "LSH dataset" and recorded by Nox Medical ehf employees for testing the concept. The coherence method was implemented using the Matlab™ signal processing software, Python™, and other mathematical software. The recorded signals were mixed up between recordings and the method was tested to determine how accurately the method would work to determine whether a recording contained a signal that did not originate from the same person. In the text below, this implementation of the method is described.

First, the data and the code will be discussed. The coherence statistic will be introduced alongside other methods used in this disclosure. The coherence for each signal pair will be examined on specific sleep study recordings. Metrics will be proposed and analyzed. A cheat detection test will be proposed based on analyzed metrics. The cheat detection test's results of the LSH dataset will be examined. Lastly, the significance of the results of the metrics will be discussed.

2.1 Recordings Made for Testing the Concept

The data used for exploring the coherence statistic and the metrics introduced in this disclosure consisted of three partial sleep recordings performed by Nox and one full polysomnography (PSG) recording. Recordings 1 to 3 were gathered by the Nox research team and recording 4 came from the LSH dataset.

The first recording was fraudulent, or in other words, was based on "cheating." That is, the one subject only slept with an oximeter while the subject's spouse slept with the rest of the sensors and recorder (including the signals frontal EEG, ECG, EMG, RIP belts, and cannula).

The second recording was honest. That is, the subject did not cheat during the sleep study and wore all the sensors and recorder himself.

The third recording was honest. That is, the subject did not cheat during the sleep study. Also, this subject suffered from severe sleep apnea, which is apparent in the recording.

The forth recording was honest, but due to the equipment used, the recorded signals were not properly synchronized. That is, the RIP and pleth signals are not properly synchronized in time. Note that the RIP signals in this recording were sampled at 25 Hz opposed to the 200 Hz sampling rate in the first three recordings.

2.2 the LSH Dataset

The data used for building the methods introduced in this disclosure included 778 polygraph (PG) recordings and 113 polysomnography (PSG) recordings from the University Hospital of Iceland (the LSH dataset). Note that the recordings in the LSH dataset were not properly synchronized. That is, the pleth signals were not properly synchronized in time with the other signals. Also, note that the RIP signals in the LSH recordings were sampled at 20-25 Hz. As coherence is based on synchronized events in more than one signal, the lack of synchronization was expected to reduce the efficiency of the method.

3—Tools

The mathematical and signal processing tools used for exploring the coherence statistic and building our cheat detection metrics will be introduced in this section.

3.1 Coherence

As described above, coherence is the main mathematical method used in this method. A mathematical definition of coherence is listed below.

The coherence between signals x(t) and y(t) may be defined as:

$$C_{xy}(f) = \frac{|G_{xy}(f)|^2}{G_{xx}(f)G_{yy}(f)}$$

where $G_{xy}(f)$ is the cross spectral density between x(t) and y(t), $G_{xx}(f)$ is the autospectral density of x(t) and $G_{yy}(f)$ is the autospectral density of y(t).

We have $0 \leq C_{xy}(f) \leq 1$, and the magnitude of $C_{xy}(f)$ can be thought of as the strength of the connection between the f frequency components in x(t) and y(t).

3.2 Coherence Spectrogram

A coherence spectrogram is a method to represent coherence as an image.

Coherence spectrogram can be looked at as a heatmap, where each point (t, f) shows the coherence between two signals at frequency f during time t. A plot of this type of heatmap, provided herein as grayscale, was used for presenting the results of this disclosure.

3.3 Envelope Detectors

The envelope signal of an oscillating signal, such as a sine wave, where the "amplitude" of the sine wave changes slowly from one wave to the next is indeed the "amplitude." What is commonly referred to as the oscillating signal is "amplitude modulated" by the slow changing signal. Envelope detectors are therefore used to determine the amplitude of an amplitude modulated signal. Finding the envelope of a signal can be an important pre-processing method before calculating its coherence to another signal.

More generally, let us say that we are given a signal y(t) which is a multiple of a low-frequency signal m(t) and a high frequency signal c(t). We also assume that the frequency spectra of m(t) and c(t) do not overlap.

Envelope detection involves isolating m(t) when you are only given y(t). The term m(t) is referred to as the envelope of y(t) since it is visually the envelope of y(t). An example can be seen in FIG. 1.

Figure 1:
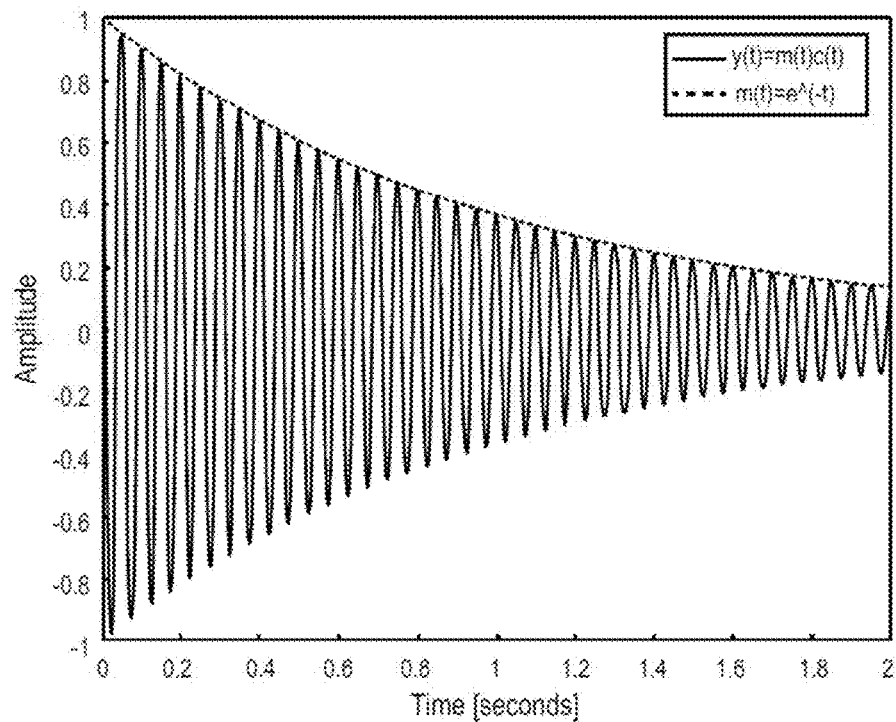
FIG. 1 shows an example of a modulated signal y(t) and its envelope m(t).

FIG. 1 shows an example of a modulated signal y(t) and its envelope m(t), particularly $y(t) = e^{-t} \cos(2\pi \ast 20t)$ and its envelope $m(t) = e^{-t} u(t)$. In the case of FIG. 1, m(t) was chosen to be the low-frequency signal $e^{-t} u(t)$ where u(t) is the Heaviside step function. c(t) was chosen to be the high frequency, relative to m(t), cosine of frequency 20 Hz.

Note that the spectra of m(t) and c(t) overlap. However, the spectrum of m(t) is very attenuated for high frequencies. It loses half of its power at $$\frac{1}{2\pi} \text{Hz}$$

so we can relax the condition that the spectra of m(t) and c(t) must not overlap completely if one of the signals produces insignificant contribution to the spectra overlap compared to the other.

3.3.1 Envelope Detection Using Peaks (PE Method)

In this subsection, a method for estimating the envelope of y(t), with only y(t) given, will be explored. As can be seen in FIG. 1, it seems like it could be sufficient to find all the peaks in y(t) and interpolate polynomials between them to estimate the envelope. This subsection will introduce a method that does that. The method works as the following:

Detect all peaks in y(t) using a detect_peaks function, for example, the detect_peaks function written by Marcus Duarte. (Relating to the detect_peaks function, reference is made to O. E. P. P. e. a. Jones E, "SciPy: Open Source Scientifc Tools for Python," 2001, which is incorporated herein by reference in its entirety: and Interpolate the peaks with a B-spline interpolation. (Relating to B-spline interpolation, reference is made to M.

Duarte, "Detect peaks in data based on their amplitude and other features," 2014, which is incorporated herein by reference in its entirety.

3.3.1.1 Envelope of RIP Volume Signals

To find the envelope of a RIP volume signal, we proposed using the PE method. We also proposed the following condition settings for the peak finder:

The minimum peak height is zero; and
The minimum distance between peaks is 2 seconds.

3.3.1.2 Envelope of Fingertip Plethysmography Signals

To find the envelope of a pleth signal, we proposed using the PE method introduced in this section. We proposed the following condition settings for the peak finder (however, these condition settings could be modified):

The minimum peak height is 4000; and
The minimum distance between peaks is 0.3 seconds.

We also proposed that the peaks detected with the peak finder (peak_detect) are passed through a heart variability correction test before the envelope is interpolated. This heart variability correction test is described by a published disclosure on signal quality indices for electrocardiograms and photoplethysmograms and works as the following. (See C. e. a. Orphanidou, "Signal-Quality Indices for the Electrocardiogram and Photoplethysmogram: Derivation and Applications to Wireless Monitoring," IEEE Journal of Biomedical and Health Informatics, vol. 19, no. 3, pp. 832-838, 2014, which is incorporated herein by reference in its entirety.)

In an embodiment, we assume that y[n] is our fingertip plethysmography signal sampled at a sampling frequency of $f_s$ and I is a vector containing all the peaks that our peak detector (peak_detect) detected. The heart variability correction test works as the following:

1. y[n] is split into 10 second epochs $y_i[n]:=y[i*10f_s:(i+1)*10f_s]$ for all i;
2. $I^{(i)}$ corresponds to a vector of all the peaks in the epoch $y_i[n]$;
3. We initialize a new empty vector x;
4. For each $I^{(i)}$, we perform the following:
   a. We compute the vector $RR:=I^{(i)}[1: end]-I^{(i)}[0: end-1]$ so RR [j] contains the RR interval between $I^{(i)}[j+1]$ and $I^{(i)}[j]$,
   b. For each element RR[j] in RR, we perform the following
      i. We calculate the variability ratio $$r := \frac{\max(RR)}{RR[j]},$$

ii. If $r \geq 2.2$ and $sig[I^{(i)}[j]] > sig[I^{(i)}[j+1]]$, then we append $I^{(i)}[j+1]$ to the end of the vector x, and
   iii. If $r \geq 2.2$ and $+sig [I^{(i)}[j+1]] > sig[I^{(i)}[j]]$, then we append $I^{(i)}$ to the end of the vector x; and
5. We remove all elements of x from I.

The heart variability correction test has now been run on I. The modified PE method for the fingertip plethysmography was implemented as the function peak_envelope_for_pleth.

3.4 Stripped Signal Quality Checker (SSQC)

If the purpose of the method is to determine whether someone is cheating on a study, it is helpful to use only time periods where the signals are valid and exclude periods where the signals are not. It is quite common in sleep studies, for example, that the oximeter probe falls off during the night and the signal becomes invalid. If the coherence of the time periods where the signal is invalid would be included in the analysis, the coherence would be measured as a low value and therefore may falsely indicate cheating. The same applies for any signal involved. Therefore, a method needs to be created for each signal to determine when the signal is considered valid. In the case of this study, this method is a classifier that is referred to as the SSQC program and it was used to determine the quality of ECG, fingertip plethysmography, RIP, and cannula flow signals epoch-wise.

3.5 Intersection Between Two Gaussian Probability Distributions

As any measure contains errors, the measured signals will have some distribution around the correct value. When a classifier is made to determine whether a measure belongs to one class or the other, it is important to figure out the optimal boundary between the two classes. For two Gaussian probability distributed measures, the intersection between the two Gaussian functions is this optimal boundary.

A Gaussian probability distribution with a mean μ and standard deviation a is described by the function:

$$p(x, \mu, \sigma) = \frac{1}{\sigma\sqrt{2\pi}} e^{-\frac{(x-\mu)^2}{2\sigma^2}}.$$

The intersection between two Gaussian probability distributions $N(\mu_1, \sigma_1)$ and $N(\mu_2, \sigma_2)$ are all x such that:

$$p(x,\mu_1,\sigma_1)=p(x,\mu_2,\sigma_2).$$

That is, $$\frac{1}{\sigma_1\sqrt{2\pi}} e^{-\frac{(x-\mu_1)^2}{2\sigma_1^2}} = \frac{1}{\sigma_2\sqrt{2\pi}} e^{-\frac{(x-\mu_2)^2}{2\sigma_2^2}},$$

which can be rewritten as $$\ln(\sigma_1) - \ln(\sigma_2) = \frac{(x-\mu_2)^2}{2\sigma^2} - \frac{(x-\mu_1)^2}{2\sigma^2}.$$

A computer function, such as a Matlab™ function, may be written for solving for x.

4—Testing the Efficiency of the Method to Determine Whether Signals are of the Same Subject Origin

4.1 Coherence Between ECG and Pleth

Coherence between ECG and pleth signals can be thought of as the phase relationship between frequency components in ECG and pleth signals. The idea behind this statistic is that the coherence between these signals are high in the frequency band of the heart beats and harmonics of the heart beats. That is, there should be a constant phase relationship between the frequency components of the signals on the heart's frequency band and its harmonics. If the ECG and pleth signals are from two different people, then the coherence should be quite poor on the heart's frequency band and its harmonics.

In this section, the coherence between ECG and pleth signals will be explored. Firstly, the coherence between whole ECG and pleth signals will be explored alongside proof of concept figures. Secondly, the coherence between each ECG and pleth signal epochs will be explored alongside proof of concept figures.

4.1.1 Signal Preprocessing

Both ECG and pleth signals were filtered with a 2nd degree Butterworth low-pass filter with cut-off frequency 10 Hz. Both signals were then down-sampled to a sampling frequency of 20 Hz.

4.1.2 Coherence Between Whole ECG and Pleth Signals

In this subsection, the coherence between whole ECG and pleth signals will be explored. We begin by plotting the coherence for different recordings.

Our proof of concept includes four coherence plots between pleth and ECG signals from four sleep study recordings. These plots can be seen in FIG. 2, which shows mean coherence, at each frequency for the duration of the measurement, of ECG and pleth signals for four sleep studies The dotted line plot is the coherence between the ECG and pleth signals measured from a relatively healthy person that participated in a partial sleep study.

The broken line plot is the coherence between the ECG and pleth signals measured from a person with severe apnea that participated in a partial sleep study.

The dot-dash line plot is the coherence between the ECG and pleth signals measured from a person during a full sleep study from the LSH dataset. Note that in this study, the pleth and ECG were not fully synchronized in time.

The solid line plot is the coherence between the ECG and pleth signals measured from two different people.

Figure 2:
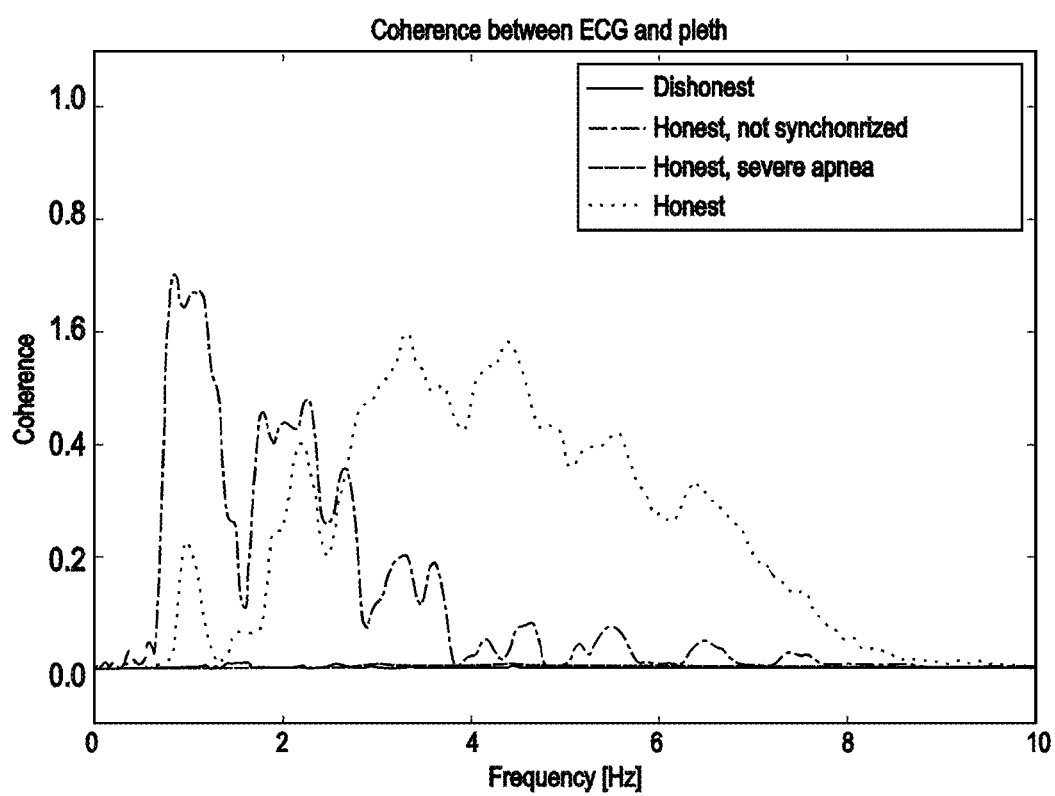
FIG. 2 shows a coherence of ECG and pleth signals for four sleep studies.

There is good coherence between the ECG and pleth signals on the heart's frequency band in most of the honest sleep studies as can be seen in FIG. 2.

Since a significant part of the signals measured on the person with severe sleep apnea were not of good quality the whole night, the coherence between the ECG and pleth on this recording was poor. The coherence was calculated again on ECG and pleth signals from the same person during a period when the signals were of acceptable quality (20000 sec-25000 sec). The corrected coherence figure can be seen in FIG. 3, which shows a coherence of ECG and pleth signals for four sleep studies with one study clipped.

Figure 3:
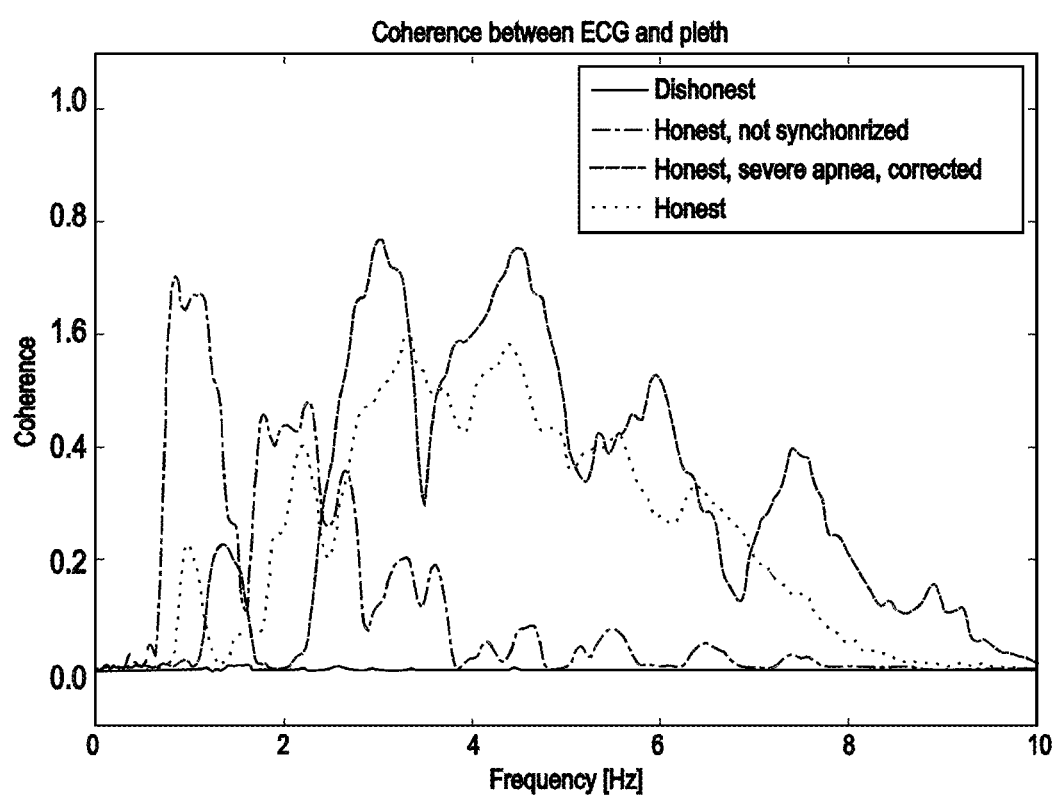
FIG. 3 shows a coherence of ECG and pleth signals for four sleep studies with one study clipped.

In FIG. 3, all the honest recordings have much higher coherence than the dishonest recording. However, in FIG. 2, the person with severe apnea had low coherence, which was due to low quality of the measurement in some time periods. Therefore, the total coherence of the pleth and coherence signals may not be a sufficient statistic for determining fraudulent sleep studies without some preprocessing involving a signal quality checker, as mentioned above A segmented coherence statistic might be more suitable to give a more thorough overview of how the coherence changes with time. A segmented coherence statistic will be explored in the next subsection.

4.1.3 Coherence Between ECG and Pleth Signal Epochs

In this subsection, the coherence between segmented ECG and pleth signals will be explored by using coherence spectrograms. We begin by plotting the coherence spectrograms for different recordings.

Our proof of concept includes four coherence spectrograms.

Figure 4:
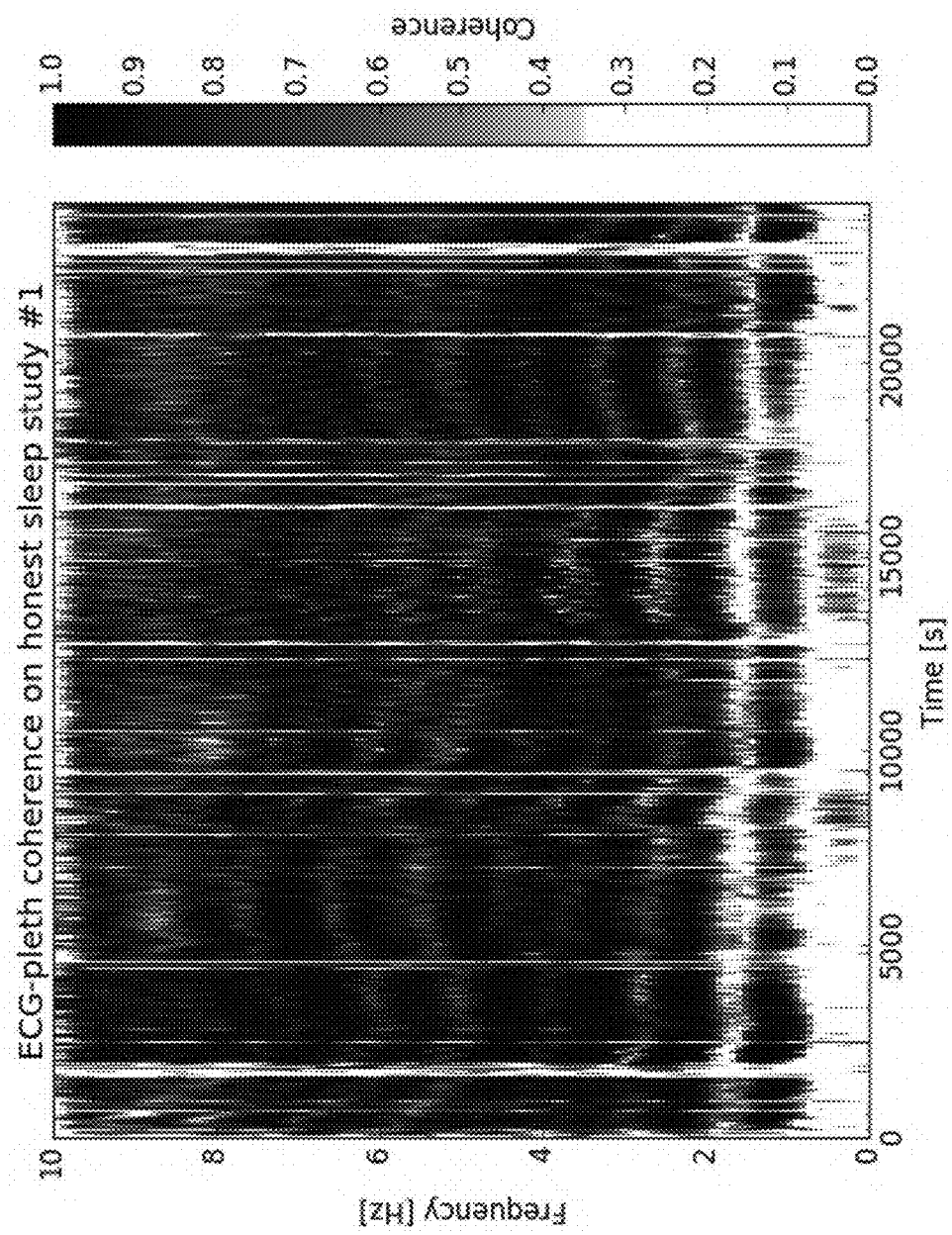
FIG. 4 shows a coherence spectrogram of ECG and pleth signals measured in an honest sleep study.

FIG. 4 is a first spectrogram, which shows a coherence spectrogram of ECG and pleth signals measured in an honest sleep study. Thus FIG. 4 shows the coherence between ECG and pleth signals, both measured from a relatively healthy person that participated in a partial sleep study.

Figure 5:
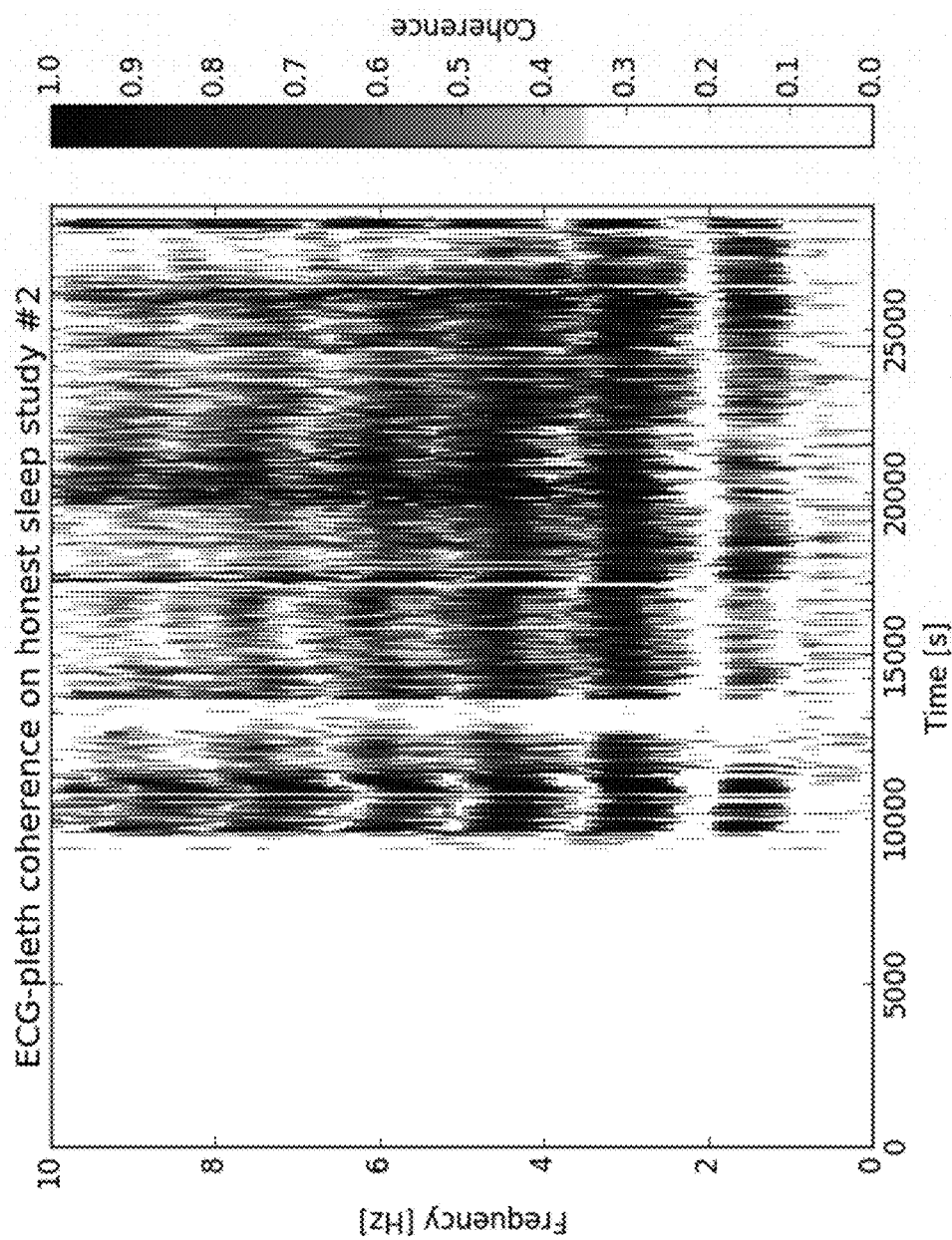
FIG. 5 shows a coherence spectrogram of ECG and pleth signals measured in an honest sleep study where the patient suffers from severe apnea.

FIG. 5 is a second spectrogram, which shows a coherence spectrogram of ECG and pleth signals measured in an honest sleep study where the patient suffers from severe apnea. Thus FIG. 5 shows the coherence between ECG and pleth signals measured from a person with severe apnea that participated in a partial sleep study.

Figure 6:
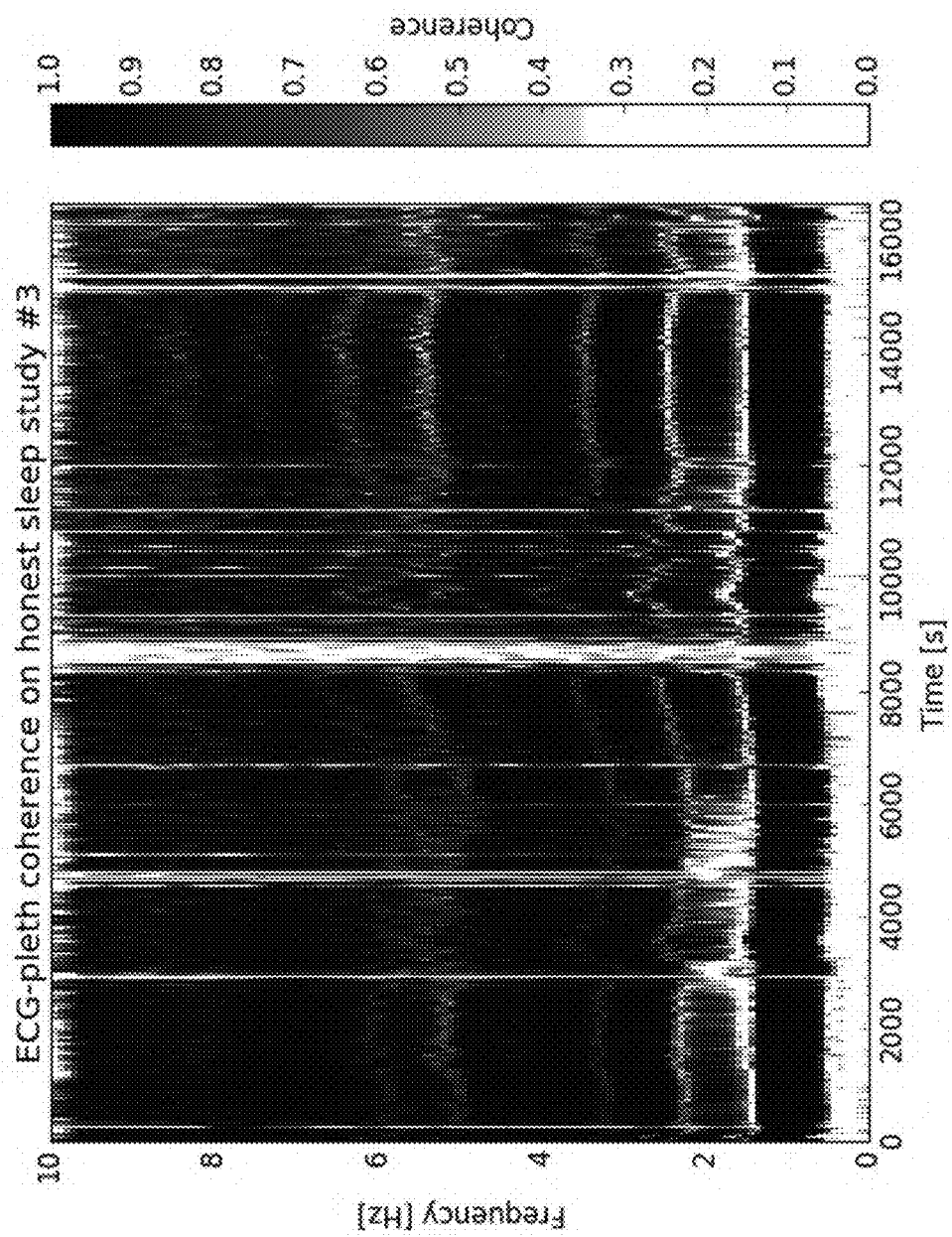
FIG. 6 shows a coherence spectrogram of ECG and pleth signals measured in an honest sleep study where the ECG and pleth signals are not correctly synchronized.

FIG. 6 is a third spectrogram, which shows a coherence spectrogram of ECG and pleth signals measured in an honest sleep study where the ECG and pleth signals are not correctly synchronized. FIG. 6 thus shows the coherence between ECG and pleth signals measured from a person during a full sleep study from the LSH dataset. Note that in this study, the pleth and ECG were not fully synchronized in time.

Figure 7:
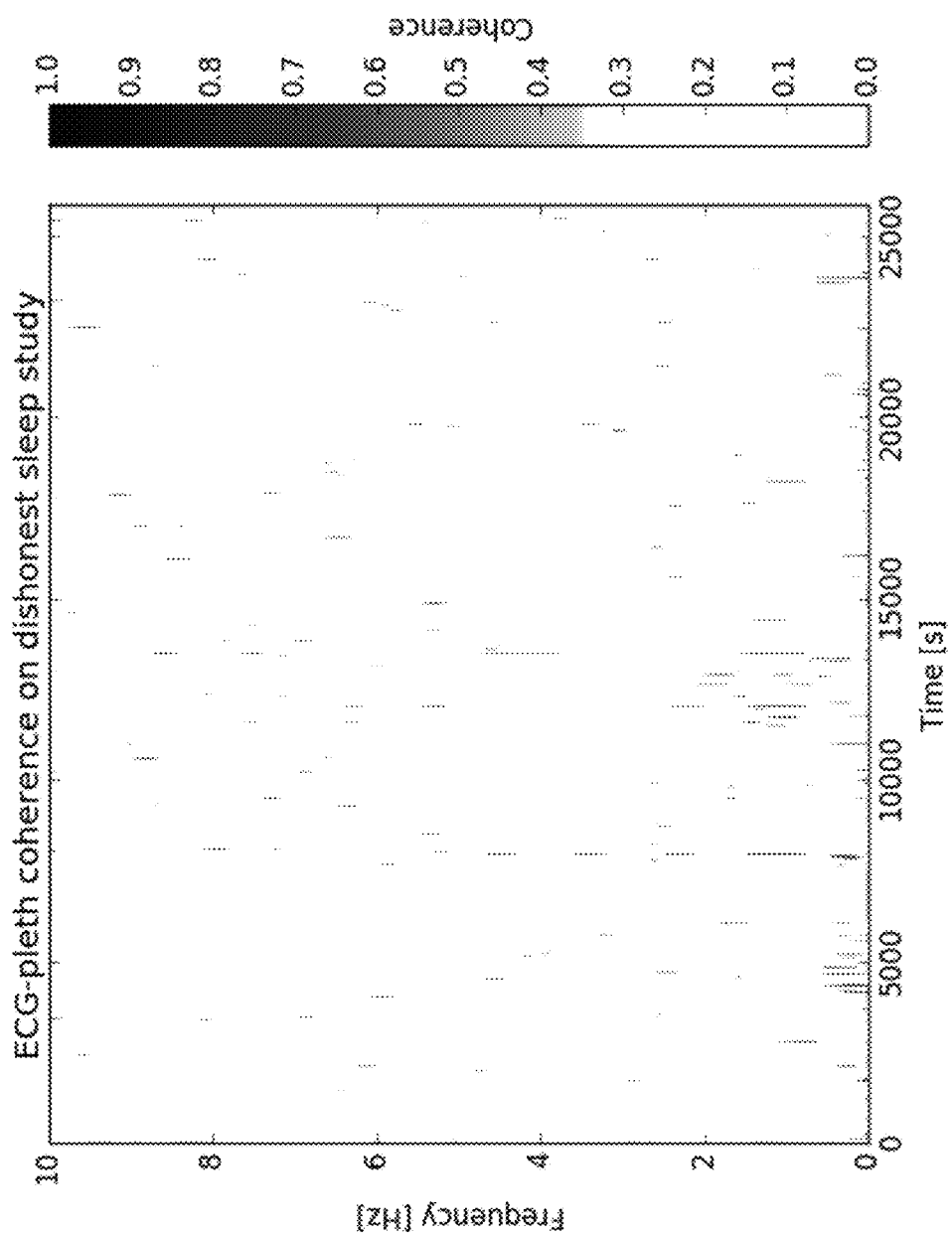
FIG. 7 shows a coherence spectrogram of ECG and pleth signals measured in a dishonest sleep study.

FIG. 7 is a fourth spectrogram, which shows a coherence spectrogram of ECG and pleth signals measured in a dishonest sleep study. FIG. 7 thus shows the coherence between ECG and pleth signals measured from two different people.

There is good coherence between the ECG and pleth on the heart's frequency band in the honest sleep studies. Note that the reason why the coherence was low in the beginning of FIG. 5 was because the recording started before the patient applied the sleep study equipment on himself. There is also bad coherence between the ECG and pleth on the heart's frequency band in the dishonest sleep study.

This means that this segmented coherence statistic could be used for building a metric for detecting fraudulent sleep studies.

4.1.4 Coherence Metric Based on Coherence Length

In physics, coherence length and coherence time are two metrics of signal coherence strength. One metric of coherence strength between two signals of a physiological study is the maximum epoch length which results in a coherence value above a certain threshold. This metric would result in a short duration for dishonest measurements while resulting in a long duration for honest measurements.

4.2 Coherence Between RIP and Pleth

Coherence between RIP and pleth signals can be thought of as the phase relationship between frequency components in those signals. The idea behind this statistic is that the coherence between these signals are high on the frequency band where the heart beats. That is, there should be a synchronous relationship between the frequency components of the signals on the heart's frequency band. If the RIP and pleth signals are from two different people, then the coherence should be quite poor on the heart's frequency band.

In this section, the coherence between RIP and pleth signals will be explored. Firstly, the coherence between whole RIP and pleth signals will be explored alongside proof of concept figures. Secondly, the coherence between each RIP and pleth signal epochs will be explored alongside proof of concept figures.

4.2.1 Signal Preprocessing

RIP Abdomen and thorax volume signals, and the pleth signals were filtered with a 2nd degree Butterworth low-pass filter with cut-off frequency 10 Hz. All of the signals were then down-sampled to a sampling frequency of 20 Hz.

4.2.2 Coherence Between Whole RIP and Pleth Signals

In this subsection, the coherence between whole RIP and pleth signals will be explored. We begin by plotting the coherence for different recordings.

Figures 8A, 8B:
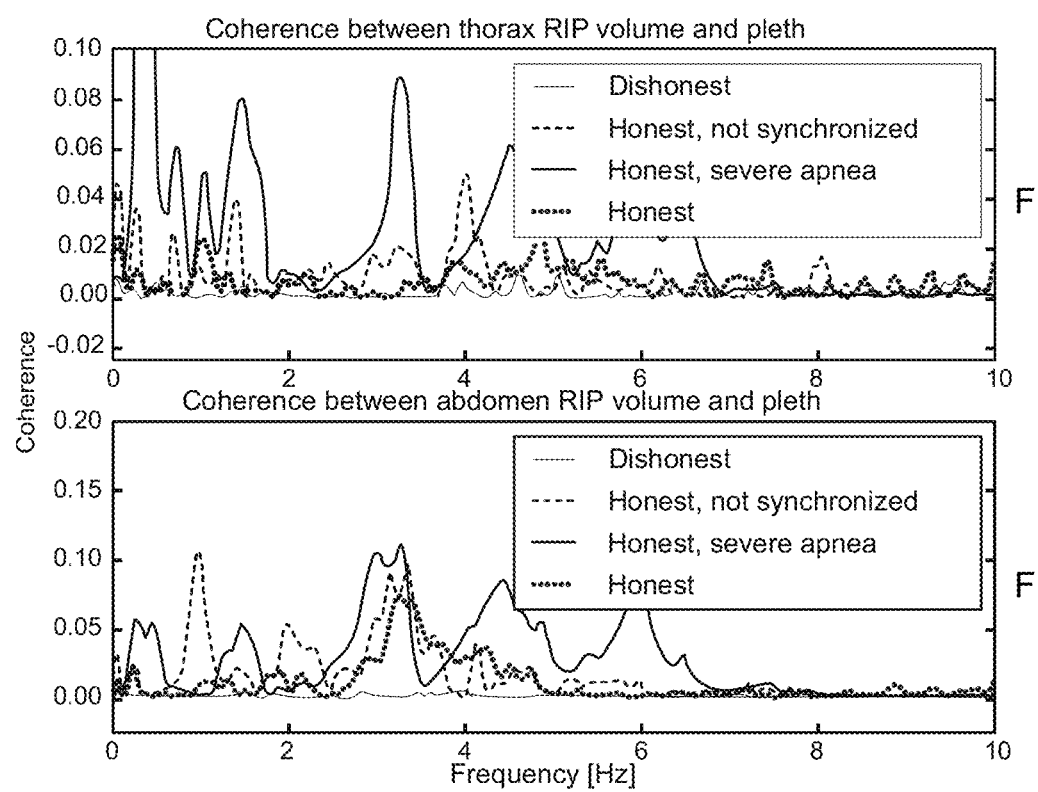
FIG. 8(A) shows a coherence between thorax respiratory inductance plethysmography (RIP) volume and pleth signals.
FIG. 8(B) shows a coherence of abdomen respiratory inductance plethysmography (RIP) and pleth signals for four sleep studies.

Our proof of concept will be four coherence plots between pleth and RIP volume signals from four sleep study recordings. These plots can be seen in FIGS. 8(A) and 8(B), which shows a coherence of RIP and pleth signals for four sleep studies.

The dotted line plot is the coherence between the RIP volume and pleth signals measured from a relatively healthy person that participated in a partial sleep study.

The bolded line plot is the coherence between the RIP volume and pleth signals measured from a person with severe apnea that participated in a partial sleep study.

The broken line plot is the coherence between the RIP volume and pleth signals measured from a person during a full sleep study from the LSH dataset. Note that in this study, the pleth and RIP were not fully synchronized in time.

The solid line plot is the coherence between the RIP volume and pleth signals measured from two different people.

There is a difference between the coherence of the honest sleep studies and the dishonest sleep study. However, the coherence of one of the honest measurements seems to be slightly close to the coherence of the dishonest measurement. This may be due to signal artifacts or irregularities in some epochs.

A segmented coherence statistic might be more suitable to give more thorough overview over how the coherence changes with time. A segmented coherence statistic will be explored in the next subsection.

4.2.3 Coherence Between RIP and Pleth Signal Epochs

In this subsection, the coherence between segmented RIP volume and pleth signals will be explored by using coherence spectrograms. We begin by plotting the coherence spectrograms for different recordings.

Our proof of concept will be four coherence spectrograms.

FIGS. 9(A) and 9(B) show a first spectrogram, which shows a coherence spectrogram of RIP volume and pleth signals measured in an honest sleep study. FIGS. 9(A) and 9(B) thus show the coherence between RIP volume and pleth signals, both measured from a relatively healthy person that participated in a partial sleep study.

FIGS. 10(A) and 10(B) show a second spectrogram, which shows a Coherence spectrogram of RIP volume and pleth signals measured in an honest sleep study where the patient suffers from severe apnea. FIGS. 10(A) and 10(B) thus show the coherence between RIP volume and pleth signals measured from a person with severe apnea that participated in a partial sleep study.

FIGS. 11(A) and 11(B) show a third spectrogram, which show a coherence spectrogram of RIP volume and pleth signals measured in an honest sleep study where the RIP and pleth signals are not correctly synchronized. FIGS. 11(A) and 11(B) thus show the coherence between RIP volume and pleth signals measured from a person during a full sleep study from the LSH dataset. Note that in this study, the pleth and RIP were not fully synchronized in time.

FIGS. 12(A) and 12(B) show a fourth spectrogram, which shows a coherence spectrogram of RIP volume and pleth signals measured in a dishonest sleep study. FIGS. 12(A) and 12(B) thus show the coherence between RIP volume and pleth signals measured from two different people.

There is good coherence between the RIP and pleth signals on the heart's frequency band in the honest sleep studies. Note that the reason why the coherence was low in the beginning of FIGS. 10(A) and 10(B) was because the recording started before the patient applied the sleep study equipment on himself. There is also bad coherence between the RIP and pleth signals on the heart's frequency band in the dishonest sleep study.

This means that this segmented coherence statistic could be used for building a metric for detecting fraudulent physiological studies, for example, sleep studies. Furthermore, this means that measuring the length of epochs which result in a coherence above a certain threshold could be a useful metric of measurement quality.

4.3 Coherence Between RIP and Pleth Envelope

The amplitude of the pleth signal is said to be dependent on respiration, thus the pleth signal is amplitude modulated with respiration. This means that the envelope of the pleth signal is a signal that gives information about respiration. (See A. Roebuck, V. Monasterio, E. Gederi, M. Osipov, B. J. A. Malhotra, T. Penzel and G. D. Clifford, "A review of signals used in sleep analysis," Physiological Measurement, vol. 35, no. 1, pp. 1-57, 2014, which is incorporated herein by reference in its entirety.)

Coherence between RIP and pleth envelope signals can be thought of as a metric of the phase relation between frequency components in those signals. The idea behind this statistic is that the coherence between these signals are high on a frequency band of possible breathing frequencies. That is, there should be a synchronous relationship between the frequency components of the signals on that frequency band. If the RIP and pleth envelope signals are from two different people, then the coherence should be quite poor on this specific frequency band.

In this section, the coherence between RIP and pleth envelope signals will be explored. Firstly, the coherence between whole RIP and pleth envelope signals will be explored alongside proof of concept figures. Secondly, the coherence between each RIP and pleth envelope signal epochs will be explored alongside proof of concept figures.

4.3.1 Signal Preprocessing

The abdomen and thorax RIP volume signals and the pleth signals were filtered with a 2nd degree Butterworth low-pass filter with cut-off frequency 10 Hz. Both signals were then down-sampled to a sampling frequency of 20 Hz. The envelope of the pleth signal was computed with the method proposed in 3.3.1.2.

4.3.2 Coherence Between Whole RIP and Pleth Envelope Signals

In this subsection, the coherence between whole RIP and pleth envelope signals will be explored. We begin by plotting the coherence for different recordings.

Our proof of concept will be four coherence plots between pleth envelopes and RIP volume signals from four sleep study recordings. These plots can be seen in FIGS. 13(A) and 13(B), which show a coherence of RIP and pleth envelope signals for four sleep studies The dotted line plot is the coherence between the RIP volume and pleth envelope signals measured from a relatively healthy person that participated in a partial sleep study.

The bolded line plot is the coherence between the RIP volume and pleth envelope signals measured from a person with severe apnea that participated in a partial sleep study.

The broken line plot is the coherence between the RIP volume and pleth envelope signals measured from a person during a full sleep study from the LSH dataset. Note that in this study, the pleth and RIP were not fully synchronized in time.

The solid line plot is the coherence between the RIP volume and pleth envelope signals measured from two different people.

Figures 13A, 13B:
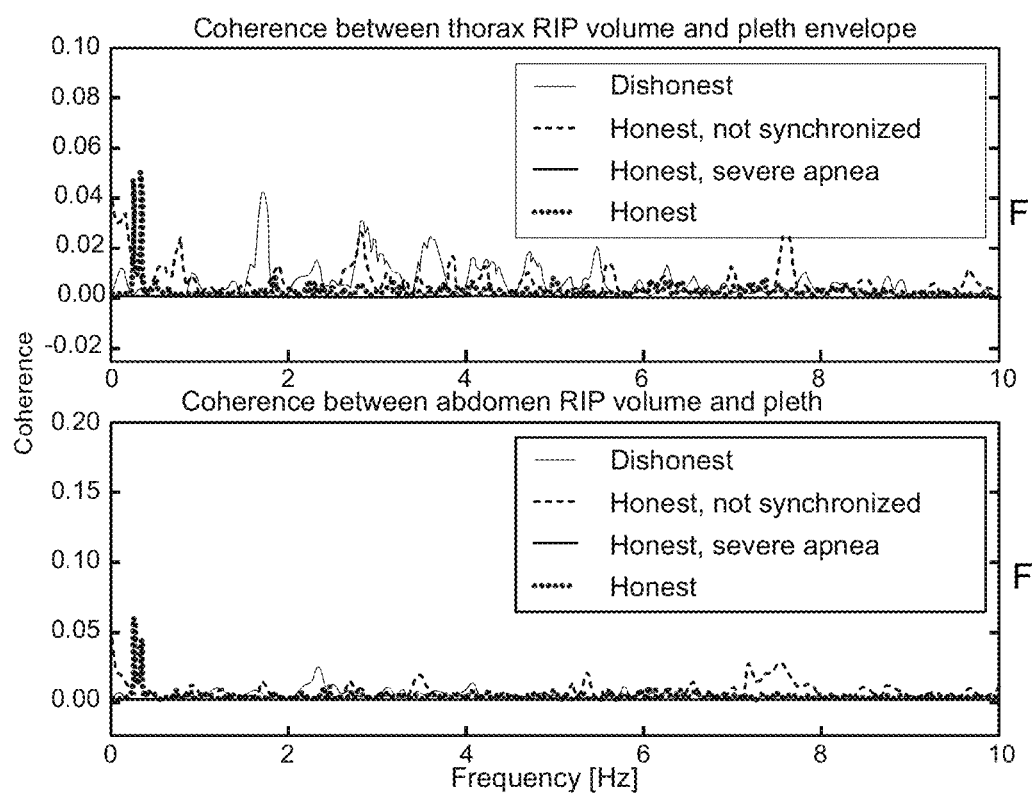
FIGS. 13(A) and 13(B) show a coherence of thorax and abdomen RIP and pleth envelope signals, respectively, for four sleep studies.

It seems that no noticeable pattern can be seen in FIGS. 13(A) and 13(B). A segmented coherence statistic may be more suitable for finding a pattern between the RIP and pleth envelope signals. A segmented coherence statistic will be explored in the next subsection.

4.3.3 Coherence Between RIP and Pleth Envelope Signal Epochs

In this subsection, the coherence between segmented RIP volume and pleth envelope signals will be explored using coherence spectrograms. We begin by plotting the coherence spectrograms for different recordings.

Our proof of concept includes four coherence spectrograms.

FIGS. 14(A) and 14(B) show a first spectrogram, which shows a coherence spectrogram of RIP volume and pleth envelope signals measured in an honest sleep study. FIGS. 14(A) and 14(B) thus show the coherence between RIP volume and pleth envelope signals, both measured from a relatively healthy person that participated in a partial sleep study.

FIGS. 15(A) and 15(B) show a second spectrogram, which shows a coherence spectrogram of RIP volume and pleth envelope signals measured in an honest sleep study where the patient suffers from severe apnea. FIGS. 15(A) and 15(B) thus show the coherence between RIP volume and pleth envelope signals measured from a person with severe apnea that participated in a partial sleep study.

FIGS. 16(A) and 16(B) show a third spectrogram, which shows a coherence spectrogram of RIP volume and pleth envelope signals measured in an honest sleep study where the RIP and pleth signals are not correctly synchronized. FIGS. 16(A) and 16(B) thus show the coherence between RIP volume and pleth envelope signals measured from a person during a full sleep study from the LSH dataset. Note that in this study, the pleth and RIP were not fully synchronized in time.

FIGS. 17 (A) and 17(B) show a fourth spectrogram, which shows a coherence spectrogram of RIP volume and pleth envelope signals measured in a dishonest sleep study. FIGS. 17 (A) and 17(B) thus show the coherence between RIP volume and pleth envelope signals measured from two different people.

There is a noticeable pattern on the coherence spectrograms. It seems like the honest sleep studies show noticeably more coherence on a specific frequency band (containing the frequencies that the subject breaths at) than the dishonest sleep study.

The noticeable pattern could be an indication that a metric for detecting fraudulent sleep studies could be built from this segmented coherence statistic. The epoch length giving a coherence value above a certain threshold could be used here as a metric of the signal coherence strength. 4.4 Coherence between RIP envelope and pleth envelope The envelope of a RIP volume signal describes how the breathing amplitude changes with time.

Coherence between RIP envelope and pleth envelope signals can be thought of as the phase relationship between frequency components in those signals. The idea behind this statistic is that the coherence between these signals are high on a frequency band of possible breathing frequencies. That is, there should be a synchronous relationship between the frequency components of the signals on that frequency band. If the RIP envelope and the pleth envelope signals are from two different people, then the coherence should be quite poor on this specific frequency band.

In this section, the coherence between RIP and pleth envelope signals will be explored. Firstly, the coherence between whole RIP and pleth envelope signals will be explored alongside proof of concept figures. Secondly, the coherence between each RIP envelope and pleth envelope signal epochs will be explored alongside proof of concept figures.

4.4.1 Signal Preprocessing

The abdomen and thorax RIP volume signals and the pleth signals were filtered with a 2nd degree Butterworth low-pass filter with cut-off frequency 10 Hz. Both signals were then down-sampled to a sampling frequency of 20 Hz. The envelope of the pleth signal was computed with the method proposed in subsection 3.3.1.2. The envelopes of the RIP volume signals were computed with the method proposed in subsection 3.3.1.1.

4.4.2 Coherence between whole RIP envelope and pleth envelope signals

In this subsection, the coherence between whole RIP envelope and pleth envelope signals will be explored. We begin by plotting the coherence for different recordings.

Our proof of concept includes four coherence plots between pleth envelope and RIP envelope signals from four sleep study recordings. These plots can be seen in FIGS. 18(A) and 18(B), which shows a coherence of RIP envelope and pleth envelope signals for four sleep studies.

The dotted line plot is the coherence between the RIP envelope and pleth envelope signals measured from a relatively healthy person that participated in a partial sleep study.

The bolded line plot is the coherence between the RIP envelope and pleth envelope signals measured from a person with severe apnea that participated in a partial sleep study.

The broken line plot is the coherence between the RIP envelope and pleth envelope signals measured from a person during a full sleep study from the LSH dataset. Note that in this study, the pleth and RIP were not fully synchronized in time.

The solid line plot is the coherence between the RIP envelope and pleth envelope signals measured from two different people.

No noticeable pattern appears to be discernible in FIGS. 18(A) and 18(B). A segmented coherence statistic may be more suitable for finding a pattern between the RIP envelope and pleth envelope signals. A segmented coherence statistic will be explored in the next subsection.

4.4.3 Coherence Between RIP Envelope and Pleth Envelope Signal Epochs

In this subsection, the coherence between segmented RIP volume envelope and pleth envelope signals will be explored using coherence spectrograms. We begin by plotting the coherence spectrograms for different recordings.

Our proof of concept includes four coherence spectrograms.

FIGS. 19 (A) and 19(B) shows a first spectrogram, which shows a coherence spectrogram of RIP volume envelope and pleth envelope signals measured in an honest sleep study. FIGS. 19 (A) and 19(B) thus show the coherence between RIP volume envelope and pleth envelope signals, both measured from a relatively healthy person that participated in a partial sleep study.

FIGS. 20 (A) and 20(B) is a second spectrogram, which shows a coherence spectrogram of RIP volume envelope and pleth envelope signals measured in an honest sleep study where the patient suffers from severe apnea. FIGS. 20 (A) and 20(B) thus show the coherence between RIP volume envelope and pleth envelope signals measured from a person with severe apnea that participated in a partial sleep study.

FIGS. 21 (A) and 21(B) shows is a third spectrogram, which shows a coherence spectrogram of RIP volume envelope and pleth envelope signals measured in an honest sleep study where the RIP and pleth signals are not correctly synchronized. FIGS. 21 (A) and 21(B) thus show the coherence between RIP volume envelope and pleth envelope signals measured from a person during a full sleep study from the LSH dataset. Note that in this study, the pleth and RIP were not fully synchronized in time.

FIGS. 22 (A) and 22(B) is a fourth spectrogram, which shows a coherence spectrogram of RIP volume envelope and pleth envelope signals measured in a dishonest sleep study. FIGS. 22 (A) and 22(B) thus show the coherence between RIP volume envelope and pleth envelope signals measured from two different people.

There does not appear to be a noticeable pattern in FIGS. 19(A) and 19(B), FIGS. 20(A) and 20(B), FIGS. 21(A) and 21(B), and FIGS. 22(A) and 22(B). Therefore, it is likely that the coherence between RIP envelopes and pleth envelopes statistic would be difficult to use as a metric for detecting a fraudulent sleep study.

Note that the high coherence early in time in FIGS. 20(A) and 20(B) is not believed to be noteworthy since the sleep study it depicts did not start until around time 10000 sec.

4.5 Coherence Between Cannula Flow and Pleth Envelope

Coherence between cannula flow and pleth envelope signals can be thought of as the phase relation between frequency components in those signals. The idea behind this statistic is that the coherence between these signals is high on a frequency band of possible breathing frequencies. That is, there should be a synchronous relationship between the frequency components of the signals on that frequency band. If the cannula flow and pleth envelope signals are from two different people, then the coherence should be quite poor on this specific frequency band.

In this section, the coherence between cannula flow and pleth envelope signals will be explored. Firstly, the coherence between whole cannula flow and pleth envelope signals will be explored alongside proof of concept figures. Secondly, the coherence between each cannula flow and pleth envelope signal epochs will be explored alongside proof of concept figures.

4.5.1 Signal Preprocessing

The cannula flow and the pleth signals were filtered with a 2nd degree Butterworth low-pass filter with cut-off frequency 10 Hz. Both signals were then down-sampled to a sampling frequency of 20 Hz. The envelope of the pleth signal was computed with the method proposed in 3.3.1.2.

4.5.2 Coherence Between Whole Cannula Flow and Pleth Envelope Signals

In this subsection, the coherence between whole cannula flow and pleth envelope signals will be explored. We begin by plotting the coherence for different recordings.

Our proof of concept includes four coherence plots between pleth envelopes and cannula flow signals from four sleep study recordings. These plots can be seen in FIG. 23 which shows a coherence of cannula flow and pleth envelope signals for four sleep studies.

The broken line plot is the coherence between the cannula flow and pleth envelope signals measured from a relatively healthy person that participated in a partial sleep study.

The dotted line plot is the coherence between the cannula flow and pleth envelope signals measured from a person with severe apnea that participated in a partial sleep study.

The black plot is the coherence between the cannula flow and pleth envelope signals measured from a person during a full sleep study from the LSH dataset. Note that in this study, the pleth and cannula flow were not fully synchronized in time. Also, note that the cannula flow in this study is not really the cannula flow. Rather, the flow is measured by a continuous positive airway pressure (CPAP) machine. For simplicity, we will continue referring to this flow signal as cannula flow.

The solid line plot is the coherence between the cannula flow and pleth envelope signals measured from two different people.

Figure 23:
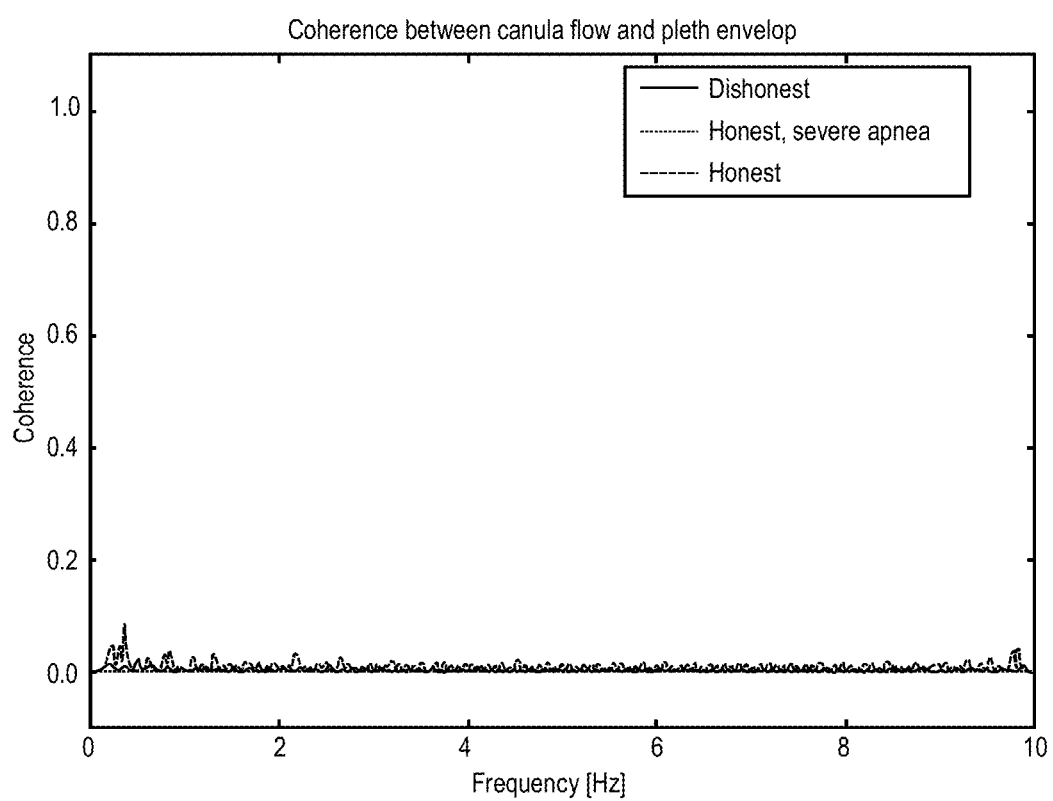
FIG. 23 shows a coherence of cannula flow and pleth envelope signals for four sleep studies.

No noticeable pattern appears in FIG. 23. A segmented coherence statistic may be more suitable for finding a pattern between the cannula flow and pleth envelope signals. A segmented coherence statistic will be explored in the next subsection.

4.5.3 Coherence Between Cannula Flow and Pleth Envelope Signal Epochs

In this subsection, the coherence between segmented cannula flow and pleth envelope signals will be explored using coherence spectrograms. We begin by plotting the coherence spectrograms for different recordings.

Our proof of concept includes four coherence spectrograms.

Figure 24:
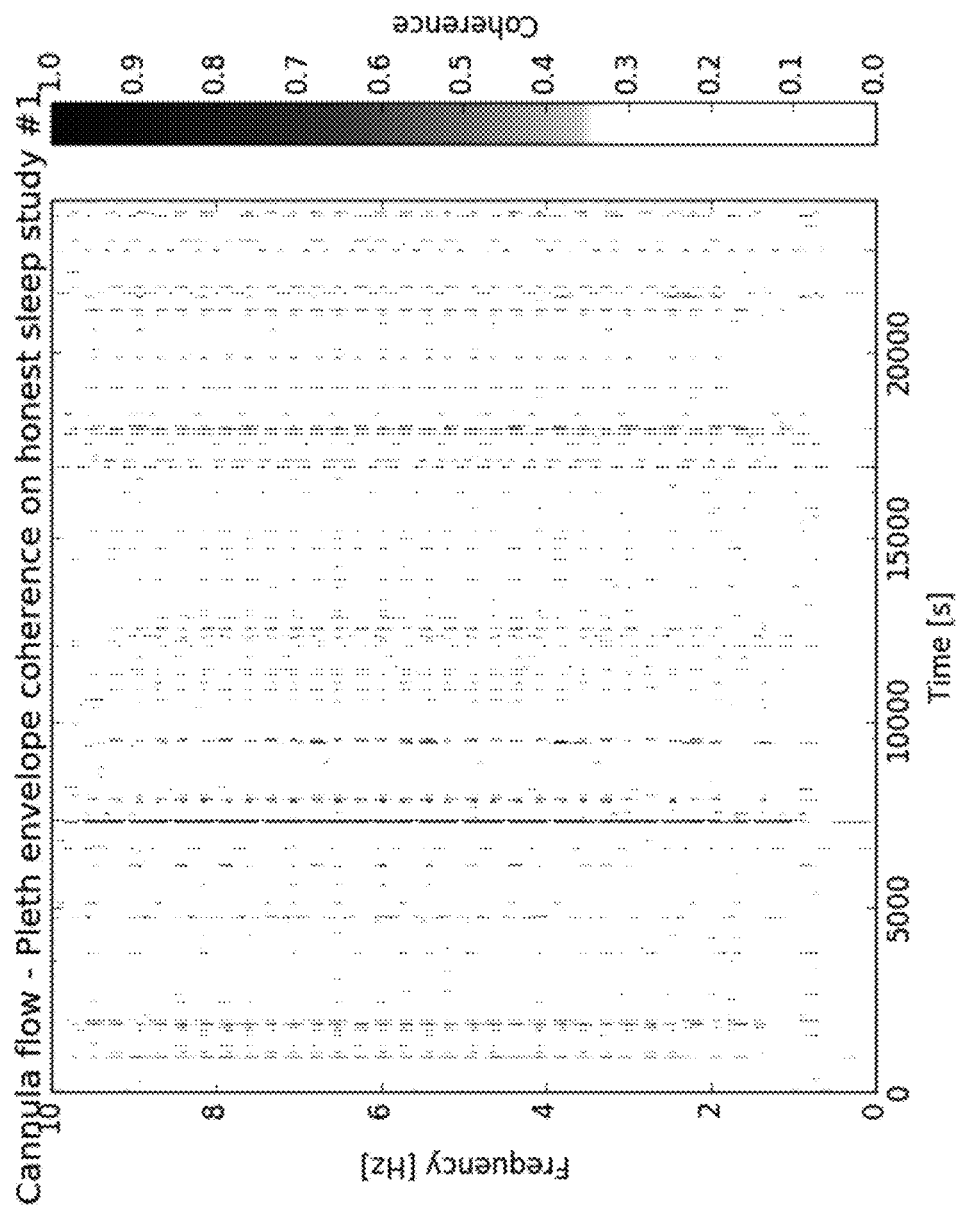
FIG. 24 shows a coherence spectrogram of cannula flow and pleth envelope signals measured in an honest sleep study.

FIG. 24 is a first spectrogram, which shows a coherence spectrogram of cannula flow and pleth envelope signals measured in an honest sleep study. FIG. 24 thus shows the coherence between cannula flow and pleth envelope signals, both measured from a relatively healthy person that participated in a partial sleep study.

Figure 25:
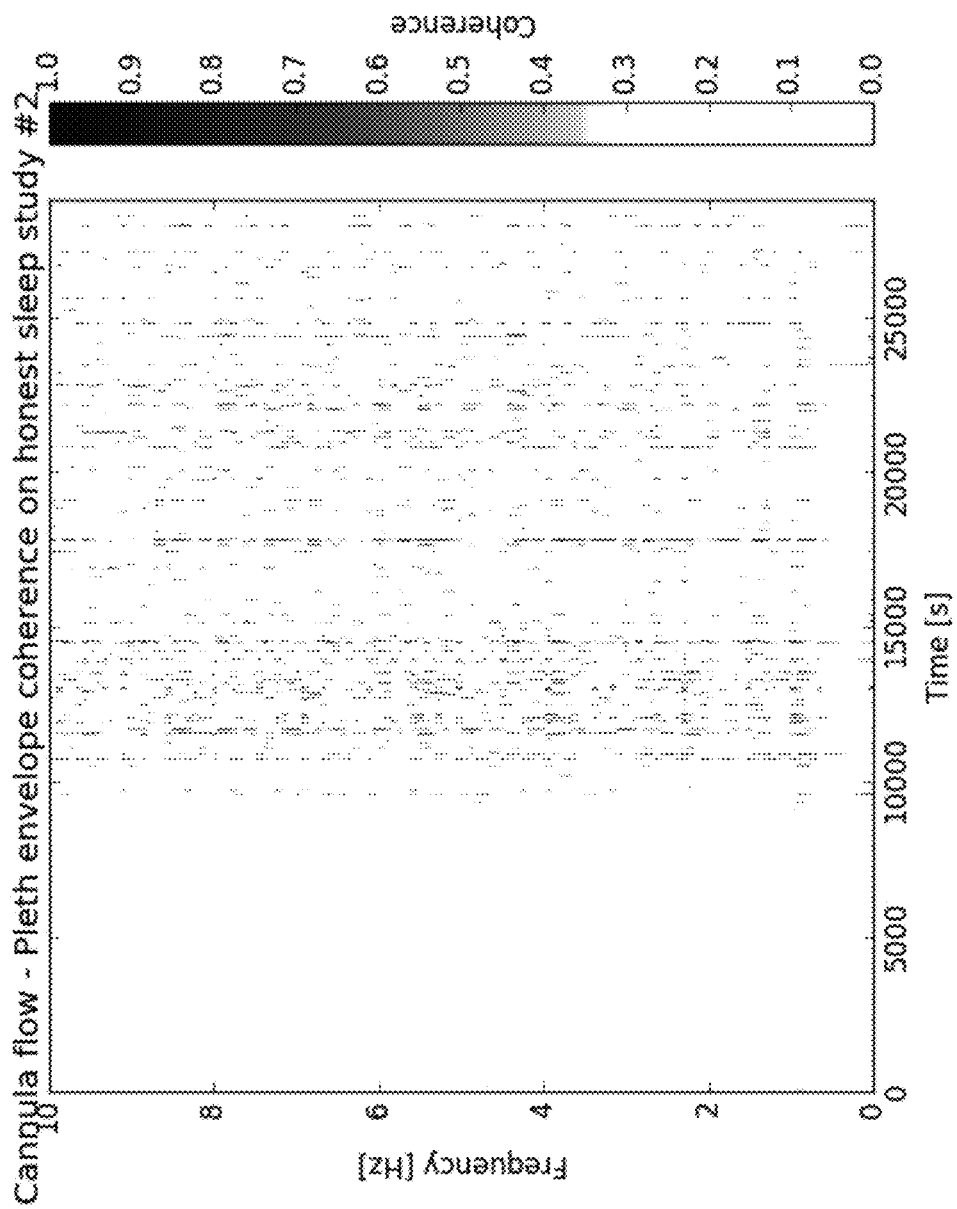
FIG. 25 shows a coherence spectrogram of cannula flow and pleth envelope signals measured in an honest sleep study where the patient suffers from severe apnea

FIG. 25 is a second spectrogram, which shows a coherence spectrogram of cannula flow and pleth envelope signals measured in an honest sleep study where the patient suffers from severe apnea. FIG. 25 thus shows the coherence between cannula flow and pleth envelope signals measured from a person with severe apnea that participated in a partial sleep study.

Figure 26:
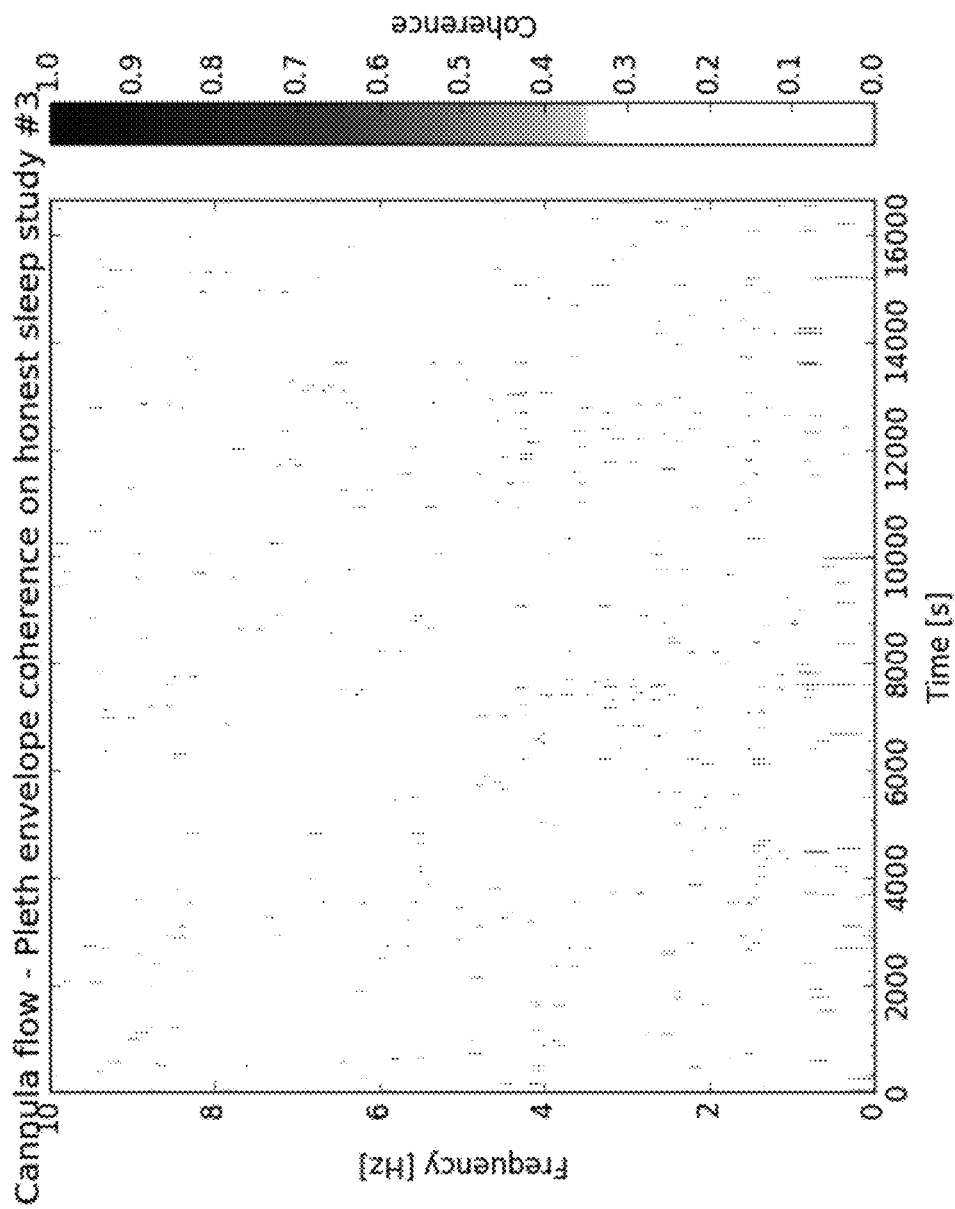
FIG. 26 shows a coherence spectrogram of cannula flow and pleth envelope signals measured in an honest sleep study where the cannula flow and pleth signals are not correctly synchronized.

FIG. 26 is a third spectrogram, which shows a coherence spectrogram of cannula flow and pleth envelope signals measured in an honest sleep study where the cannula flow and pleth signals are not correctly synchronized. FIG. 26 thus shows the coherence between cannula flow and pleth envelope signals measured from a person during a full sleep study from the LSH dataset. Note that in this study, the pleth and cannula flow were not fully synchronized in time. Also, note that the cannula flow in this study is not really the cannula flow. Rather, the flow is measured by a CPAP machine. For simplicity, we will continue referring to this flow signal as cannula flow.

Figure 27:
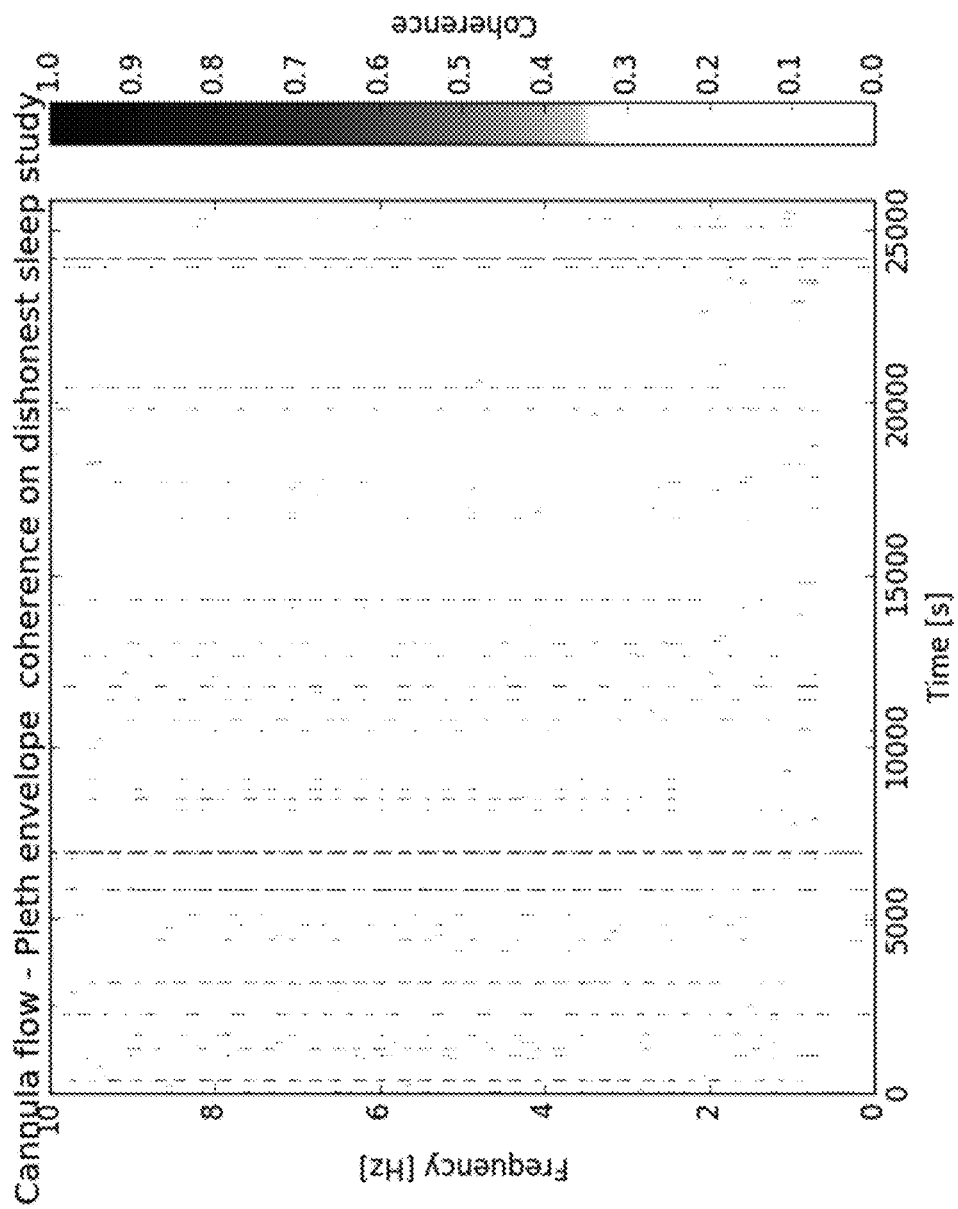
FIG. 27 shows a coherence spectrogram of cannula flow and pleth envelope signals measured in a dishonest sleep study.

FIG. 27 is a fourth spectrogram, which shows a coherence spectrogram of cannula flow and pleth envelope signals measured in a dishonest sleep study. FIG. 27 thus shows the coherence between cannula flow and pleth envelope signals measured from two different people.

There does not appears to be a noticeable pattern in FIG. 24, FIG. 25, FIG. 26, and FIG. 27. Therefore, it is likely that the coherence between cannula flow and pleth envelopes statistic cannot be used to make a metric for detecting a fraudulent sleep study.

4.6 Coherence after Signal Quality Check

In this section, we will use the SSQC introduced in section 3.4 to detect all epochs of unacceptable quality in the sleep recordings used in sections 4.1, 4.2, 4.3, 4.4, and 4.5 and reconstruct the recordings using only the epochs of acceptable signal quality. Afterwards, we will plot the same plots as FIG. 2, FIG. 8, FIG. 13, FIG. 18, and FIG. 23 using the reconstructed signals.

4.6.1 Preprocessing

All the signals used in this section were preprocessed in the following way:

- All signals were filtered with a 2nd degree Butterworth low-pass filter with cut-off frequency 10 Hz and then down-sampled to a sampling frequency of 20 Hz; and
- The SSQC was used to reject signal epochs of questionable quality for each signal pair before calculating the coherence

4.6.2 Coherence Between Whole ECG and Pleth Signals

In this subsection, the coherence between whole ECG and pleth signals will be explored. We begin by plotting the coherence for different recordings.

Our proof of concept includes four coherence plots between pleth and ECG signals from four sleep study recordings. These plots can be seen in FIG. 28, which shows a coherence of cleaned ECG and pleth signals for four sleep studies The dotted line plot is the coherence between the ECG and pleth signals measured from a relatively healthy person that participated in a partial sleep study.

The bolded line plot is the coherence between the ECG and pleth signals measured from a person with severe apnea that participated in a partial sleep study.

The broken line plot is the coherence between the ECG and pleth signals measured from a person during a full sleep study from the LSH dataset. Note that in this study, the pleth and ECG were not fully synchronized in time.

The solid line plot is the coherence between the ECG and pleth signals measured from two different people.

Figure 28:
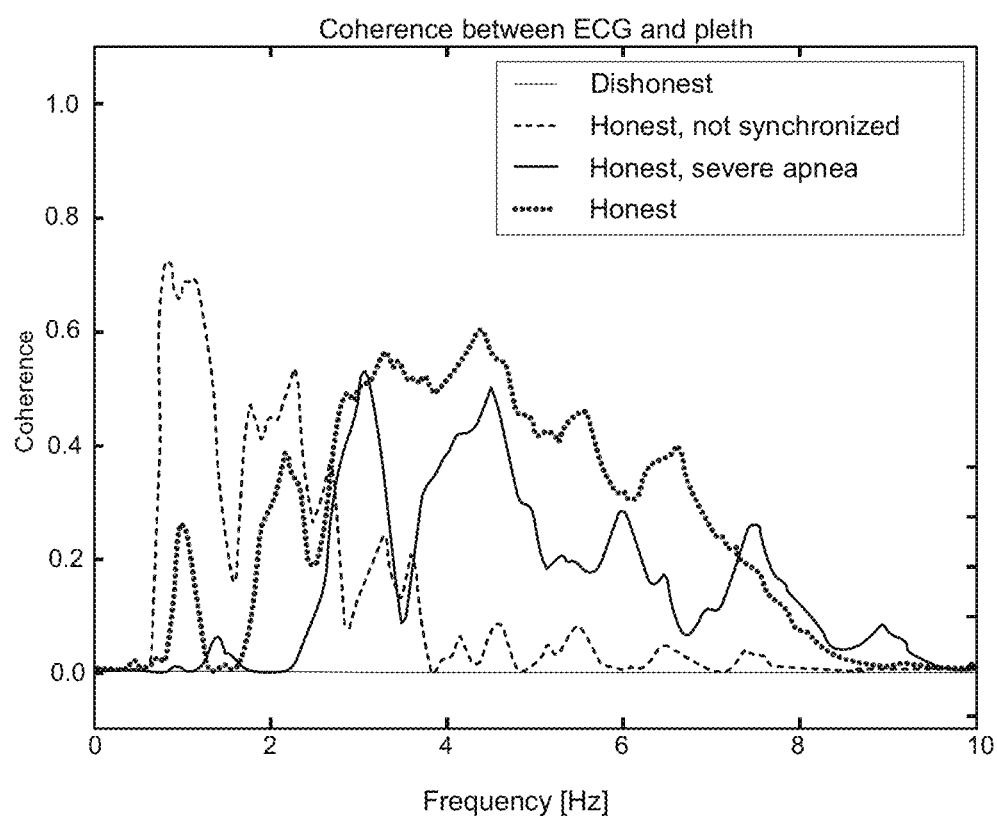
FIG. 28 shows a coherence of cleaned ECG and pleth signals, respectively, for four sleep studies

In FIG. 28, we can see that there is a difference between the honest and dishonest sleep studies. That is, the honest sleep studies have much higher coherence on the heart's frequency band than the dishonest sleep study. This implies that the coherence between the whole ECG and pleth signals could be used for constructing a metric that determines whether a person cheated in a sleep study.

4.6.3 Coherence Between Whole RIP and Pleth Signals

In this subsection, the coherence between whole RIP and pleth signals will be explored. We begin by plotting the coherence for different recordings.

Our proof of concept includes four coherence plots between pleth and RIP volume signals from four sleep study recordings. These plots can be seen in FIGS. 29(A) and 29(B), which show a coherence of cleaned RIP volume and pleth signals for four sleep studies.

The dotted line plot is the coherence between the RIP volume and pleth signals measured from a relatively healthy person that participated in a partial sleep study.

The bolded line plot is the coherence between the RIP volume and pleth signals measured from a person with severe apnea that participated in a partial sleep study.

The broken line plot is the coherence between the RIP volume and pleth signals measured from a person during a full sleep study from the LSH dataset. Note that in this study, the pleth and RIP were not fully synchronized in time.

The solid line plot is the coherence between the RIP volume and pleth signals measured from two different people.

Figures 29A, 29B:
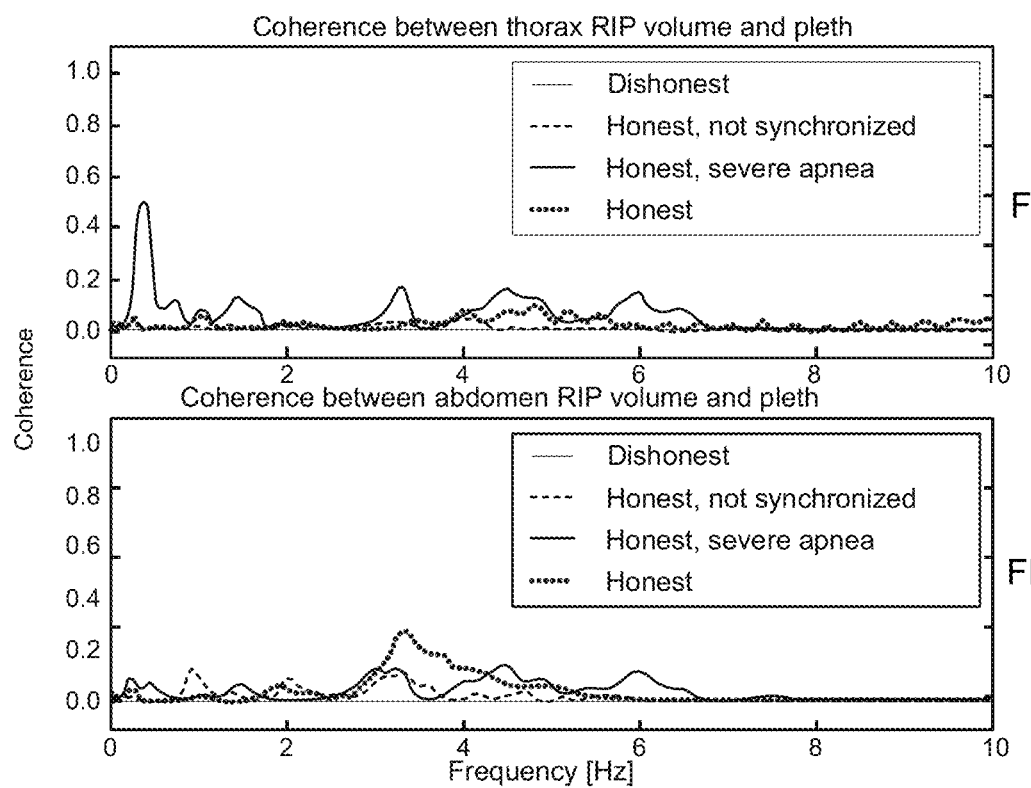
FIGS. 29(A) and 29(B) show a coherence of cleaned thorax and abdomen RIP volume and pleth signals, respectively, for four sleep studies.

In FIGS. 29(A) and 29(B), we can see that there is a noticeable difference between the honest and dishonest sleep studies. That is, the honest sleep studies have higher coherence on the heart's frequency band than the dishonest sleep study. This could imply that the coherence between the whole RIP and pleth signals could be used for constructing a metric that determines whether a person cheated in a sleep study.

4.6.4 Coherence Between Whole RIP and Pleth Envelope Signals

In this subsection, the coherence between whole RIP and pleth envelope signals will be explored. We begin by plotting the coherence for different recordings.

Our proof of concept includes four coherence plots between pleth envelopes and RIP volume signals from four sleep study recordings. These plots can be seen in FIGS. 30(A) and 30(B), which show a coherence of cleaned RIP volume and pleth envelope signals for four sleep studies.

The dotted line plot is the coherence between the RIP volume and pleth envelope signals measured from a relatively healthy person that participated in a partial sleep study.

The bolded line plot is the coherence between the RIP volume and pleth envelope signals measured from a person with severe apnea that participated in a partial sleep study.

The broken line plot is the coherence between the RIP volume and pleth envelope signals measured from a person during a full sleep study from the LSH dataset. Note that in this study, the pleth and RIP were not fully synchronized in time.

The solid line plot is the coherence between the RIP volume and pleth envelope signals measured from two different people.

Figures 30A, 30B:
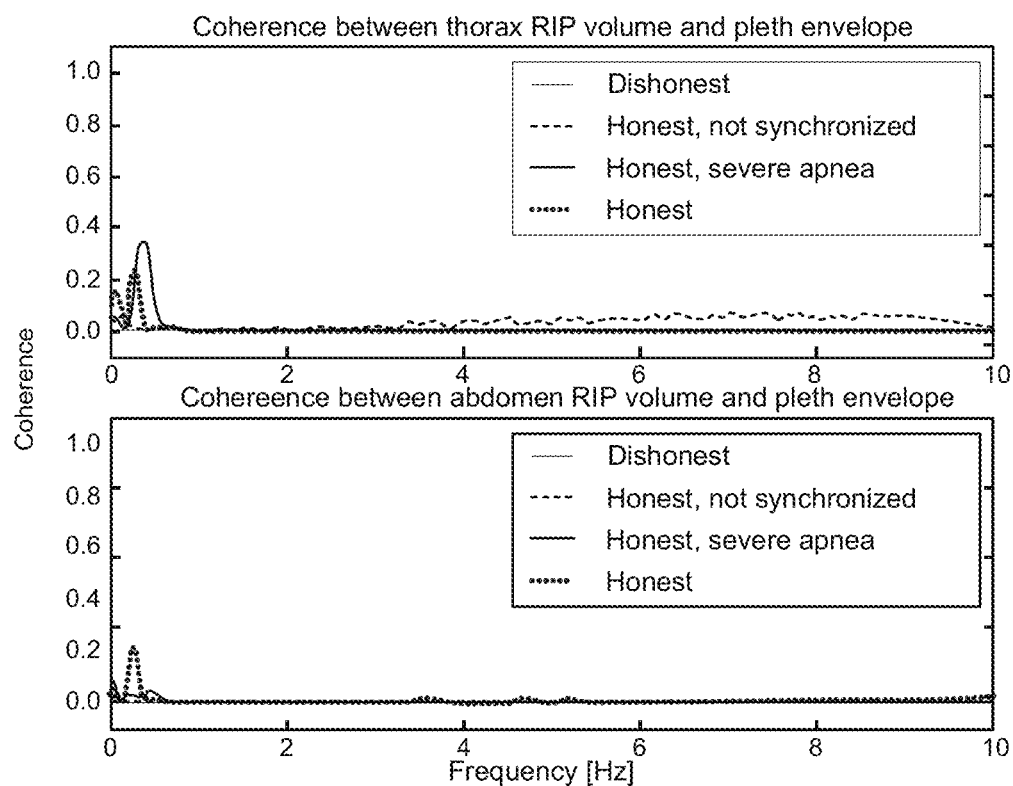
FIGS. 30(A) and 30(B) show a coherence of cleaned thorax and abdomen RIP volume and pleth envelope signals, respectively, for four sleep studies.

In FIGS. 30(A) and 30(B), we can see that there is a noticeable difference between the honest and dishonest sleep studies. That is, the honest sleep studies have higher coherence than the dishonest sleep study. This could imply that the coherence between the whole RIP and pleth envelope signals could be used for constructing a metric that determines whether a person cheated in a sleep study.

4.6.5 Coherence Between Whole RIP Envelope and Pleth Envelope Signals

In this subsection, the coherence between whole RIP envelope and pleth envelope signals will be explored. We begin by plotting the coherence for different recordings.

Our proof of concept includes four coherence plots between pleth envelope and RIP envelope signals from four sleep study recordings. These plots can be seen in FIGS. 31(A) and 31(B), which show a coherence of cleaned RIP volume envelope and pleth envelope signals for four sleep studies The dotted line plot is the coherence between the RIP envelope and pleth envelope signals measured from a relatively healthy person that participated in a partial sleep study.

The bolded line plot is the coherence between the RIP envelope and pleth envelope signals measured from a person with severe apnea that participated in a partial sleep study.

The broken line plot is the coherence between the RIP envelope and pleth envelope signals measured from a person during a full sleep study from the LSH dataset. Note that in this study, the pleth and RIP were not fully synchronized in time.

The solid line plot is the coherence between the RIP envelope and pleth envelope signals measured from two different people.

Figure 31A:
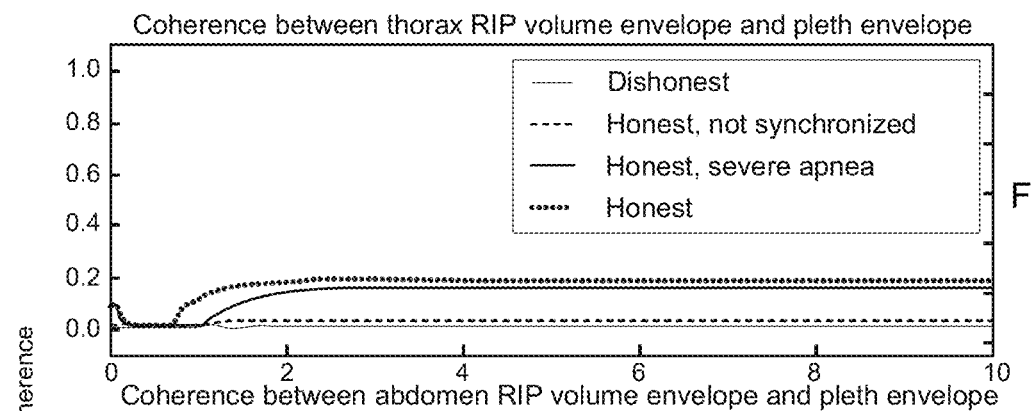
FIGS. 31(A) and 31(B) show a coherence of cleaned thorax and abdomen RIP volume envelope and pleth envelope signals, respectively, for four sleep studies.
Figure 31B:
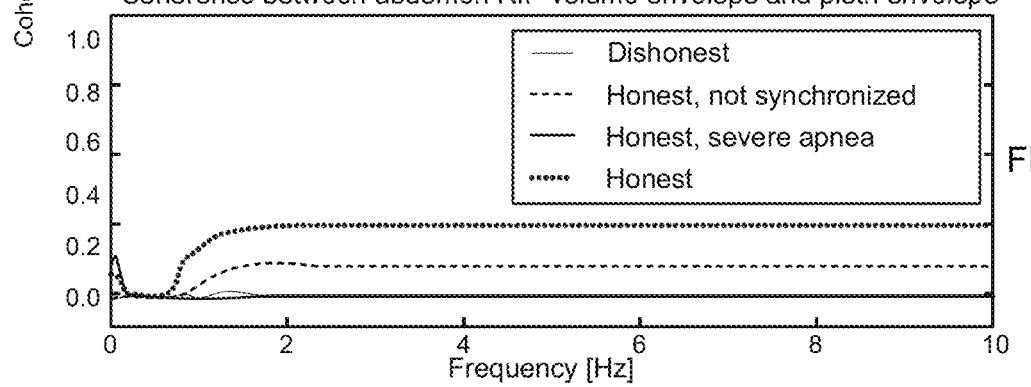

In FIGS. 31(A) and 31(B), we can see that there is a noticeable difference between the honest and dishonest sleep studies. That is, the honest sleep studies have higher coherence than the dishonest sleep study. This could imply that the coherence between the whole RIP envelope and pleth envelope signals could be used for constructing a metric that determines whether a person cheated in a sleep study.

4.6.6 Coherence Between Whole Cannula Flow and Pleth Envelope Signals

In this subsection, the coherence between whole cannula flow and pleth envelope signals will be explored. We begin by plotting the coherence for different recordings.

Our proof of concept includes four coherence plots between pleth envelopes and cannula flow signals from four sleep study recordings. These plots can be seen in FIG. 32, which shows a coherence of cannula flow and pleth envelope signals for four sleep studies The dotted line plot is the coherence between the cannula flow and pleth envelope signals measured from a relatively healthy person that participated in a partial sleep study.

The bolded line plot is the coherence between the cannula flow and pleth envelope signals measured from a person with severe apnea that participated in a partial sleep study.

The broken line plot is the coherence between the cannula flow and pleth envelope signals measured from a person during a full sleep study from the LSH dataset. Note that in this study, the pleth and cannula flow were not fully synchronized in time. Also, note that the cannula flow in this study is not really the cannula flow. Rather, the flow is measured by a CPAP machine. For simplicity, we will continue referring to this flow signal as cannula flow.

The solid line plot is the coherence between the cannula flow and pleth envelope signals measured from two different people.

Figure 32:
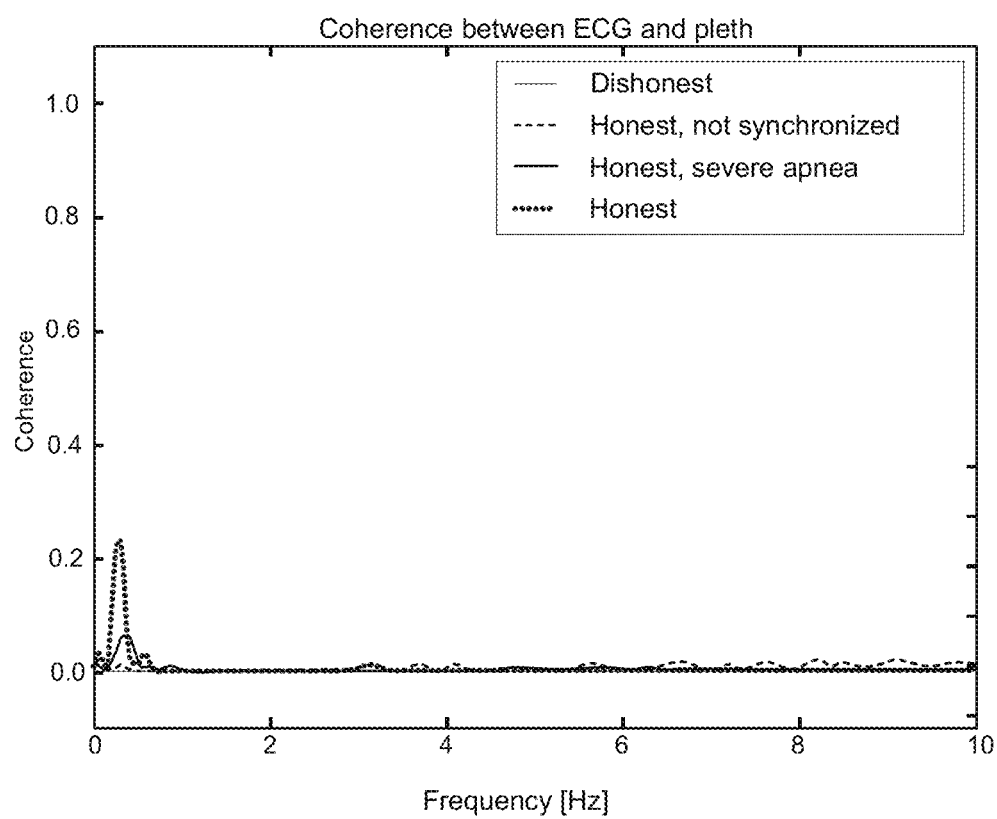
FIG. 32 show a coherence of cannula flow and pleth envelope signals for four sleep studies.

In FIG. 32, we can see that there is a noticeable difference between the honest and dishonest sleep studies. That is, the honest sleep studies have higher coherence than the dishonest sleep study. This could imply that the coherence between the whole cannula flow and pleth envelope signals could be used for constructing a metric that determines whether a person cheated in a sleep study.

5—Metric Analysis and Method Construction

In this section, we will propose metrics derived from coherence that could be used to determine whether a patient is cheating in a sleep study. The metrics will be analyzed and in the end of this section, a method for determining whether a patient is cheating in a sleep study will be proposed.

5.1 Preprocessing of Data Used for the Analysis

The data that was used for analyzing these metrics were 108 PSG recordings (originally 113 PSG recordings but 5 recordings missing signals were removed from the dataset) and 778 PG recordings from LSH. These recordings were assumed to be honest, that is, none of the patients cheated in their sleep study. The dataset was preprocessed in the following way.

1. The SSQC was used for flagging epochs of bad quality in the signals in both PSG and PG recordings. Afterwards, the signals in each recording were downsampled to 20 Hz and saved in pickle files.
2. The preprocessed recordings were split into two sets. The first set remained unchanged and was called the honest recordings. The second set was called the dishonest recordings and was changed in the following way:
    For each pair of two recordings in the dishonest set, we flip-flopped the pleth signal. That is, the first recording's pleth signal was replaced with the second recording's pleth signal and vice versa.
    The PSG recordings were split into 54 honest and 54 dishonest recordings.
    The PG recordings were split into 390 honest and 388 dishonest recordings.
3. Metrics were calculated from the coherence of signal pairs from preprocessed honest and dishonest recordings. These metrics are then saved to pickle files.

5.2 Narrowing Down the Choices

In the analysis described herein, the following metrics were proposed and considered:

- The maximum value of the total coherence
- The maximum value of the coherence on a frequency band of interest
- The mean value of the total coherence
- The mean value of the total coherence on a frequency band of interest
- The standard deviation of the total coherence
- The standard deviation of the total coherence on a frequency band of interest
- The median of the total coherence
- The median of the total coherence on a frequency band of interest
- The coherence value such that the cumulative sum of the total coherence's histogram is 25%
- The coherence value such that the cumulative sum of the total coherence's histogram is 50%
- The coherence value such that the cumulative sum of the total coherence's histogram is 75%
- The maximum value of the coherence calculated for each epoch
- The maximum value of the coherence calculated for each epoch on a frequency band of interest
- The mean value of the coherence calculated for each epoch
- The mean value of the coherence calculated for each epoch on a frequency band of interest
- The standard deviation of the coherence calculated from each epoch
- The standard deviation of the coherence calculated from each epoch on a frequency band of interest
- The median of the coherence calculated for each epoch
- The median of the coherence calculated for each epoch on a frequency band of interest
- The coherence value such that the cumulative sum of the coherence calculated for each epoch histogram is 25%
- The coherence value such that the cumulative sum of the coherence calculated for each epoch histogram is 50%
- The coherence value such that the cumulative sum of the coherence calculated for each epoch histogram is 75

After further analysis, it was decided that although many of the above-listed metrics could be further relied on, working with the following metrics would be sufficient:

- The mean value of the coherence calculated for each epoch; and
- The mean value of the coherence calculated for each epoch on a frequency band of interest.

These metrics will be reviewed in the next subsection and one of them will serve as the basis for the method we will introduce in the end of this section.

5.3 Choosing Metric and Signal Pair

In this subsection, the following chosen metrics will be analyzed:

Metric $\Psi$: The mean value of the coherence calculated for each epoch; and

Metric $\Phi$: The mean value of the coherence calculated for each epoch on a frequency band of interest.

We will begin by analyzing these metrics on each signal-pair combination. Based on the results of the analysis, we will choose a signal pair alongside a single metric for constructing the cheat detection method.

The metrics worked with in this example, were calculated for each 30 second epoch and a typical sleep study recording is c.a. 8 hours long. Therefore, we got c.a. 960 metric values for each metric for each signal pair in a recording. Working with all these values can make the analysis complicated. To simplify the analysis, we analyzed the following metrics for each signal pair computed for our given metrics for each 30-second epoch:

Metric $\bar{\Psi}$: The mean of all values $\Psi$ for a signal pair; and
Metric $\bar{\Phi}$: The mean of all values $\Phi$ for a signal pair.

With these new metrics, we will plot them for each signal pair of interest for all our recordings in the following way We label all the recordings with values 0, 1, . . . ; and A scatter plot will be plotted where each Cartesian coordinate (x, y) will signify the metric $\bar{\Psi}$ or $\bar{\Phi}$ for recording x. The point will be labeled with triangles ($\Delta$) if x is a dishonest recording or with circles ($\bigcirc$) if x is an honest recording.

Figures 33A, 33B:
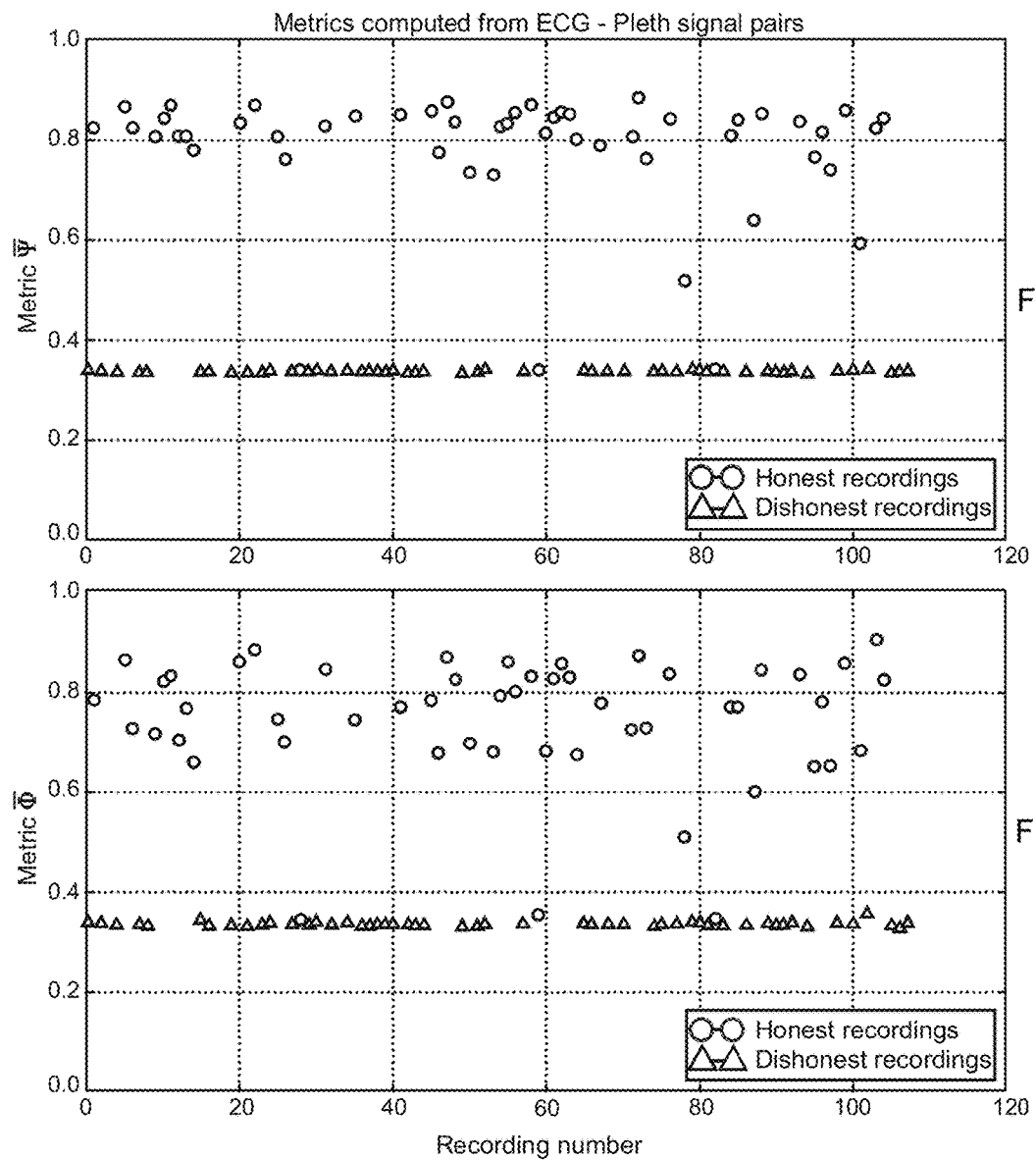
FIGS. 33(A) and 33(B) show metrics $\Psi$ and $\Phi$, respectively, for ECG—pleth signal pairs from all the PSG recordings.
Figure 35A:
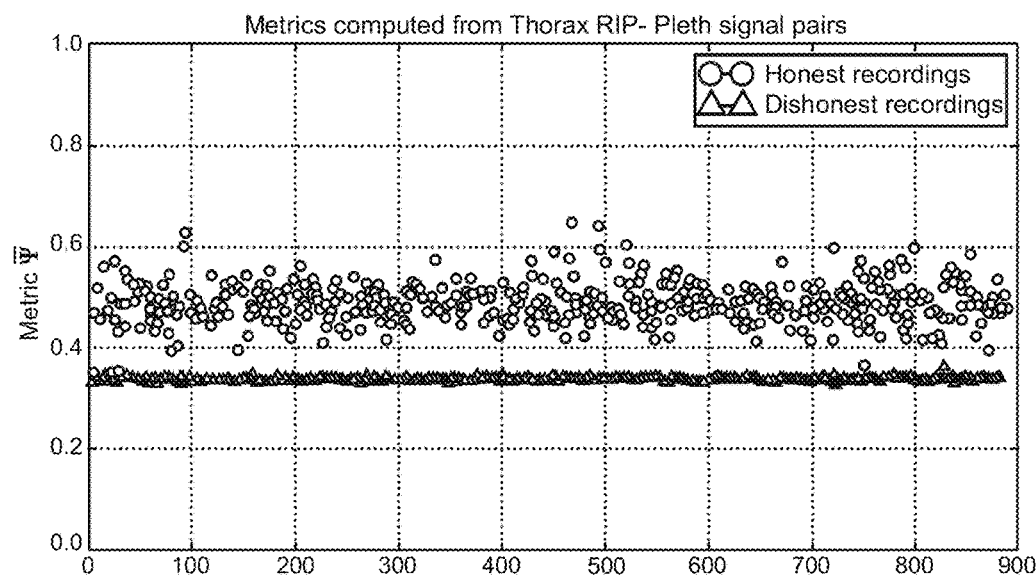
FIGS. 35(A) and 35(B) show metrics $\Psi$ and $\Phi$, respectively, for Thorax RIP—pleth signal pairs from all the PSG and PG recordings.
Figure 35B:
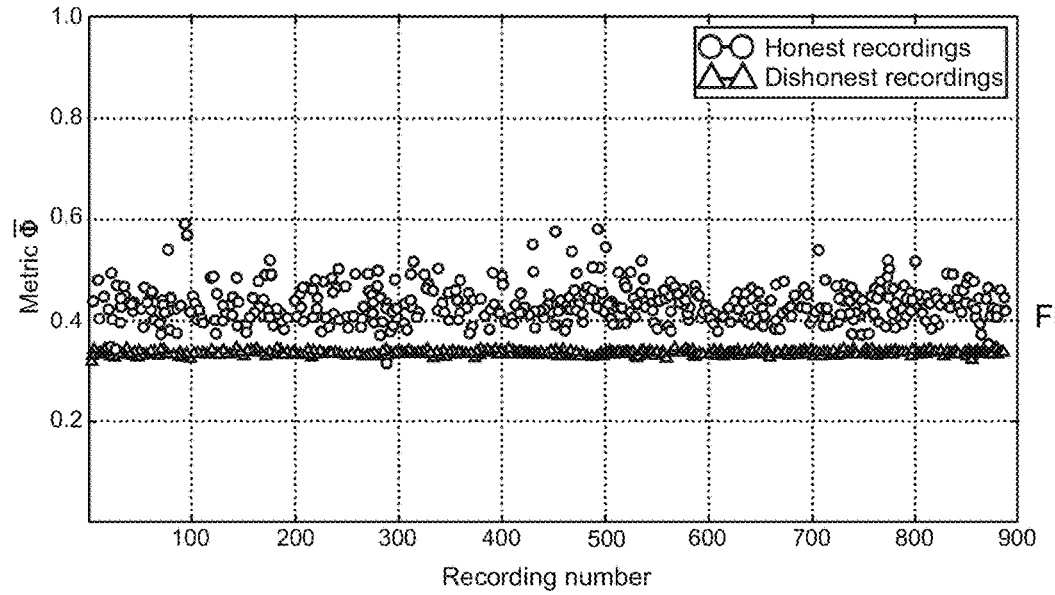
Figures 36A, 36B:
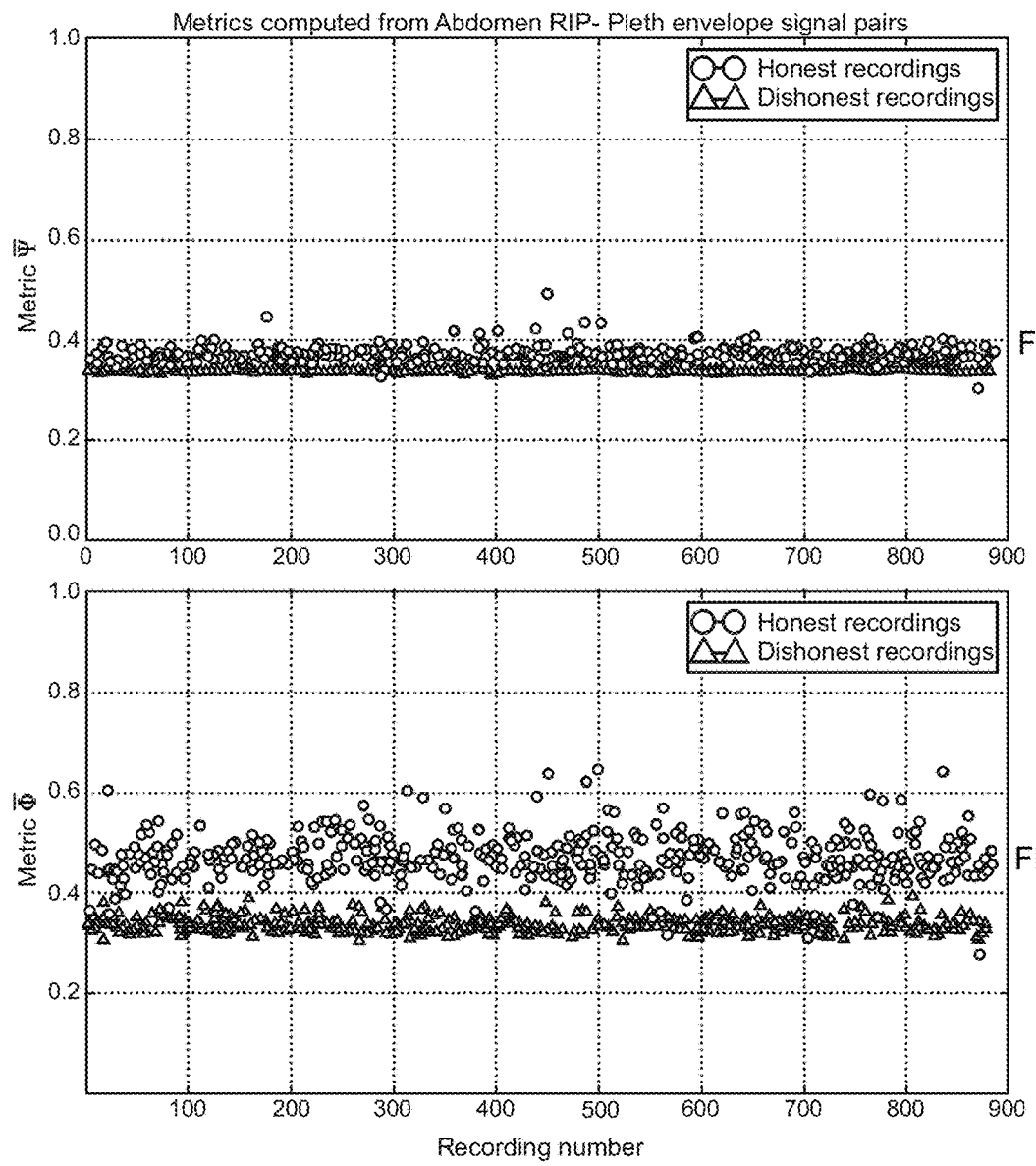
FIGS. 36(A) and 36(B) show metrics $\Psi$ and $\Phi$, respectively, for Abdomen RIP—pleth envelope signal pairs from all the PSG and PG recordings.
Figures 37A, 37B:
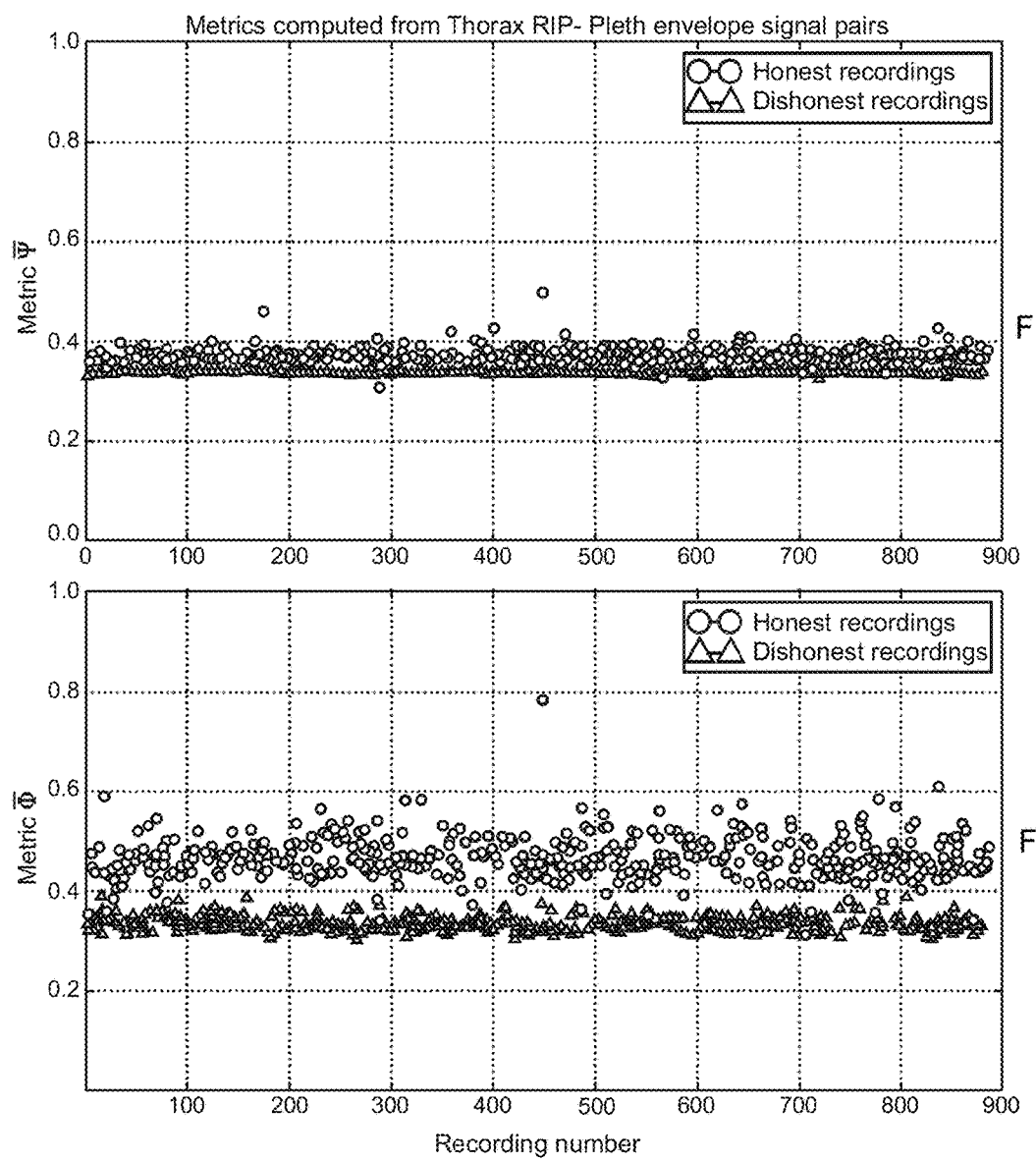
FIGS. 37(A) and 37(B) show metrics $\Psi$ and $\Phi$, respectively, for Thorax RIP—pleth envelope signal pairs from all the PSG and PG recordings.
Figure 38A:
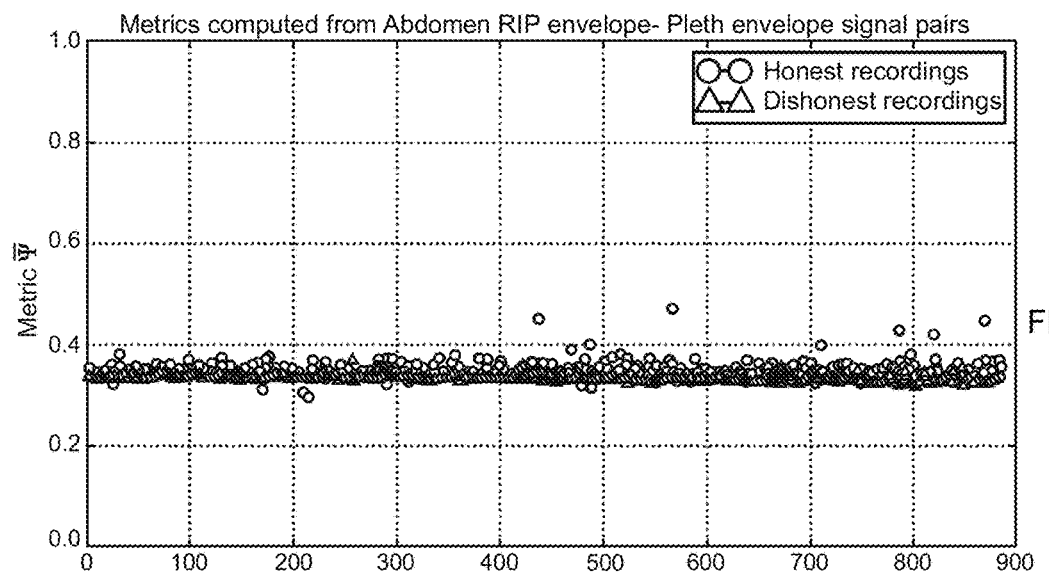
FIGS. 38(A) and 38(B) show metrics $\Psi$ and $\Phi$, respectively, for Abdomen RIP envelope—pleth envelope signal pairs from all the PSG and PG recordings.
Figure 38B:
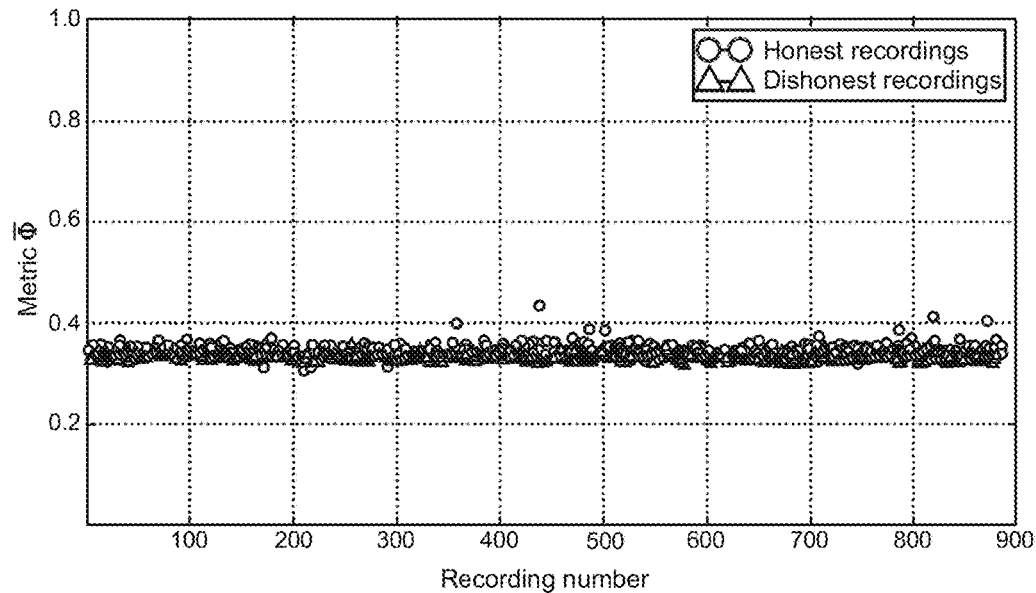
Figures 39A, 39B:
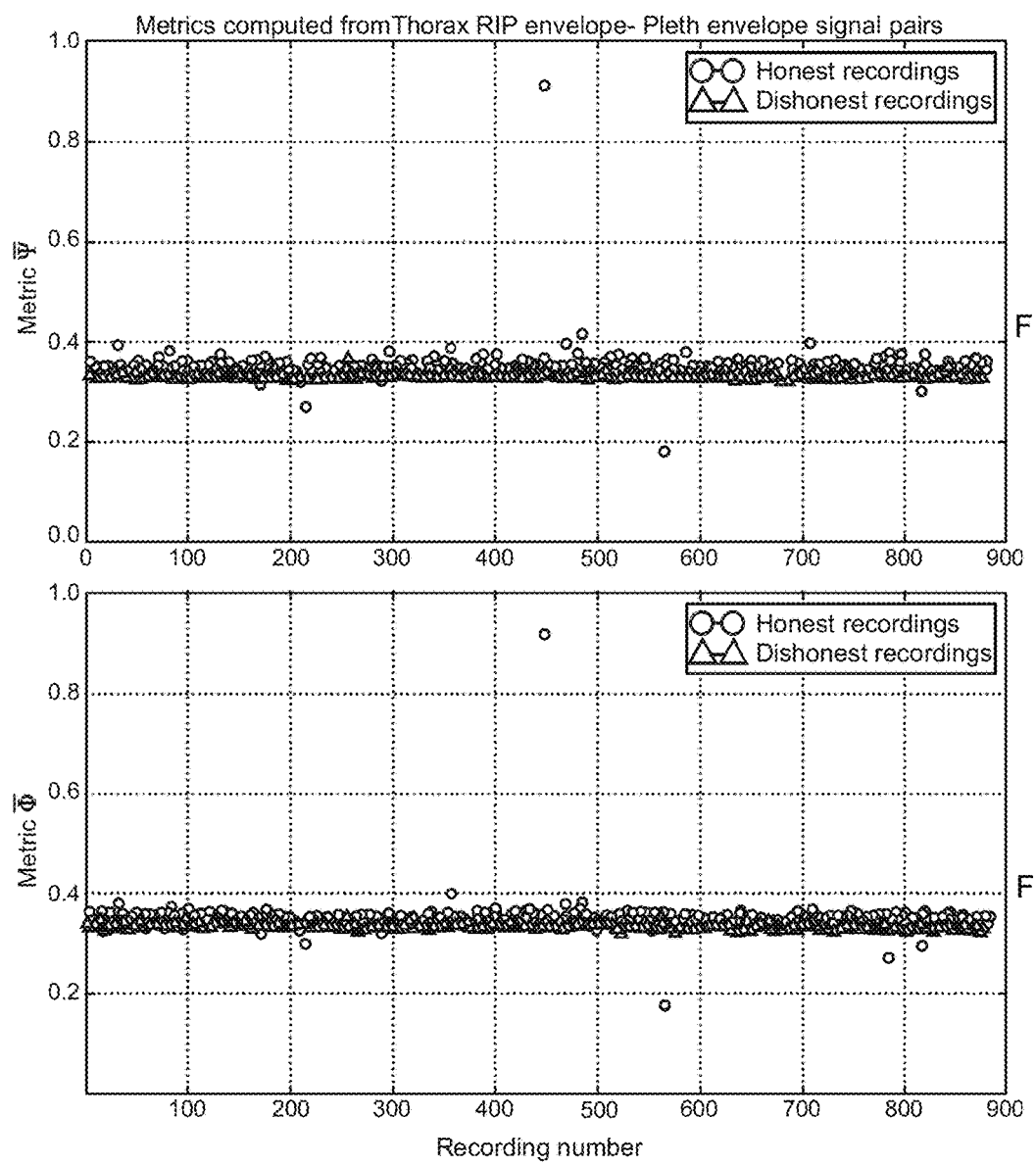
FIGS. 39(A) and 39(B) show metrics $\Psi$ and $\Phi$, respectively, for Thorax RIP envelope—pleth envelope signal pairs from all the PSG and PG recordings.
Figure 40A:
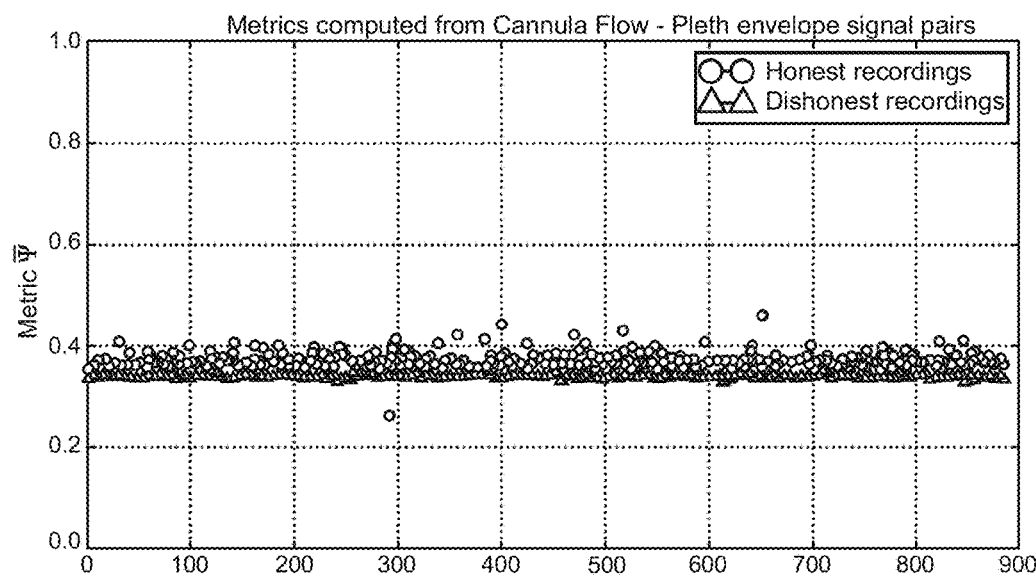
FIGS. 40(A) and 40(B) show metrics $\Psi$ and $\Phi$, respectively, for cannula flow—pleth envelope signal pairs from all the PSG and PG recordings.
Figure 40B:
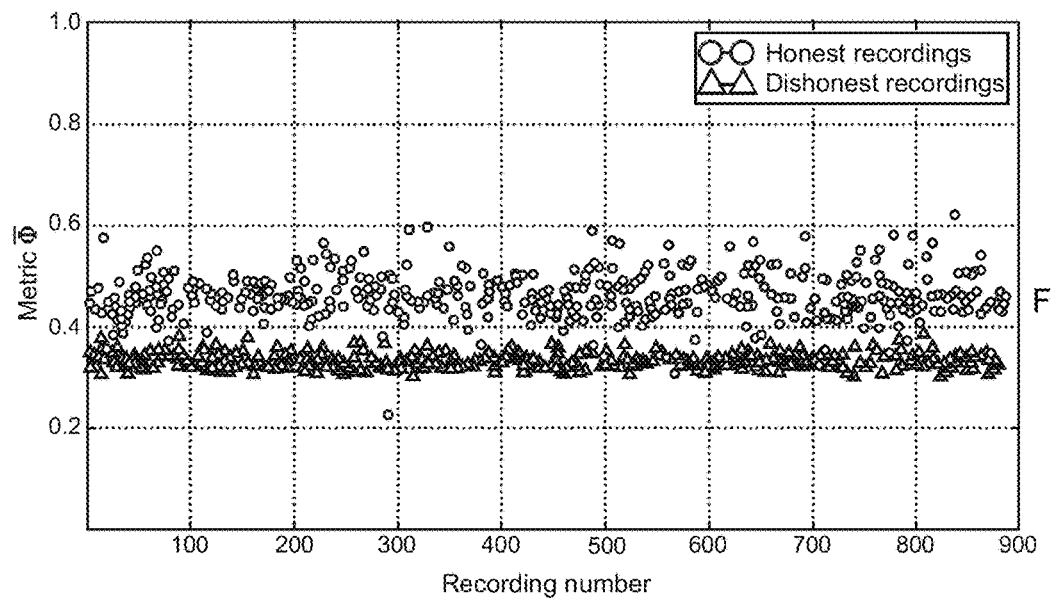

FIGS. 33(A) and 33(B) show metrics $\bar{\Psi}$ and $\bar{\Phi}$ for ECG—pleth signal pairs from all the PSG recordings FIGS. 34(A) and 34(B), and FIGS. 35(A) and 35(B) show metrics $\bar{\Psi}$ and $\bar{\Phi}$ for for RIP—pleth signal pairs from all the PSG and PG recordings FIGS. 36(A) and 36(B), and FIGS. 37(A) and 37(B) show metrics $\bar{\Psi}$ and $\bar{\Phi}$ for RIP—pleth envelope signal pairs from all the PSG and PG recordings FIGS. 38(A) and 38(B), and FIGS. 39(A) and 39(B) show metrics $\bar{\Psi}$ and $\bar{\Phi}$ for RIP envelope—pleth envelope signal pairs from all the PSG and PG recordings FIGS. 40(A) and 40(B) shows metrics $\bar{\Psi}$ and $\bar{\Phi}$ for cannula flow—pleth envelope signal pairs from all the PSG and PG recordings Discernible patterns can be seen in FIGS. 33(A) and 33(B), FIGS. 34(A) and 34(B), FIGS. 35(A) and 35(B), FIGS. 36(A) and 36(B), FIGS. 37(A) and 37(B), FIGS. 38(A) and 38(B), FIGS. 39(A) and 39(B), and FIGS. 40(A) and 40(B). However, the patterns are most discernable in FIGS. 33(A) and 33(B), FIGS. 34(A) and 34(B), and FIGS. 35(A) and 35(B). Therefore, metrics calculated from the ECG-Pleth and RIP-Pleth signal pairs should be sufficient for our cheat detection method.

We will choose the metric $\Psi$ calculated from the RIP-Pleth signal pairs as the metric for determining whether a patient is cheating in a sleep study. The reason is that not all sleep studies include ECG signals and $\Psi$ is a simpler metric than $\Phi$ that performs slightly better.

Though not on topic, metric $\bar{\Psi}$ in FIGS. 34(A) and 34(B) and FIGS. 35(A) and 35(B) show the presence of cardiac artifacts in almost all the RIP recordings. Note that the pleth recordings do have respiratory effects embedded within but the coherence statistic may not detect the effects since all the respiratory presence in the pleth may be tied to the pleth signal's envelope (the respiratory frequency components are modulated into other frequency components).

5.4 the Chosen Metric and Signal Pair

In this subsection, we will perform statistical analysis on the metrics $\Psi$ and $\bar{\Psi}$ computed from RIP-pleth signal pairs. Note that $\Psi$ will be chosen as the metric for determining whether a recording is a cheat recording since $\Psi$ is calculated epoch-wise and $\bar{\Psi}$ is a generalization of $\Psi$ for a whole recording. We included the statistical analysis of $\bar{\Psi}$ as extra information that could be useful in future analysis.

The Metric $\Psi$

In this subsection, we will analyze $\Psi$ with an epoch-wise histogram. The histogram will work as the following:

We collect all metrics $\Psi$ for all epochs for all honest recordings into a flattened array h;

We collect all metrics $\Psi$ for all epochs for all dishonest recordings into a flattened array d; and We plot the histograms of h and d on the same figure.

We plot these histograms two times. Once for the Abdomen RIP volume—Pleth signal pair and another for the Thorax RIP volume—Pleth signal pair. FIGS. 41(A) and 41(B) show a figure with those histograms.

FIGS. 41(A) and 41(B) show the epoch-wise histograms of Abdomen RIP volume—Pleth and Thorax RIP volume—Pleth signal pairs for honest (broken line) and dishonest (solid line) recordings.

Note that the histograms in FIGS. 41(A) and 41(B) are not normalized since that action would make the histograms quite illegible. FIGS. 41(A) and 41(B) shows that there is a significant difference between the probability distribution of $\Psi$ computed from epochs from honest sleep recordings and the probability distribution of $\Psi$ computed from epochs from dishonest sleep recordings.

The Metric $\Psi$

In this subsection, we will analyze $\Psi$ by comparing the probability distributions of $\Psi$ for honest recordings and $\Psi$ for dishonest recordings. For simplicity, we will use the following notation from here on:

$h_{abdomen}$: Array of all metrics $\Psi$ computed from Abdomen RIP—Pleth signal pairs from the honest recordings;

$d_{abdomen}$: Array of all metrics $\Psi$ computed from Abdomen RIP—Pleth signal pairs from the dishonest recordings;

$h_{thorax}$: Array of all metrics $\Psi$ computed from Thorax RIP—Pleth signal pairs from the honest recordings; and $d_{thorax}$: Array of all metrics $\Psi$ computed from Thorax RIP—Pleth signal pairs from the dishonest recordings.

First, we will show that it is sufficient to assume that the probability distributions are Gaussian. Next, we will analyze the probability distributions.

5.4.2.1 can we Assume that the Distributions are Gaussian?

Before calculating some statistical properties from $h_{abdomen}$, $d_{abdomen}$, $h_{thorax}$, and $h_{thorax}$, we removed all the NaN values from those arrays. $\Psi$ is NaN for recordings where either one of the signal pairs (RIP or Pleth) did not pass the signal quality check.

Table 1 contains the sizes of $h_{abdomen}$, $d_{abdomen}$, $h_{thorax}$, and $h_{thorax}$ after the NaN values were removed.

TABLE 1

The number of elements in $h_{abdomen}$, $d_{abdomen}$, $h_{thorax}$, and $h_{thorax}$ after all the NaN values were removed

|  | i = Abdomen | i = Thorax |
| --- | --- | --- |
| Number of elements in $h_i$ | 437 | 435 |
| Number of elements in $d_i$ | 394 | 395 |

Table 2 shows the statistical properties of the values in $h_{abdomen}$, $d_{abdomen}$, $h_{thorax}$, and $d_{thorax}$.

TABLE 2

Statistical properties of values in $h_{abdomen}$, $d_{abdomen}$, $h_{thorax}$, and $d_{thorax}$

|  |  | i = Abdomen | i = Thorax |
| --- | --- | --- | --- |
| Honest recordings | Mean of $h_i$ | 0.5001 | 0.4870 |
|  | Standard deviation of $h_i$ | 0.0472 | 0.0418 |
|  | Kurtosis of $h_i$ | 0.5550 | 1.5320 |
|  | Skewness of $h_i$ | −0.1984 | 0.1795 |

TABLE 2-continued

Statistical properties of values in
$h_{abdomen}$, $d_{abdomen}$, $h_{thorax}$, and $d_{thorax}$

| | | i = Abdomen | i = Thorax |
|---|---|---|---|
| Dishonest recordings | Mean of $d_i$ | 0.3383 | 0.3384 |
| | Standard deviation of $d_i$ | 0.0023 | 0.0023 |
| | Kurtosis of $d_i$ | −0.0386 | 0.2630 |
| | Skewness of $d_i$ | 0.2159 | 0.2419 |

As can be seen in Table 2, it is reasonable to assume that $h_{abdomen}$, $d_{abdomen}$, and $d_{thorax}$ have Gaussian probability distributions since their kurtosis and skewness are not too far away from zero. The term $h_{thorax}$ has an albeit high kurtosis, that is, the probability distribution has a sharper curve than the Gaussian distribution. Since the kurtosis is positive, modeling the probability distribution of $h_{thorax}$ with a Gaussian distribution would give a worst-case estimate if we assume no skewness. For that reason, we will assume that $h_{thorax}$ has a Gaussian distribution.

Note that the skewness is often above 0 in Table 2 so our Gaussian distribution assumption may be a bit liberal. The skewness is though not too far from zero so the uncertainty should be small.

5.4.2.2 Analyzing the Distributions

Using the reasoning from section 5.4, we will assume that $h_{abdomen}$, $d_{abdomen}$, $h_{thorax}$, and $d_{thorax}$ have Gaussian distributions with the means and standard deviations shown in Table 2.

Figure 42:
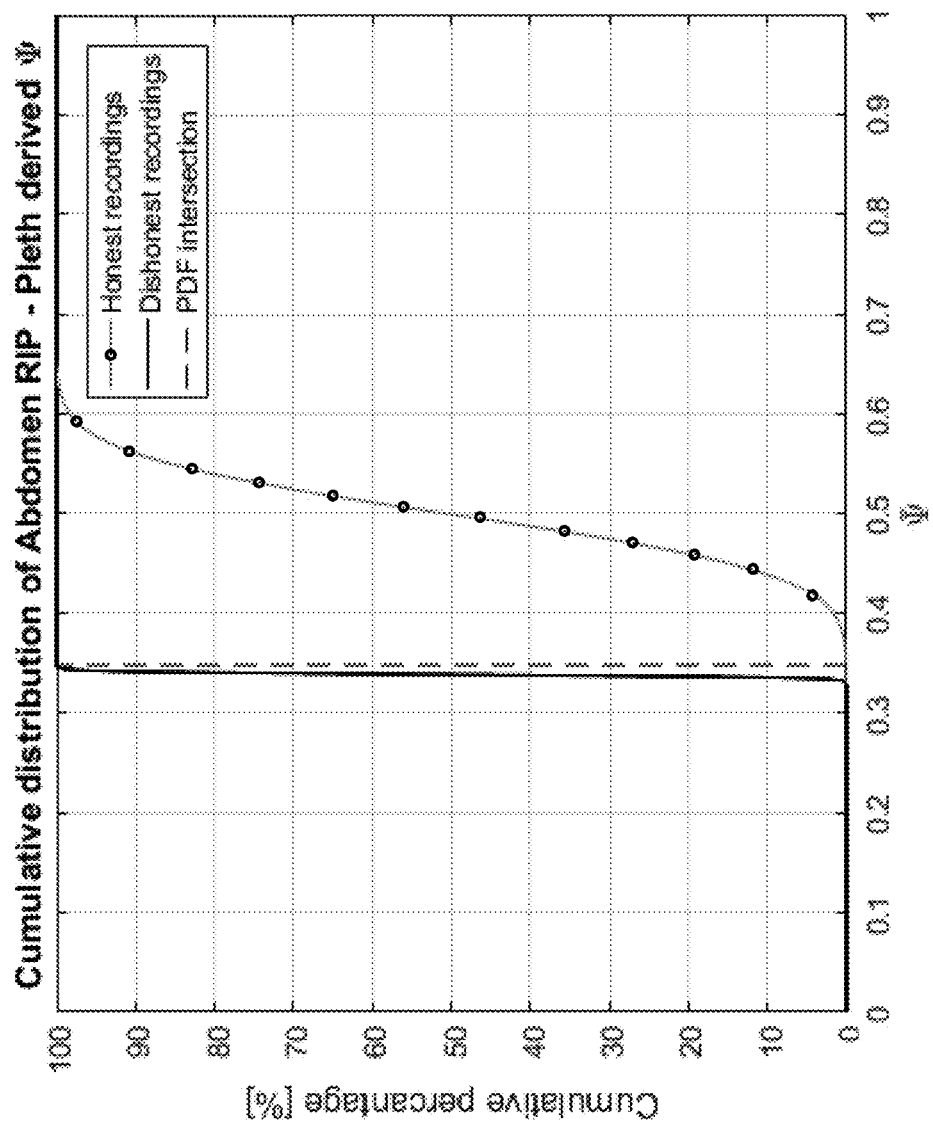
FIG. 42 shows cumulative distribution functions of metric $\Psi$ for honest and dishonest recordings derived from the Abdomen RIP—Pleth signal pairs.

FIG. 42 shows the cumulative distribution functions of P for honest (circled line) and dishonest (solid line) recordings derived from the Abdomen RIP—Pleth signal pair.

Figure 43:
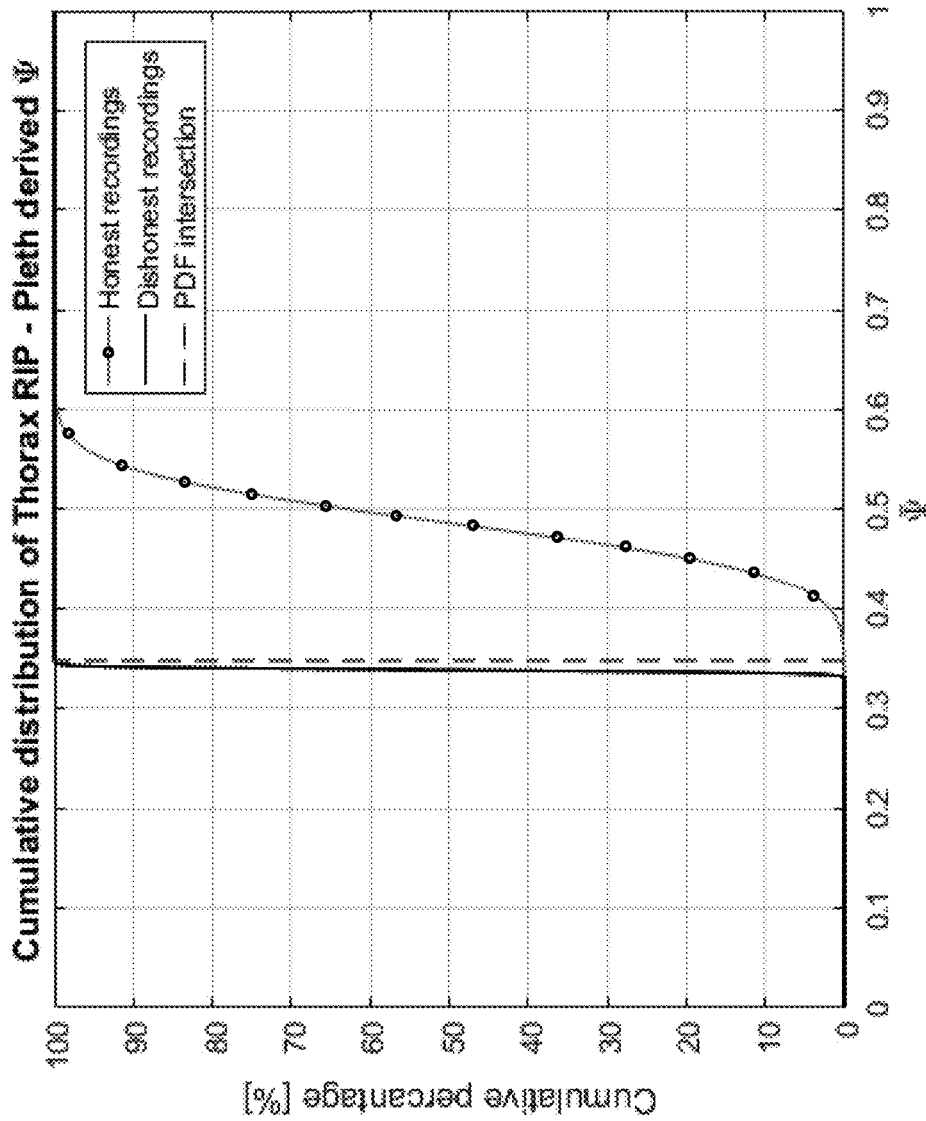
FIG. 43 shows cumulative distribution functions of metric $\Psi$ for honest and dishonest recordings derived from the Thorax RIP—Pleth signal pairs.

FIG. 43 shows the cumulative distribution functions of P for honest (circled line) and dishonest (solid line) recordings derived from the Thorax RIP—Pleth signal pair.

Note that the reason we are looking at the cumulative distribution functions instead of the probability distribution functions is that plotting the probability distribution functions for honest and dishonest recordings together would look illegible.

Note that FIG. 42 and FIG. 43 also show the maximum intersection between the probability distributions of $h_{abdomen}$ and $d_{abdomen}$, and the probability distributions of $h_{thorax}$ and $d_{thorax}$. The intersection was computed with the method described in section 3.5 of this disclosure.

The intersection values alongside some statistical information can be found in Table 3.

TABLE 3

Maximum intersection of $\overline{\Psi}$ alongside statistical information

| | Abdomen - Pleth pair | Thorax - Pleth pair |
|---|---|---|
| Intersection $\overline{\Psi}_0$ | 0.34764 | 0.34785 |
| Probability that a recording with $\Psi < \overline{\Psi}_0$ is dishonest | 0.99998 | 0.99998 |
| Probability that a recording with $\Psi > \overline{\Psi}_0$ is dishonest | 0.00002 | 0.00002 |
| Probability that a recording with $\Psi < \overline{\Psi}_0$ is honest | 0.00062 | 0.00044 |
| Probability that a recording with $\Psi > \overline{\Psi}_0$ is honest | 0.99938 | 0.99956 |

Table 3 shows that the intersection values $\overline{\Psi}_0$ for Abdomen RIP volume—Pleth and Thorax RIP volume—Pleth pairs are suitable threshold values for determining whether a sleep recording is fraudulent. That is, if a certain recording has a metric $\Psi \leq \overline{\Psi}_0$, then we can classify the recording as fraudulent. Otherwise, we can classify the recording as honest.

5.4.3 Testing the Threshold Values on the LSH Dataset

An idea of a classification method was mentioned in [373] and can be summarized as the following:

Given a metric $\Psi$ computed from a recording, if $\Psi \leq \overline{\Psi}_0$, then we can classify the recording that $\Psi$ belongs to as fraudulent. Otherwise, we can classify the recording that $\Psi$ belongs to as honest.

The metric $\overline{\Psi}_0$ is assumed to be the either one of the intersection values from Table 3, depending on if we computed $\Psi$ from Abdomen RIP volume—pleth or Thorax RIP volume—pleth signal pairs.

Table 4 shows the performance of this classification method on our LSH dataset compared to its real classification if $\Psi$ computed from Abdomen RIP volume—Pleth signal pairs.

TABLE 4

Confusion matrix for analyzing the performance of a cheat detection classification method using metrics $\Psi$ computed from Abdomen RIP volume - Pleth signal pairs

| | | Predictive condition | |
|---|---|---|---|
| | | Honest recording | Dishonest Recording |
| True condition | Honest recording | 434 | 3 |
| | Dishonest recording | 0 | 394 |

Table 5 shows the performance of this classification method on our LSH dataset compared to its real classification if $\Psi$ computed from Abdomen RIP volume—Pleth signal pairs.

TABLE 5

Confusion matrix for analyzing the performance of a cheat detection classification method using metrics $\Psi$ computed from Thorax RIP volume - Pleth signal pairs

| | | Predictive condition | |
|---|---|---|---|
| | | Honest recording | Dishonest Recording |
| True condition | Honest recording | 432 | 3 |
| | Dishonest recording | 0 | 395 |

Table 4 and Table 5 show the performance of the classification method is quite good.

Since there are only three outliers, it is within our scope to check these recordings individually. Note that the outliers in Table 4 and Table 5 come from the same recordings. Table 6 shows the metrics computed for these three outliers.

TABLE 6

Metrics computed from the three outliers

| | $\Psi$ computed from Abdomen RIP volume - Pleth pair | $\Psi$ computed from Thorax RIP volume - Pleth pair |
|---|---|---|
| Recording 1 | 0.34327 | 0.34336 |
| Recording 2 | 0.34149 | 0.34139 |
| Recording 3 | 0.34453 | 0.34137 |

As can be seen in Table 6, the metrics of the outliers do not deviate far from the threshold metrics given in Table 3. Therefore, one can assume that these recordings were close to passing the cheat detection test.

FIGS. 44(A), 44(B), and 44(C) show the first outlier recording. The signal quality checker is going a bit overboard. This implies that the cheat detection test may be improved by improving the performance of the signal quality checker.

Figure 45A:
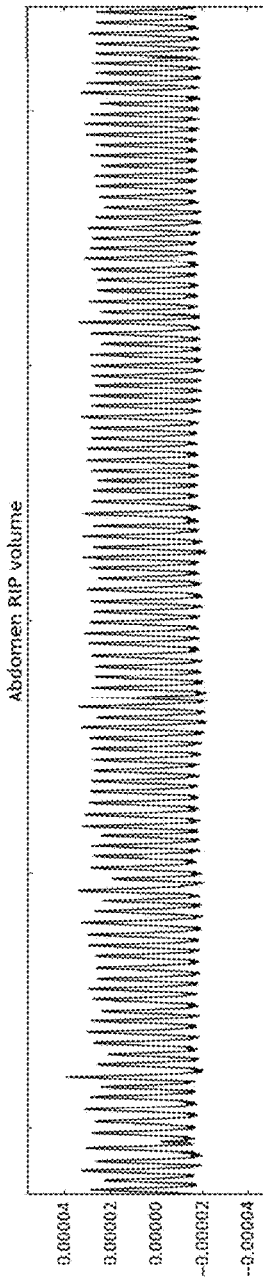
FIGS. 45(A), 45(B), and 45(C) show an outlier recording. Note that the respiration amplitude of the RIP signals are quite stable compared to the amplitude changes in the pleth signal.
Figure 45B:
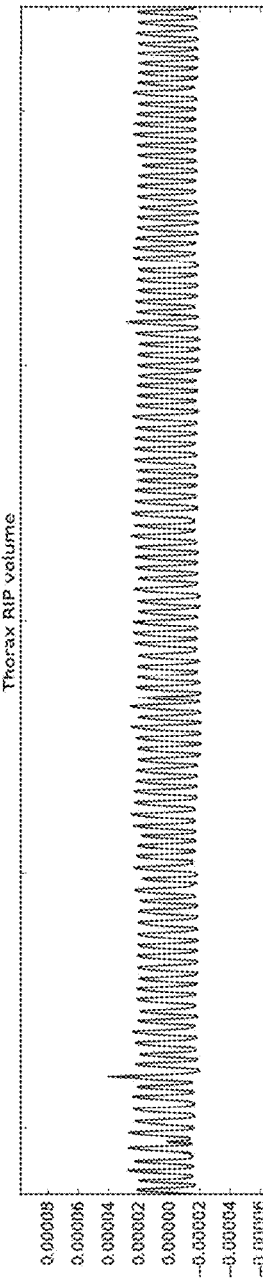
Figure 45C:
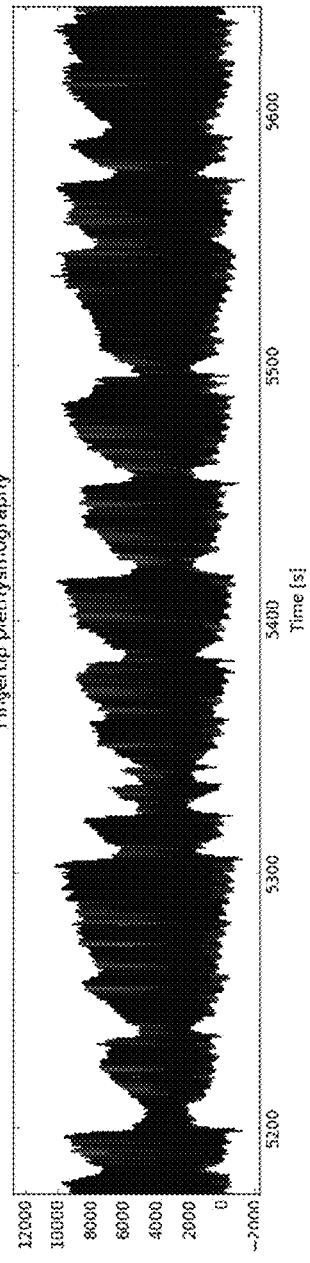

FIGS. 45(A), 45(B), and 45(C) show a part of the second recording. It shows that there are sometimes odd changes in the envelope of the pleth signal. These changes do not seem to be related to the respiratory signals as the RIP signals in these figures seem quite stable (the amplitude of the breaths is not changing dramatically). These changes in the pleth signal could be due to some built-in preprocessing methods in the oximeter or a patient with some special physiological processes.

The third recording seemed normal though, except that the quality of the RIP signal epochs that passed the SSQC were sometimes a bit lax.

5.5 Constructing the Cheat Detection Method

Using the findings from this disclosure, we propose the following method for determining whether a sleep study recording is fraudulent:
1. Extract the following signals from a given recording:
   a. Abdomen RIP volume signal as A,
   b. Thorax RIP volume signal as T, and
   c. Fingertip plethysmography signal as P;
2. Resample A, T, and P to a sampling frequency of 20 Hz;
3. Split A, T, and P into 30 second epochs and denote the ith epoch of A as $A_i$, the ith epoch of T as $T_i$, and the ith epoch of P as $P_i$;
4. Run the SSQC on signals A, T, and P such that the state variable $SA_i$ denotes the quality of epoch $A_i$, $ST_i$ denotes the quality of epoch $T_i$, and $SP_i$ denotes the quality of epoch $P_i$;
(Note that SSQX is also dependent on a separate flow signal (from cannula or CPAP) and oximeter signals (spo2 and pulse).
Also, note that we assume that a state variable takes a value True if the corresponding epoch is of acceptable quality and False if the corresponding epoch is of unacceptable quality.)
5. Calculate the mean of the coherence between $A_i$ and $P_i$ if both $SA_i$ and $SP_i$ are True, for all i, then store these mean values in the vector $m_A$;
6. Calculate the mean of the coherence between $T_i$ and $P_i$ if both $ST_i$ and $SP_i$ are True, for all i. Then store these mean values in the vector $m_T$;
7. Calculate the metric $\overline{\Psi_A}:=\text{mean}(m_A)$ for Abdomen RIP volume—Pleth signal pair;
8. Calculate the metric $\overline{\Psi T_T}:=\text{mean}(m_T)$ for Thorax RIP volume—Pleth signal pair; and
9. If $\overline{\Psi_A} \leq 0.34764$ or $\overline{\Psi_T} \leq 0.34785$, then classify the sleep study recording as fraudulent. Otherwise, classify the sleep study recording as honest.

Note that this method gives the same result as Table 4 and Table 5 if it is applied on our LSH dataset.

6—Discussion

In this section, we will list the outcomes of this disclosure alongside what could have done better and how to improve the work in this disclosure.

To summarize, in this disclosure we determined that calculating a metric from the coherence between RIP signals and a fingertip plethysmography signal could give an idea of whether a person is cheating in a sleep study. A method was proposed based on that metric and it performed well on a large given dataset.

Another significant result from this disclosure is that the analysis methods used implied that cardiac artifacts can virtually be found in any RIP signal (see section [344] of the present disclosure).

In this disclosure, all the data in the LSH dataset could have been used in this disclosure's analysis. That is, alternatively, instead of splitting our LSH dataset into two parts and turning the other part into dishonest sleep recordings, we could have used the whole dataset as honest recording and a mixed copy of itself as the dishonest sleep studies.

Further, the signal quality checker could be improved to validate the proposed cheat detection method on another large dataset.

7—Conclusion

In this section, we conclude on the results from the study listed above. It is evident that the method used can be effectively applied on datasets containing signals from standard sleep studies. As expected, pre-processing the signals and identifying the time periods that gave useful signals improved the efficiency of the method and proved to be important. The tools and mathematics used above are, however, only examples of how the method can be implemented but the tools used are different between applications and signal types and the methods above are therefore in no way fully covering all the possible ways of implementing coherence for conforming that signals are originated from a single person.

According to the present disclosure, the following methods or any combination or permutation of the following methods and steps and features are provided for determining a correspondence of data obtained in a physiological study of a subject comprising, the method first comprising: extracting a first signal from the physiological study; extracting a second signal from the physiological study; determining a coherency value between components of the extracted first signal and components of the extracted second signal; and determining the correspondence of data of the physiological study based on the determined coherency value. According to the method, the first signal and the second signal is obtained by one or more biometric sensors, and data of the first signal and data of the second signal are stored on a memory storage.

The physiological study may be a sleep study.

The methods may further comprise obtaining the first signal and the second signal using the same biosensor device.

The methods may further comprise determining a correspondence of the physiological study data based on the determined correspondence of the first signal and the second signal.

The methods may further comprise determining a quality of the physiological study data based on the determined correspondence of the first signal and the second signal.

The methods may further comprise sampling the first signal at a first sampling frequency.

The methods may further comprise separating a first frequency component from the first signal.

The methods may further comprise sampling the second signal at a second sampling frequency.

The methods may further comprise separating a second frequency component from the second signal.

The methods may further comprise determining a presence within the first signal and the second signal of a trigger signal portion of a same physiological origin.

The first sampling frequency may be the same as the second sampling frequency.

The methods may further comprise breaking the first signal into one or more independent frequency components.

The methods may further comprise breaking the first signal into a primary signal and one or more secondary signals, a frequency of components of the secondary signals of the first signal being largely separated from a frequency of the primary signal of the first signal.

The methods may further comprise breaking the second signal into one or more independent frequency components.

The methods may further comprise breaking the second signal into a primary signal and one or more secondary signals, a frequency of components of the secondary signals of the second signal being largely separated from a frequency of the primary signal of the second signal.

The methods may further comprise identifying a common physiological event shown in both the first signal and the second signal.

The common physiological event may include, but is not limited to, respiration, heartbeat, body movement, brain activity, skin conductance, muscle tone, eye movement, or sound.

The common physiological event may also include, but is not limited to, coupling between physiological events such as respiration and heart beating, or the time from a heart beat occurring to the time a pulse arrives at a location away from the heart.

The step of determining the coherency value may be based on a determination of a coherency between the first frequency component of the first signal at the first sampling frequency and the second frequency component the second signal at the second sampling frequency.

The first signal or the second signal may be a respiratory inductance plethysmography (RIP) signal.

The respiratory inductance plethysmography (RIP) signal may include an abdomen respiratory inductance plethysmography (RIP) signal.

The respiratory inductance plethysmography (RIP) signal may include a thorax respiratory inductance plethysmography (RIP) signal.

The first signal or the second signal may be a plethysmography signal, a fingertip plethysmography signal, an electrocardiogram (ECG) signal, or a cannula flow signal.

The step of determining the coherency value may include measuring coupling strength of common harmonics between the first signal and the second signal, and determining whether at least some components of the first signal and the second signal come from a common physiological origin.

The method may further comprise sampling a first frequency band of the first signal at a first sampling frequency; and sampling a second frequency band of the second signal at a second sampling frequency, wherein the first signal is an electrocardiogram (ECG) signal, the second signal is a plethysmography signal, and the first frequency band and the second frequency band are a frequency band including the heart rate and harmonics of the heart rate in the subject during the physiological study.

The method may further comprise filtering the first signal and the second filter with a low-pass filter.

The method may further comprise determining an envelope for the first signal or the second signal.

The method may further comprise determining the envelope for the first signal or the second signal may include detecting peaks of the first signal or the second signal.

The method may further comprise interpolating the peaks of the first signal or the second signal.

Interpolating the peaks of the first signal or the second signal includes interpolating the peaks of the first signal or the second signal with a B-spline interpolation.

The first signal may be a respiratory inductance plethysmography (RIP) signal, the minimum peak of the first signal may be set to zero, and the minimum distance between peaks of the first signal may be about 2 seconds.

The first signal may be a respiratory inductance plethysmography (RIP) signal, and the minimum distance between peaks of the first signal may be about 2 seconds.

The second signal may be a fingertip plethysmography signal, the minimum peak of the second signal may be set to 4,000, and the minimum distance between peaks of the second signal may be about 0.3 seconds.

The second signal may be a plethysmography signal, and the minimum distance between peaks of the second signal may be about 0.3 seconds.

The method may further comprise passing the detected peaks through a heart variability correction test before the envelope is interpolated.

The method may further comprise determining a quality of the first signal or a quality of the second signal.

The method may further comprise determining whether the first signal or the second signal is within a data quality threshold; and selecting data to be used in the step of determining the coherency value from one or more periods of the physiological study in which the first signal and the second signal is within the data quality threshold.

The step of determining the coherency value may include using a coherence spectrogram.

The method according to an embodiment, includes sampling a first frequency band of the first signal at a first sampling band; and sampling a second frequency band of the second signal at a second sampling band. The first signal is a respiratory inductance plethysmography (RIP) signal, the second signal is a plethysmography signal, and the first sampling band and the second frequency band are the frequency band of a heart beat and the harmonics of the heart beat in the subject during the physiological study.

The plethysmography signal may be a fingertip plethysmography signal.

The first signal or the second signal may be a whole signal.

The first signal or the second signal may be a portion of a signal from a determined epoch.

The first signal may be a plethysmography signal, and the method may further comprise determining an envelope for the first signal to obtain information regarding respiration of the physiological study.

The method may further comprise sampling a first frequency band of the first signal at a first sampling frequency; and sampling a second frequency band of the second signal at a second sampling frequency, wherein the first signal is a respiratory inductance plethysmography (RIP) signal, the second signal is a plethysmography signal, the method further comprises determining an envelope for the first signal and for the second signal, and the first frequency band and the second frequency band are a frequency band comprising the respiration frequency and its harmonics of the subject during the physiological study.

According to the present disclosure, one or more computer-readable mediums may be provided having stored thereon executable instructions that when executed by the one or more processors configure a computer system to perform any of the above-described methods or combinations or permutations of the above-described methods, including at least the following: extract a first signal from a physiological study; extract a second signal from the physiological study; determine a coherency value between components of the extracted first signal and components of the extracted second signal; and determine the correspondence of the physiological study data based on the determined coherency value.

According to the present disclosure, the following systems or any combination or permutation of the following systems and features are provided to determine a correspondence of data of a physiological study, the system comprising: one or more processors; and one or more memory storages, wherein the one or more memory storages have stored thereon the data of the physiological study, and the one or more processors are configured to perform the following extract a first signal from a physiological study; extract a second signal from the physiological study; determine a coherency value between components of the extracted first signal and components of the extracted second signal; and determine the correspondence of the data of the physiological study based on the determined coherency value.

The physiological study may be a sleep study.

The system may further comprise a first biosensor configured to obtain the first signal in the physiological study.

The system may further comprise a second biosensor configured to obtain the second signal in the physiological study.

The system may further comprise a biosensor configured to obtain the first signal and the second signal in the physiological study.

The one or more processors may be configured to determine a correspondence of the physiological study data based on the determined correspondence of the first signal and the second signal.

The one or more processors may be configured to determine a quality of the physiological study data based on the determined correspondence of the first signal and the second signal.

The system may further comprise a first biosensor configured to obtain the first signal and a second biosensor configured to obtain the second signal.

The system may further comprise a memory unit or memory storage configured to receive and store the first signal output from the first biosensor and the second signal output from the second biosensor.

The first signal may be sampled at a first sampling frequency.

The system may be configured to separate a first frequency component from the first signal.

The second signal may be sampled at a second sampling frequency.

A second frequency component may be separated by the system from the second signal.

A presence within the first signal and the second signal of a trigger signal portion of a same physiological origin may be determined by the system.

The the first sampling frequency may be the same as the second sampling frequency.

The first signal may be broken into one or more independent frequency components.

The first signal may be broken by the system into a primary signal and one or more secondary signals, a frequency of components of the secondary signals of the first signal being largely is separated from a frequency of the primary signal of the first signal.

The second signal may be broken or separated by the system into one or more independent frequency components.

The second signal may be broken into a primary signal and one or more secondary signals, a frequency of components of the secondary signals of the second signal is largely separated from a frequency of the primary signal of the second signal.

A common physiological event shown in both the first signal and the second signal may be identified by the system.

The common physiological event may include but is not limited to, respiration, heartbeat, body movement, brain activity, skin conductance, muscle tone, eye movement, or sound.

The common physiological event may also include, but is not limited to, coupling between physiological events such as respiration and heart beating, or the time from a heart beat occurring to the time a pulse arrives at a location away from the heart.

The coherency value may be determined by the system based on a determination of a coherency between the first frequency component of the first signal at the first sampling frequency and the second frequency component the second signal at the second sampling frequency.

The first signal or the second signal may be a respiratory inductance plethysmography (RIP) signal.

The respiratory inductance plethysmography (RIP) signal may include an abdomen respiratory inductance plethysmography (RIP) signal.

The first signal or the second signal may be a plethysmography signal.

The respiratory inductance plethysmography (RIP) signal may include a thorax respiratory inductance plethysmography (RIP) signal.

The first signal or the second signal may be a fingertip plethysmography signal, an electrocardiogram (ECG) signal, or a cannula flow signal.

The coherency value may be determined by the system based at least in part on measuring coupling strength of common harmonics between the first signal and the second signal, and determining whether at least some components of the first signal and the second signal come from a common physiological origin.

The system may be configured to sample a first frequency band of the first signal at a first sampling frequency is sampled; and a second frequency band of the second signal at a second sampling frequency is sampled, and where the first signal is an electrocardiogram (ECG) signal, the second signal is a plethysmography signal, and the first frequency band and the second frequency band are a frequency band including the heart rate and harmonics of the heart rate in the subject during the physiological study.

The first signal and the second filter may be filtered with a low-pass filter.

The system may be configured to determine an envelope for the first signal or the second signal.

The envelope for the first signal or the second signal may be determined by the system based at least in part on detecting peaks of the first signal or the second signal.

The systems may be configured to interpolate peaks of the first signal or the second signal.

Interpolating the peaks of the first signal or the second signal may include interpolating the peaks of the first signal or the second signal with a B-spline interpolation.

The first signal may be a respiratory inductance plethysmography (RIP) signal, the minimum peak of the first signal may be set to zero, and the minimum distance between peaks of the first signal may be about 2 seconds.

The first signal may be a respiratory inductance plethysmography (RIP) signal, and the minimum distance between peaks of the first signal may be about 2 seconds.

According to the systems, the second signal may be a fingertip plethysmography signal, the minimum peak of the second signal may be set to 4,000, and the minimum distance between peaks of the second signal may be about 0.3 seconds.

The second signal may be a plethysmography signal, and the minimum distance between peaks of the second signal may be about 0.3 seconds The detected peaks may be passed through a heart variability correction test by the system before the envelope is interpolated.

The a quality of the first signal or a quality of the second signal may be determined by the system.

The system may make a determination of whether the first signal or the second signal is within a data quality threshold; and select data to be used in the step of determining the coherency value from one or more periods of the physiological study in which the first signal and the second signal is within the data quality threshold.

The systems may determine the coherency value includes using a coherence spectrogram.

The systems may bay be configured to: sample a first frequency band of the first signal at a first sampling frequency; and sample a second frequency band of the second signal at a second sampling frequency, where the first signal is a respiratory inductance plethysmography (RIP) signal, the second signal is a plethysmography signal, and the first sampling band and the second sampling band are a frequency band of a heart eat and the harmonics of the heart beat in the subject during the physiological study.

The plethysmography signal may be a fingertip plethysmography signal.

The first signal or the second signal may be a whole signal.

The first signal or the second signal may be a portion of a signal from a determined epoch.

The first signal may be a plethysmography signal, and the system may be configured to determine an envelope for the first signal to obtain information regarding respiration of the physiological study.

The systems may be further configured to sample a first frequency band of the first signal at a first sampling band; and sample a second frequency band of the second signal at a second sampling band, where the first signal is a respiratory inductance plethysmography (RIP) signal, the second signal is a plethysmography signal, the method further comprises determining an envelope for the first signal and for the second signal, and the first sampling band and the second sampling band are frequency band including a respiration frequency and its harmonics of the subject during the physiological study.

Also according to the present disclosure, a method for maintaining a chain of custody of physiological study data for a subject is provided, comprising any of the above-described methods or combinations or permutations of the above-described methods, including at least the following the method comprising: providing to the subject a physiological study system, the physiological study system including one or more sensors configured to obtain physiological study data, the physiological study data including a first signal from the physiological study and a second signal from the physiological study; obtaining a confirmation that the one or more sensors have been placed on the subject; receiving the physiological study data; extracting a first signal from the physiological study; extracting a second signal from the physiological study; determining a coherency value between components of the extracted first signal and components of the extracted second signal; and determining the correspondence of the physiological study data based on the determined coherency value. The physiological study may be a sleep study.

Certain terms are used herein throughout the description and claims to refer to particular methods, features, or components. As those having ordinary skill in the art will appreciate, different persons may refer to the same methods, features, or components by different names. This disclosure does not intend to distinguish between methods, features, or components that differ in name but not function. The figures are not necessarily to scale. Certain features and components herein may be shown in exaggerated scale or in somewhat schematic form and some details of conventional elements may not be shown or described in interest of clarity and conciseness.

Although various example embodiments have been described in detail herein, those skilled in the art will readily appreciate in view of the present disclosure that many modifications are possible in the example embodiments without materially departing from the concepts of present disclosure. Accordingly, any such modifications are intended to be included in the scope of this disclosure. Likewise, while the disclosure herein contains many specifics, these specifics should not be construed as limiting the scope of the disclosure or of any of the appended claims, but merely as providing information pertinent to one or more specific embodiments that may fall within the scope of the disclosure and the appended claims. Any described features from the various embodiments disclosed may be employed in combination. In addition, other embodiments of the present disclosure may also be devised which lie within the scopes of the disclosure and the appended claims. Each addition, deletion, and modification to the embodiments that falls within the meaning and scope of the claims is to be embraced by the claims.

Certain embodiments and features may have been described using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated. Certain lower limits, upper limits and ranges may appear in one or more claims below. Any numerical value is "about" or "approximately" the indicated value, and takes into account experimental error and variations that would be expected by a person having ordinary skill in the art.

What is claimed:

1. A method for determining whether a first signal and a second signal of a physiological study originate from a same intended subject, the method comprising:
    extracting the first signal from the physiological study, the physiological study being a sleep study, the first signal being a respiratory inductance plethysmography (RIP) signal obtained in the sleep study;
    extracting the second signal from the physiological study, the second signal being a pulse-measuring signal obtained in the sleep study, and data of the RIP signal and data of the pulse-measuring signal being stored on a memory storage;

determining a coherency value between components of the RIP signal and components of the pulse-measuring signal;

determining whether the RIP signal and the pulse-measuring signal originate from the same intended subject based on the determined coherency value; and wherein determining the coherency value includes
sampling a first frequency band of the RIP signal,
sampling a second frequency band of the pulse-measuring signal, and
determining whether a synchronous relationship exists between components of the first frequency band of the RIP signal and the second frequency band of the pulse-measuring signal,
wherein the first frequency band and the second frequency band include heart rate and/or harmonics of the heart rate and/or respiratory rate and/or harmonics of the respiratory rate in the subject during the physiological study, wherein
in a case that the RIP signal and the pulse-measuring signal are determined to originate from the same intended subject, data of the physiological study is indicated to be usable for diagnosing a sleep disorder of the intended subject or determining that the intended subject does not suffer from a sleep disorder, and
in a case the case that the RIP signal and the pulse-measuring signal are determined to not originate from the same intended subject, data of the physiological study is indicated to be falsified.

2. The method according to claim 1, further comprising determining a presence within the first signal and the second signal of a trigger signal portion of a same physiological origin.

3. The method according to claim 1, wherein the second signal includes a photoplethysmography signal, an electrocardiogram (ECG) signal, an accelerometer signal, a pulse oximeter, a pulse plethysmography signal, a pulse meter signal, and/or an audio signal.

4. The method according to claim 1, wherein the step of determining the coherency value is based on a determination of a coherency between a first frequency component of the first signal and a second frequency component of the second signal.

5. The method according to claim 1, further comprising identifying a further common physiological event present in both the first signal and the second signal.

6. The method according to claim 1, further comprising identifying a further common physiological event present in both the first signal and the second signal, wherein the common physiological event includes one or more, or coupling between, body movement, brain activity, skin conductance, muscle tone, eye movement, or sound.

7. The method according to claim 1, wherein the step of determining the coherency value includes measuring a coupling strength of common harmonics between the first signal and the second signal, and determining whether at least some components of the first signal and the second signal originate from a common physiological origin.

8. The method according to claim 1, wherein
the second signal is a photoplethysmography signal, and
the first frequency band and the second frequency band include the heart rate and harmonics of the heart rate in the subject during the physiological study.

9. The method according to claim 1, wherein the first frequency band and the second frequency band include heart rate and harmonics of the heart rate in the subject during the physiological study.

10. The method according to claim 1, wherein the second signal is a plethysmography signal.

11. The method according to claim 1, wherein the first frequency band and the second frequency band include respiratory rate and harmonics of the respiratory rate in the subject during the physiological study.

12. The method according to claim 1, wherein the respiratory inductance plethysmography (RIP) signal is obtained by one or more RIP belts, and
wherein the method further comprises detecting during the physiological study whether the one or more RIP belts becomes disconnected from the intended subject.

13. The method according to claim 1, further comprising monitoring of the intended subject during the physiological study with a camera to confirm that the first signal and the second signal are obtained from the intended subject of the physiological study.

14. A system to determine whether a first signal and a second signal of a physiological study originate from a same intended subject, the system comprising:
one or more processors; and
one or more memory storages, wherein the one or more memory storages have stored thereon the data of the physiological study,
wherein the one or more processors are configured to perform the following
extract the first signal from the physiological study, the physiological study being a sleep study, the first signal being a respiratory inductance plethysmography (RIP) signal obtained in the sleep study;
extract the second signal from the physiological study, the second signal being a pulse-measuring signal obtained in the sleep study, and data of the RIP signal and data of the pulse-measuring signal being stored on the one or more memory storage devices;
determine a coherency value between components of the extracted RIP signal and components of the pulse-measuring signal; and
determine whether the RIP signal and the pulse-measuring signal originate from the same intended subject based on the determined coherency value,
wherein the one or more processors determines the coherency value by
sampling a first frequency band of the RIP signal,
sampling a second frequency band of the pulse-measuring signal, and
determining whether a synchronous relationship exists between components of the first frequency band of the RIP signal and the second frequency band of the pulse-measuring signal,
wherein the first frequency band and the second frequency band include heart rate and/or harmonics of the heart rate and/or respiratory rate and/or harmonics of the respiratory rate in the subject during the physiological study, wherein
in a case that the RIP signal and the pulse-measuring signal are determined to originate from the same intended subject, the one or more processors indicates data of the physiological study to be usable for diagnosing a sleep disorder of the intended subject or determining that the intended subject does not suffer from a sleep disorder, and in a case that the RIP signal and the pulse-measuring signal are determined to not originate from the same intended subject, the one or more processors indicates data of the physiological study to be indicated to be falsified.

15. The system according to claim 14, wherein the one or more processors are further configured to determine a presence within the first signal and the second signal of a trigger signal portion of a same physiological origin.

16. The system according to claim 14, wherein the second signal includes a photoplethysmography signal, an electrocardiogram (ECG) signal, an accelerometer signal, a pulse oximeter, a pulse plethysmography signal, a pulse meter signal, or an audio signal.

17. The system according to claim 14, wherein the one or more processors are further configured to determine the coherency value based on a determination of a coherency between a first frequency component of the first signal and a second frequency component of the second signal.

18. The system according to claim 14, wherein the one or more processors are further configured to identify a further common physiological event present in both the first signal and the second signal.

19. The system according to claim 18, wherein the common physiological event includes one or more, or coupling between, body movement, brain activity, skin conductance, muscle tone, eye movement, or sound.

20. The system according to claim 14, wherein the one or more processors are further configured to determine the coherency value by measuring a coupling strength of common harmonics between the first signal and the second signal, and determining whether at least some components of the first signal and the second signal originate from a common physiological origin.

21. One or more non-transitory computer-readable mediums having stored thereon executable instructions that when executed by one or more processors configure a computer system to perform a method for determining whether a first signal and a second signal of a physiological study originate from a same intended subject based, including the following:

extract the first signal from the physiological study, the physiological study being a sleep study, the first signal being a respiratory inductance plethysmography (RIP) signal obtained in the sleep study;

extract the second signal from the physiological study, the second signal being a pulse-measuring signal obtained in the sleep study, and data of the RIP signal and data of the pulse-measuring signal being stored on the one or more memory storage device;

determine a coherency value between components of the RIP signal and components of the pulse-measuring signal; and determine whether the RIP signal and the pulse-measuring signal originate from the same intended subject based on the determined coherency value, wherein the one or more processors determines the coherency value by sampling a first frequency band of the RIP signal, sampling a second frequency band of the pulse-measuring signal, and determining whether a synchronous relationship exists between components of the first frequency band of the RIP signal and the second frequency band of the pulse-measuring signal, wherein the first frequency band and the second frequency band include heart rate and/or harmonics of the heart rate and/or respiratory rate and/or harmonics of the respiratory rate in the subject during the physiological study, wherein in a case that the RIP signal and the pulse-measuring signal are determined to originate from the same intended subject, the one or more processors indicates data of the physiological study to be usable for diagnosing a sleep disorder of the intended subject or determining that the intended subject does not suffer from a sleep disorder, and in a case the case that the RIP signal and the pulse-measuring signal are determined to not originate from the same intended subject, the one or more processors indicates data of the physiological study to be indicated to be falsified.

* * * * *